US009539098B2

(12) United States Patent
Klinger et al.

(10) Patent No.: US 9,539,098 B2
(45) Date of Patent: Jan. 10, 2017

(54) SYSTEM FOR MODULAR HIP RESURFACING

(71) Applicant: RevOrtho LLC, Great Neck, NY (US)

(72) Inventors: Craig Eric Klinger, Great Neck, NY (US); Jose Bernardo Toro Arbelaez, Remsenburg-Speonk, NY (US)

(73) Assignee: Rev Ortho LLC, Great Neck, NY (US)

( * ) Notice: Subject to any disclaimer, the term of this patent is extended or adjusted under 35 U.S.C. 154(b) by 3 days.

(21) Appl. No.: 14/223,518

(22) Filed: Mar. 24, 2014

(65) Prior Publication Data

US 2014/0316531 A1 Oct. 23, 2014

Related U.S. Application Data

(60) Provisional application No. 61/815,255, filed on Apr. 23, 2013, provisional application No. 61/841,892, filed on Jul. 1, 2013.

(51) Int. Cl.
*A61F 2/36* (2006.01)
*A61F 2/46* (2006.01)
(Continued)

(52) U.S. Cl.
CPC ............ *A61F 2/3603* (2013.01); *A61B 17/15* (2013.01); *A61B 17/1668* (2013.01);
(Continued)

(58) Field of Classification Search
CPC ................ A61F 2/36–2/3609; A61F 2002/3611–2002/3621; A61F 2002/3605; A61B 17/15; A61B 17/1668; A61B 17/1637; A61B 17/1721; A61B 17/175; A61B 17/1753
See application file for complete search history.

(56) References Cited

U.S. PATENT DOCUMENTS 4,123,806 A 11/1978 Amstutz et al.
4,224,699 A 9/1980 Weber
(Continued)

FOREIGN PATENT DOCUMENTS

DE 1164019 * 2/1964
EP 0418301 B1 * 6/1989
(Continued)

OTHER PUBLICATIONS

International Search Report and Written Opinion issued in PCT/US2015/045713, dated Nov. 24, 2015.

*Primary Examiner* — Marcia Watkins
(74) *Attorney, Agent, or Firm* — Michael T. Abramson; Holland & Knight LLP

(57) ABSTRACT

A scalable modular hip resurfacing arthroplasty system includes (1) an alignment guide for precise guide pin insertion, (2) a modular cannulated cylindrical reamer assembly for accurate femoral head cylindrical reaming and central bone channel drilling, (3) a saw guide for an accurate femoral head osteotomy, (4) a soft tissue protector with a stepped design to shield and retract tissues, (5) a hip retractor that seats onto a prepared femur, (6) an outer hole drill guide aiding drilling of peripheral holes, and (7) a femoral resurfacing implant with a cap portion and central stem adapted for multiple modular attachments including plates. A method for preparing the proximal femur for hip resurfacing with novel stepped cylindrical femoral head osteotomy and central bone channel drilling, leaving an intact collar of cortical bone above the femoral head articular rim.

25 Claims, 34 Drawing Sheets

(51) Int. Cl.
*A61B 17/15* (2006.01)
*A61B 17/16* (2006.01)
*A61B 17/17* (2006.01)
*A61B 17/56* (2006.01)
*A61B 17/00* (2006.01)
*A61B 17/74* (2006.01)
*A61F 2/30* (2006.01)

(52) U.S. Cl.
CPC ........ *A61B 17/175* (2013.01); *A61B 17/1721* (2013.01); *A61B 17/1697* (2013.01); *A61B 17/1753* (2013.01); *A61B 17/746* (2013.01); *A61B 2017/0046* (2013.01); *A61F 2002/30299* (2013.01); *A61F 2002/30405* (2013.01); *A61F 2002/30433* (2013.01); *A61F 2002/30878* (2013.01)

(56) References Cited

U.S. PATENT DOCUMENTS

| | | |
|---|---|---|
| 5,725,593 A | 3/1998 | Caracciolo |
| 5,766,263 A | 6/1998 | Grundei et al. |
| 6,156,069 A | 12/2000 | Amstutz |
| 6,503,281 B1 | 1/2003 | Mallory |
| 6,695,883 B2 | 2/2004 | Crofford |
| 8,152,855 B2 | 4/2012 | Tulkis et al. |
| 2003/0100907 A1* | 5/2003 | Rosa ............... A61B 17/155 606/86 R |
| 2003/0130741 A1 | 7/2003 | McMinn |
| 2003/0163202 A1 | 8/2003 | Lakin |
| 2003/0229357 A1 | 12/2003 | Dye |
| 2004/0193276 A1* | 9/2004 | Maroney ........... A61B 5/1077 623/19.14 |
| 2005/0081867 A1 | 4/2005 | Murphy |
| 2006/0271058 A1 | 11/2006 | Ashton et al. |
| 2007/0233136 A1 | 10/2007 | Wozencroft |
| 2007/0260256 A1 | 11/2007 | Beaule |
| 2007/0299451 A1* | 12/2007 | Tulkis ............... A61B 17/175 606/79 |
| 2008/0109085 A1 | 5/2008 | Tulkis et al. |
| 2009/0048681 A1 | 2/2009 | Vlachos |
| 2009/0118736 A1 | 5/2009 | Kreuzer |
| 2009/0192620 A1* | 7/2009 | Ebbitt ............... A61F 2/4607 623/18.11 |
| 2010/0023131 A1 | 1/2010 | Crofford et al. |
| 2010/0049329 A1 | 2/2010 | Vio et al. |
| 2010/0298949 A1 | 11/2010 | McMinn et al. |
| 2012/0022543 A1 | 1/2012 | Porzel et al. |
| 2012/0165820 A1 | 6/2012 | De Smedt et al. |

FOREIGN PATENT DOCUMENTS

| | | | |
|---|---|---|---|
| FR | 2686503 A1 * | 7/1993 | ........... A61F 2/3603 |
| GB | 2 007 980 B | 5/1979 | |

* cited by examiner

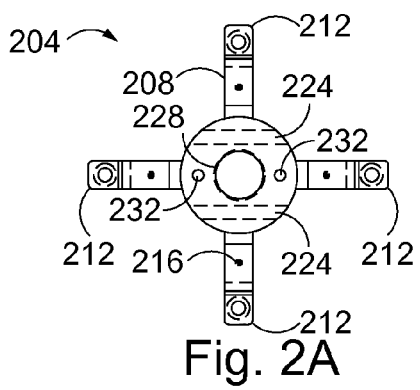
Fig. 2A
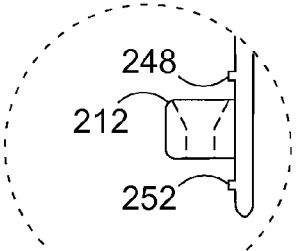
Fig. 2C
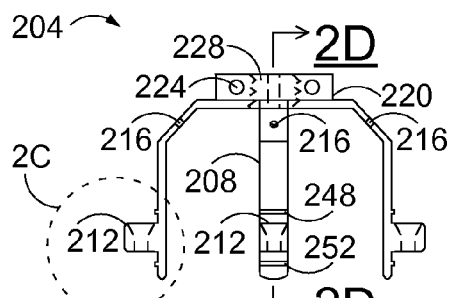
Fig. 2B
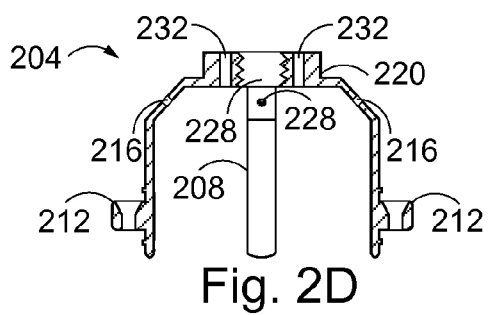
Fig. 2D
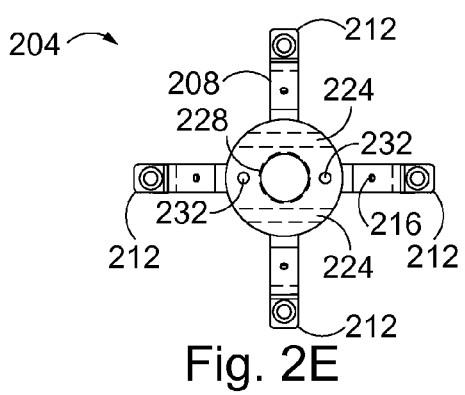
Fig. 2E
Fig. 2J  Fig. 2K
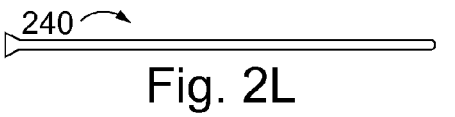
Fig. 2L
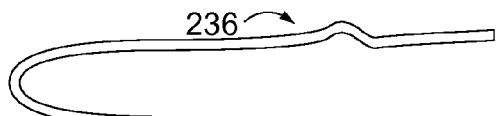
Fig. 2F
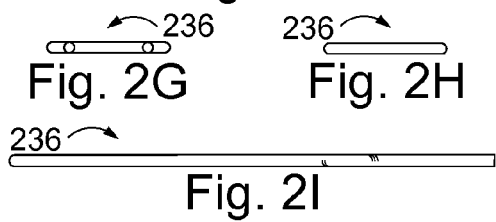
Fig. 2G  Fig. 2H
Fig. 2I
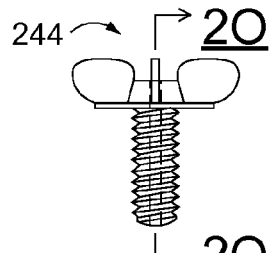
Fig. 2M  Fig. 2N
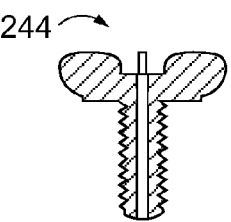
Fig. 2O
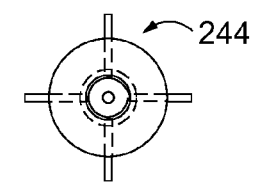
Fig. 2P

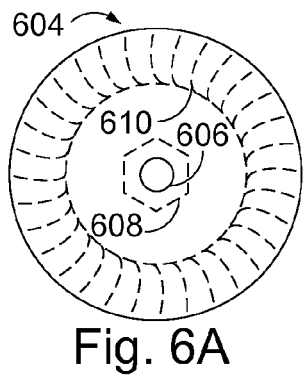
Fig. 6A
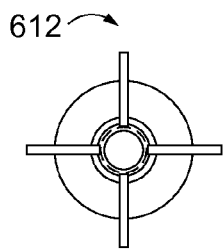
Fig. 6E
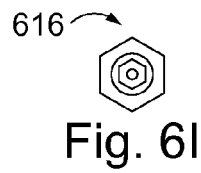
Fig. 6I
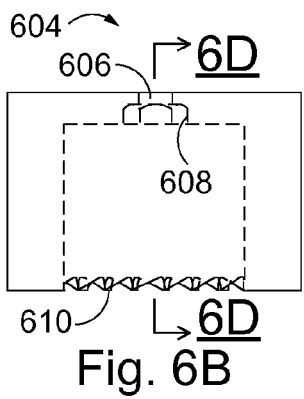
Fig. 6B
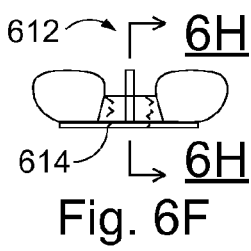
Fig. 6F
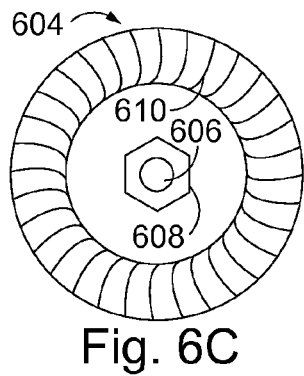
Fig. 6C
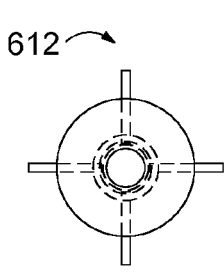
Fig. 6G
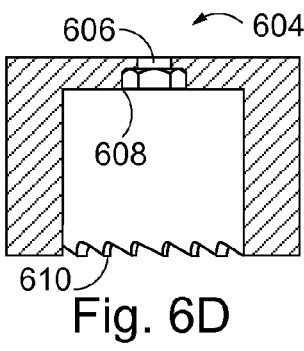
Fig. 6D
Fig. 6H
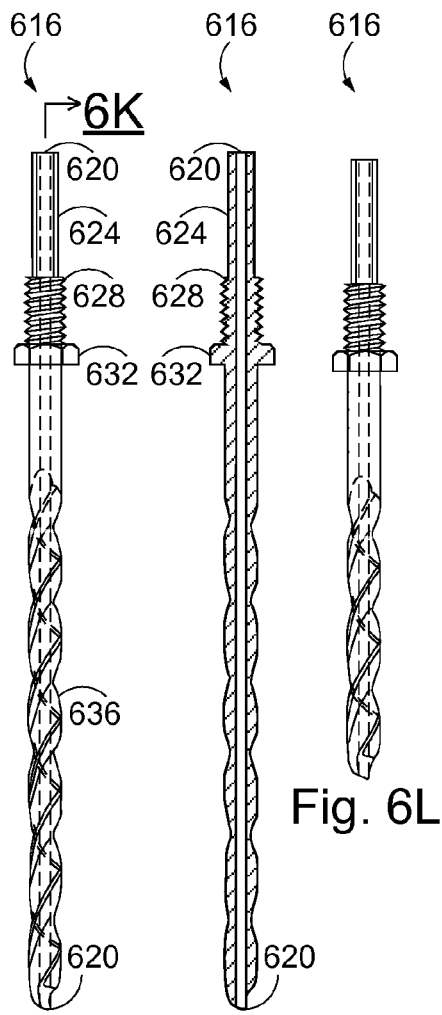
Fig. 6J  Fig. 6K
Fig. 6L
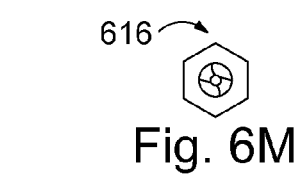
Fig. 6M

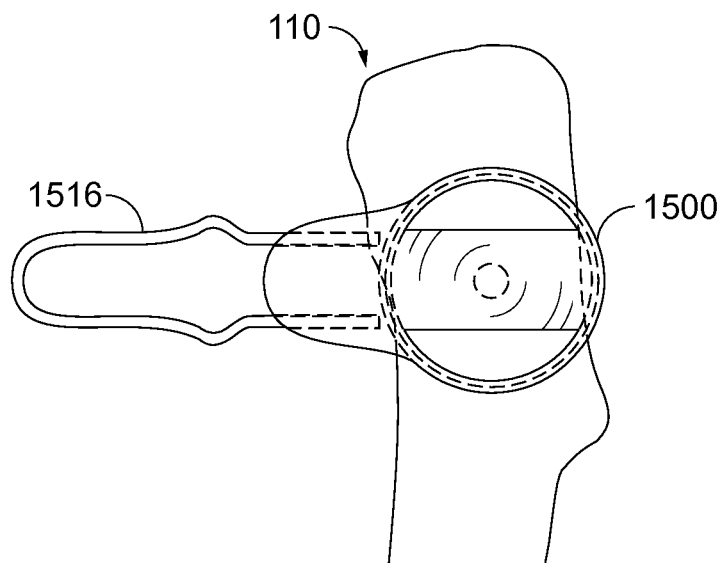
Fig. 16A
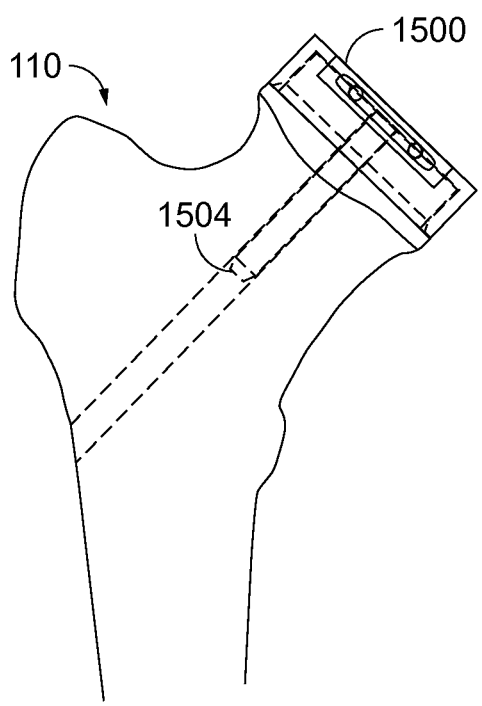 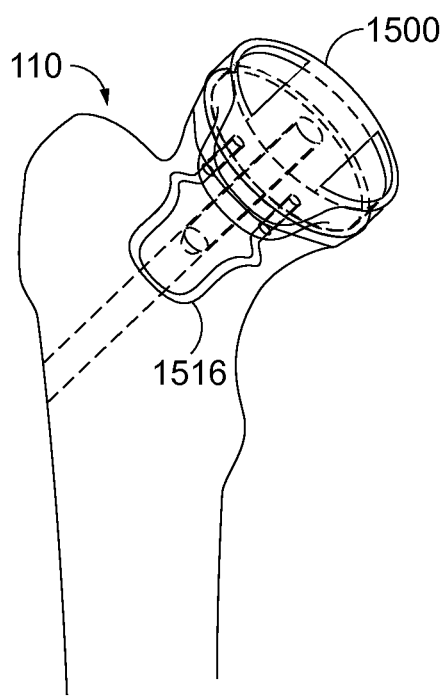
Fig. 16B  Fig. 16C

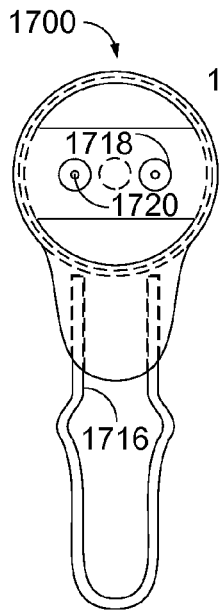
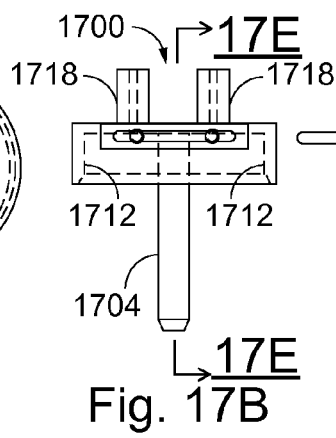
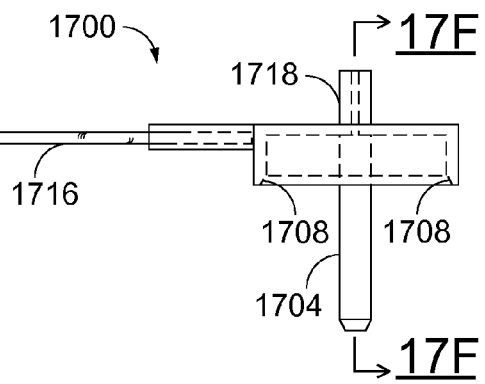
Fig. 17A
Fig. 17B
Fig. 17C
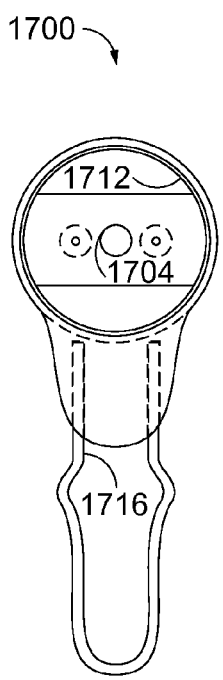
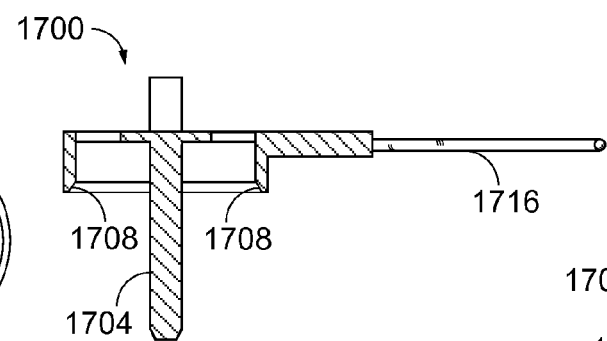
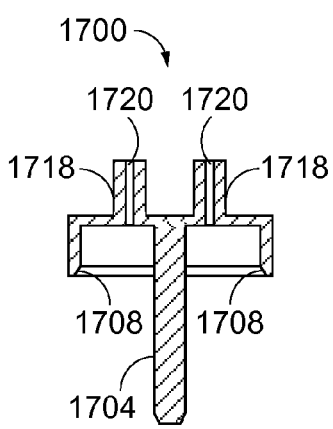
Fig. 17D
Fig. 17E
Fig. 17F

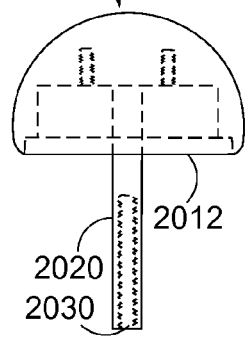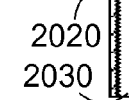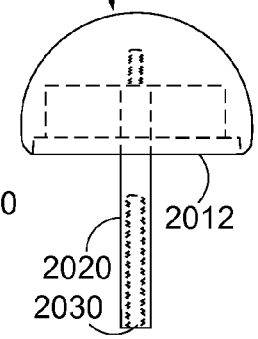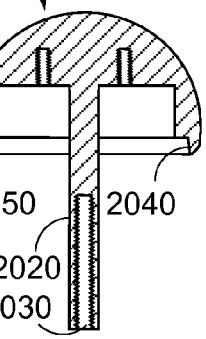
Fig. 20A  Fig. 20B  Fig. 20C  Fig. 20D
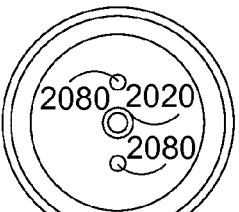
Fig. 20E
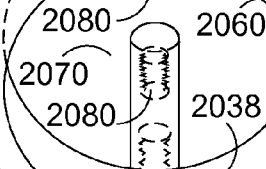
Fig. 20F
Fig. 20G

Fig. 21A
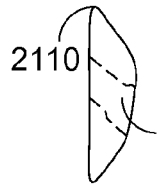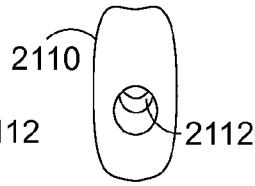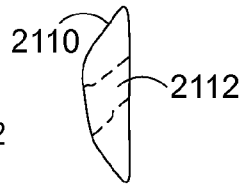
Fig. 21B  Fig. 21C  Fig. 21D
Fig. 21E
Fig. 21F
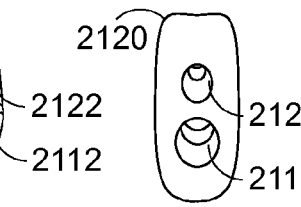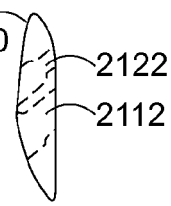
Fig. 21G  Fig. 21H  Fig. 21I
Fig. 21K
Fig. 21J
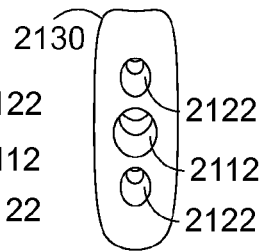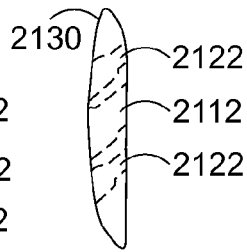
Fig. 21L  Fig. 21M  Fig. 21N
Fig. 21O

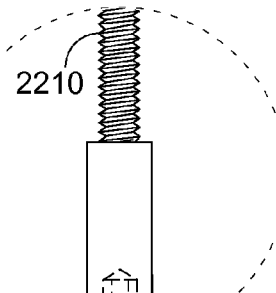
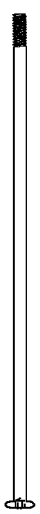
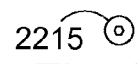
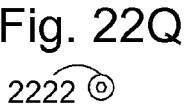
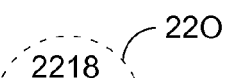
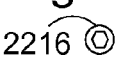
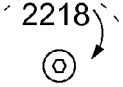

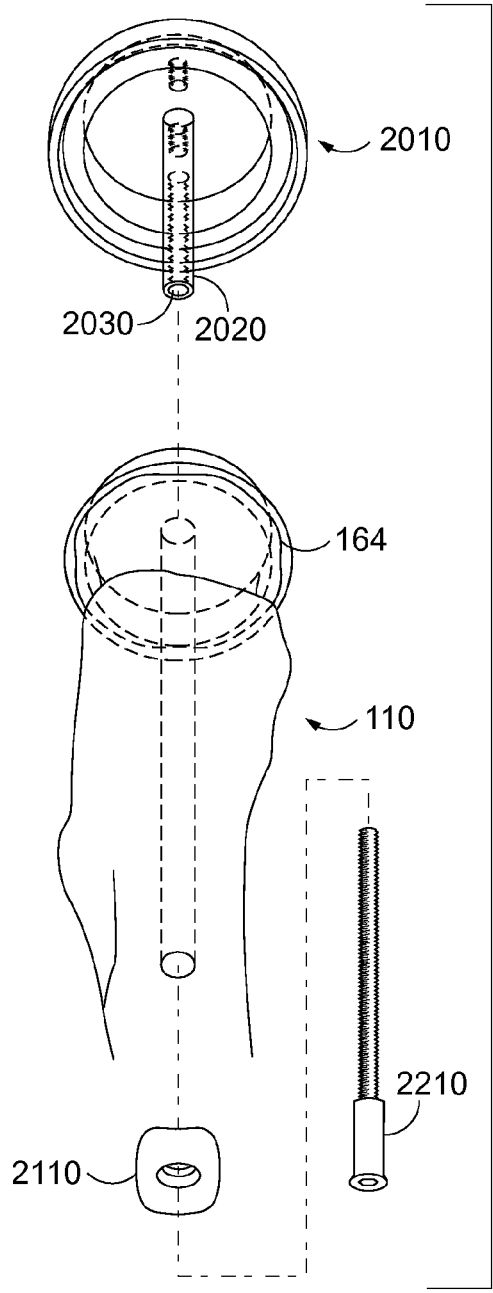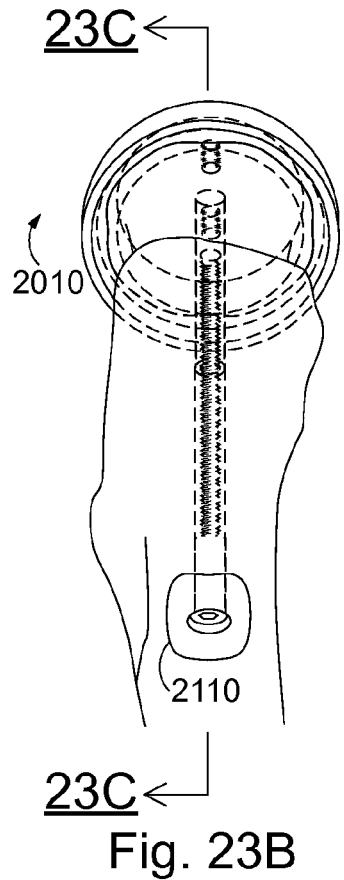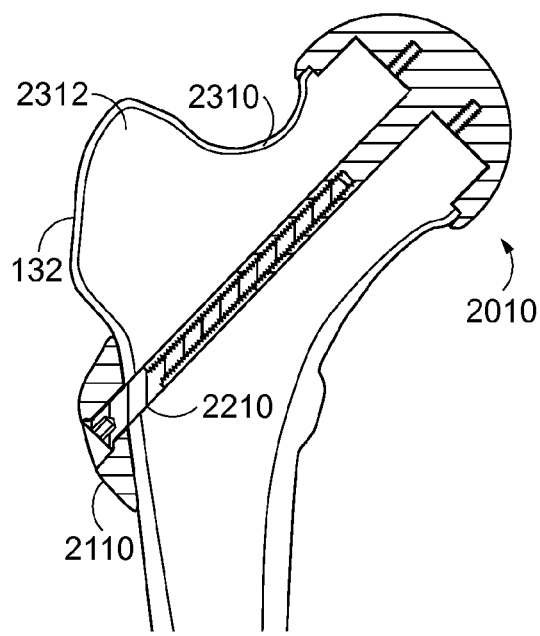
Fig. 23A
Fig. 23B
Fig. 23C

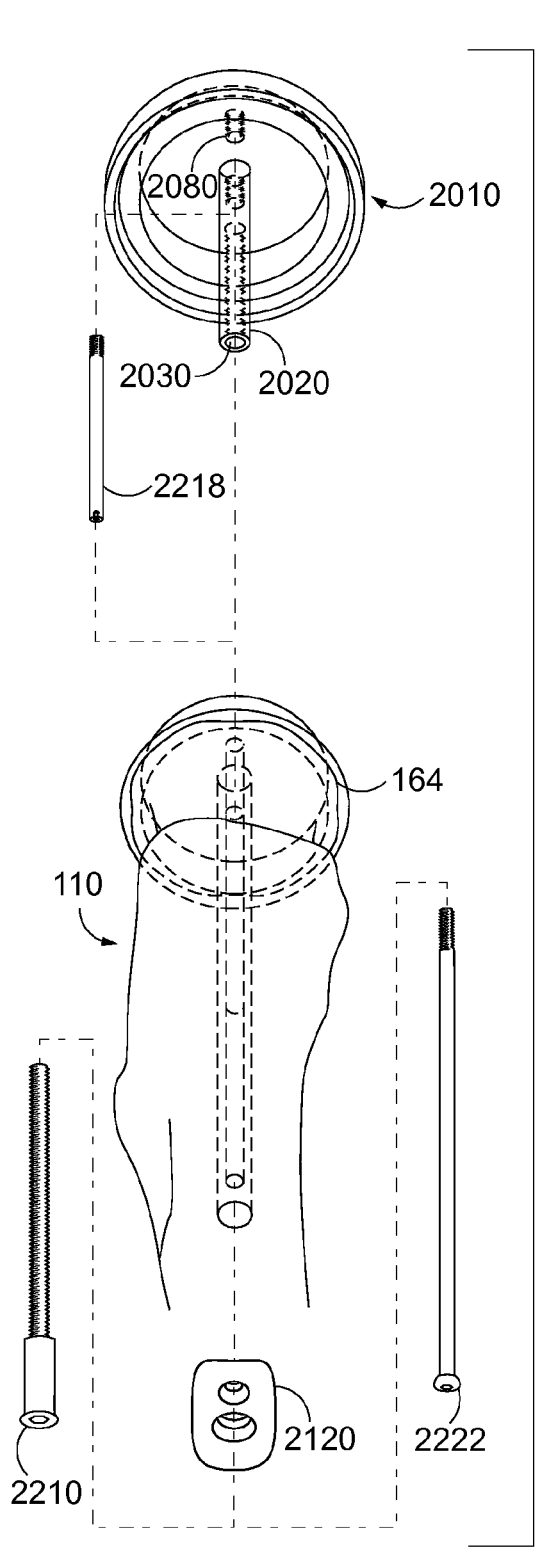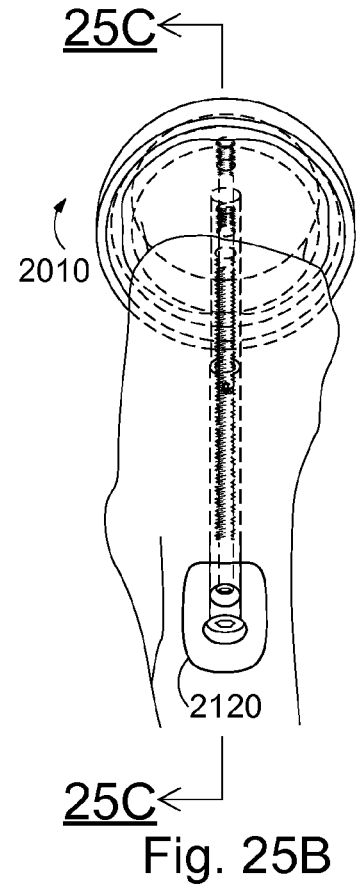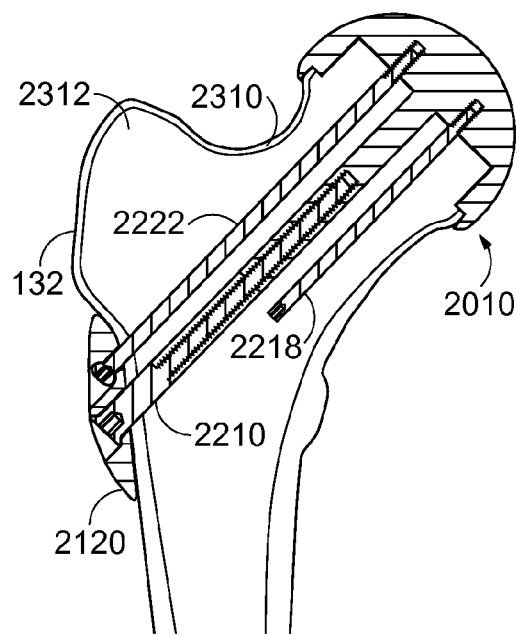
Fig. 25A
Fig. 25B
Fig. 25C

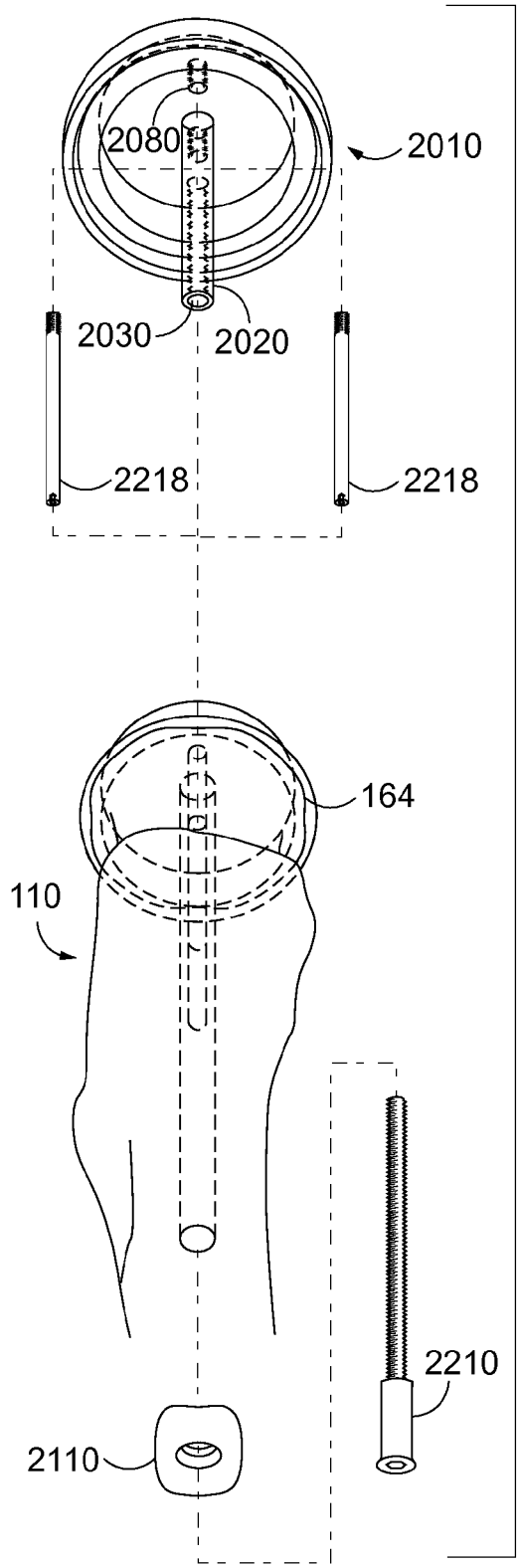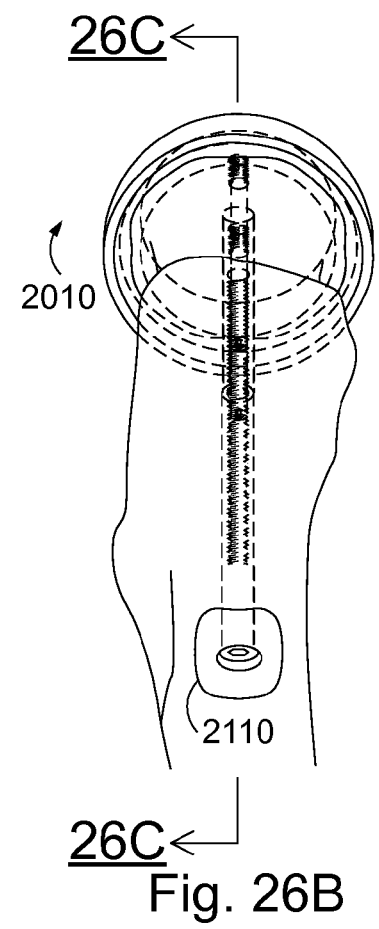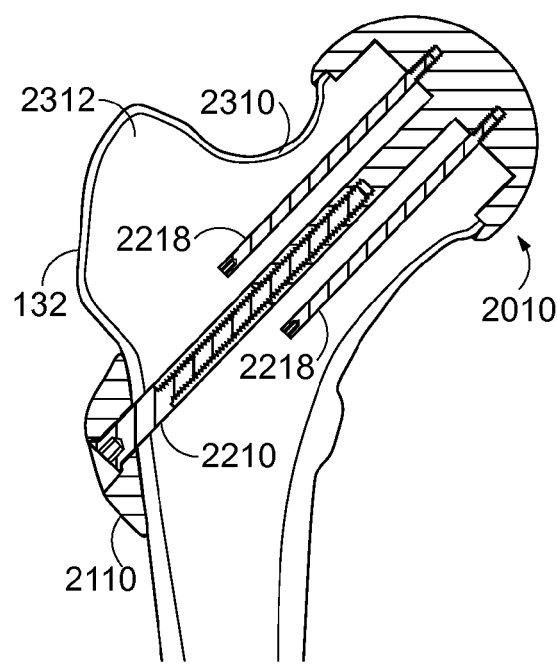
Fig. 26A
Fig. 26B
Fig. 26C

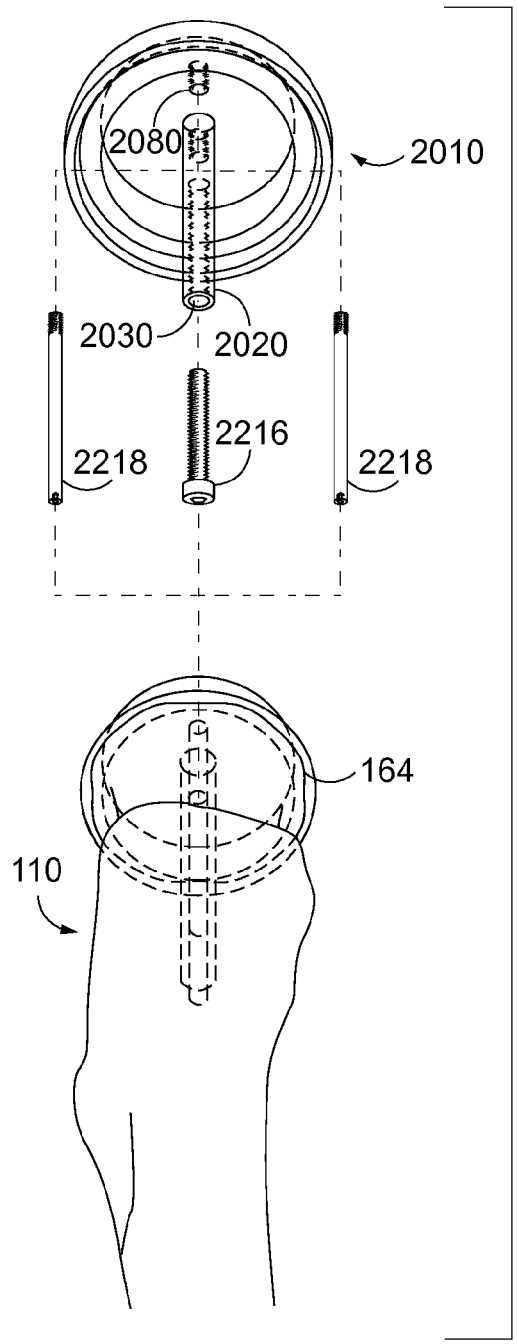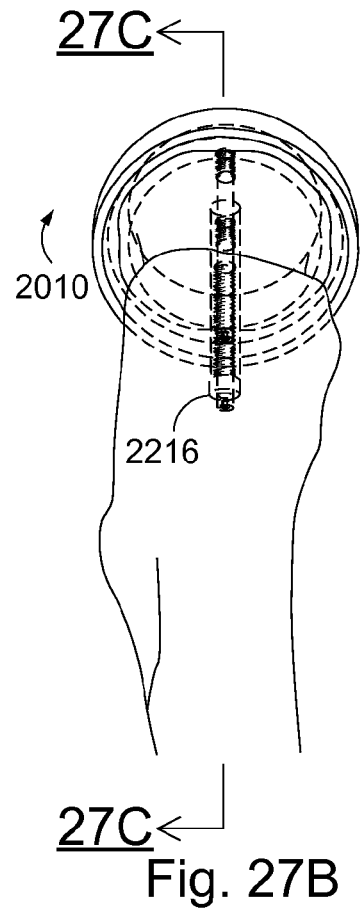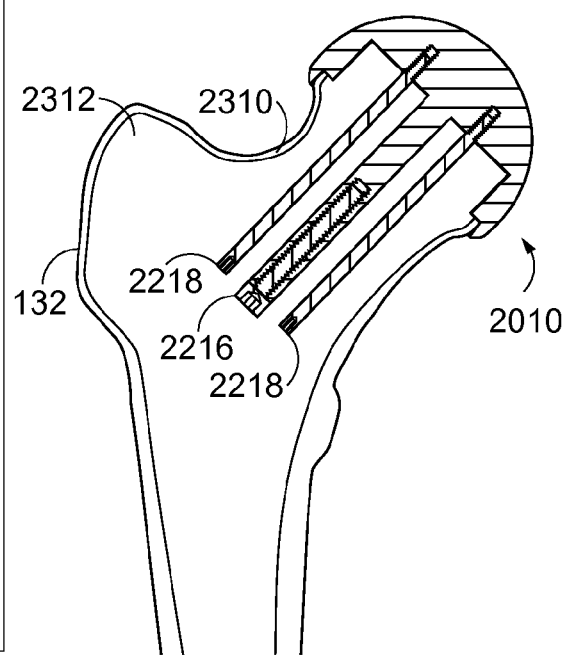
Fig. 27A
Fig. 27B
Fig. 27C

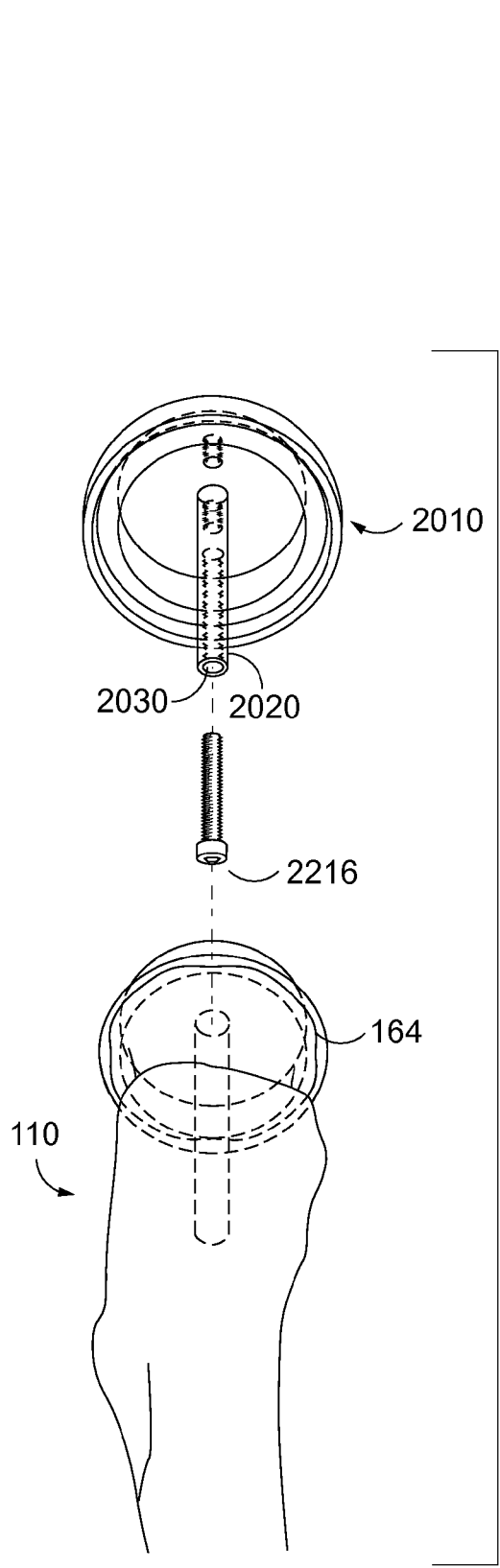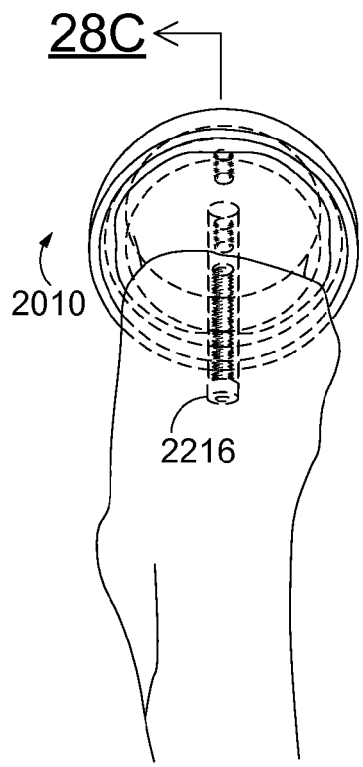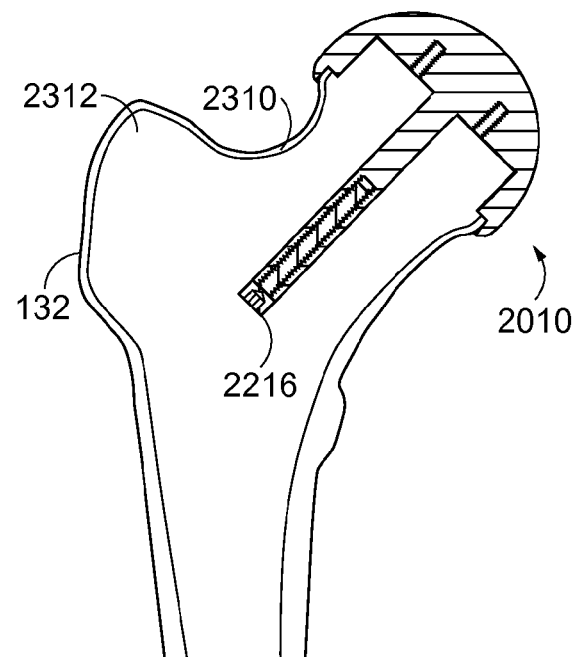
Fig. 28A
Fig. 28B
Fig. 28C

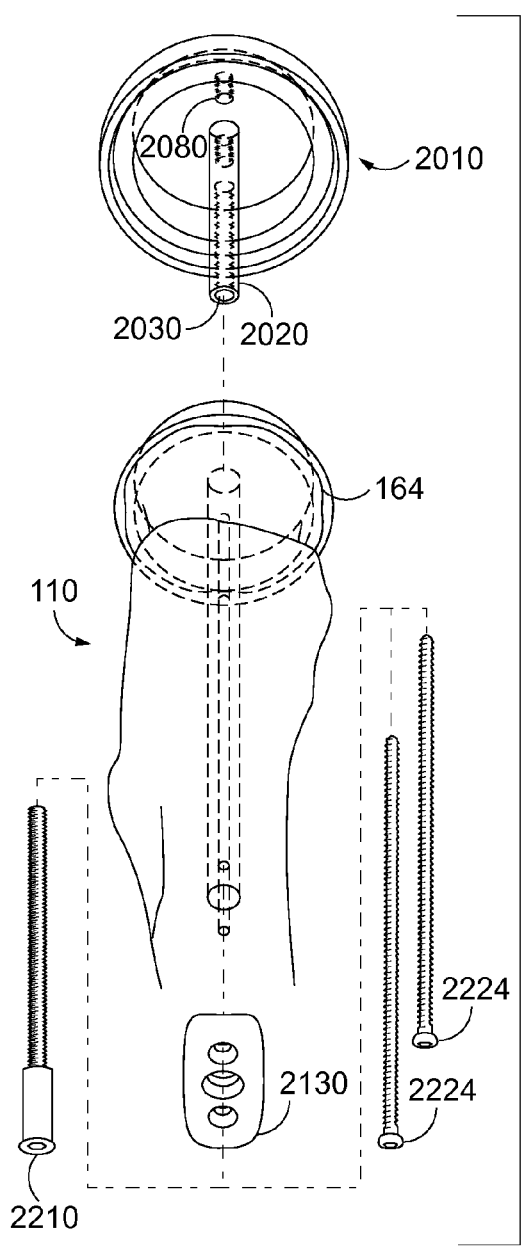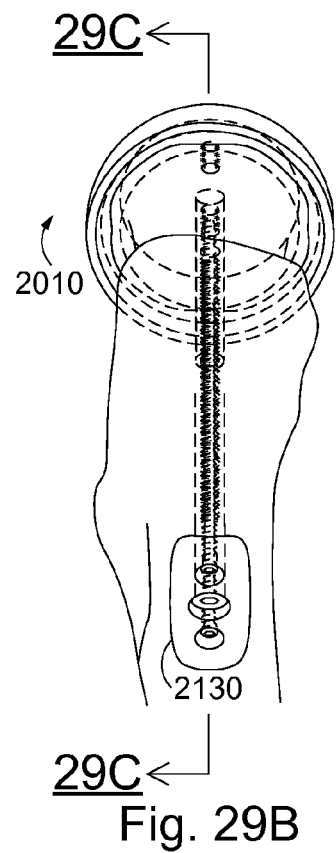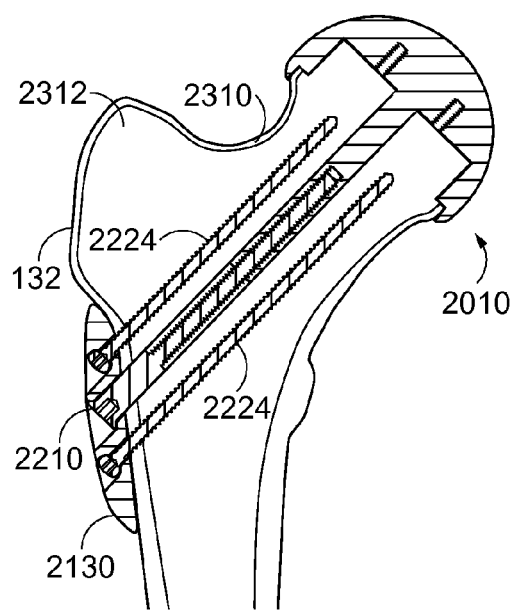
Fig. 29A
Fig. 29B
Fig. 29C

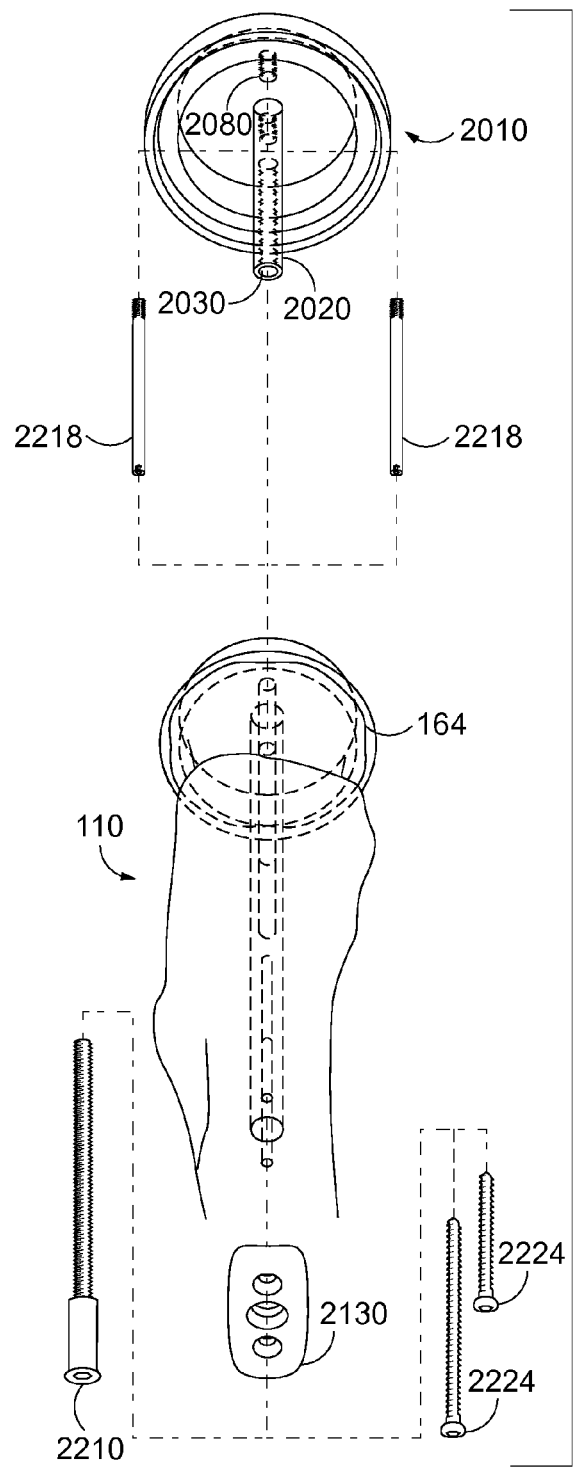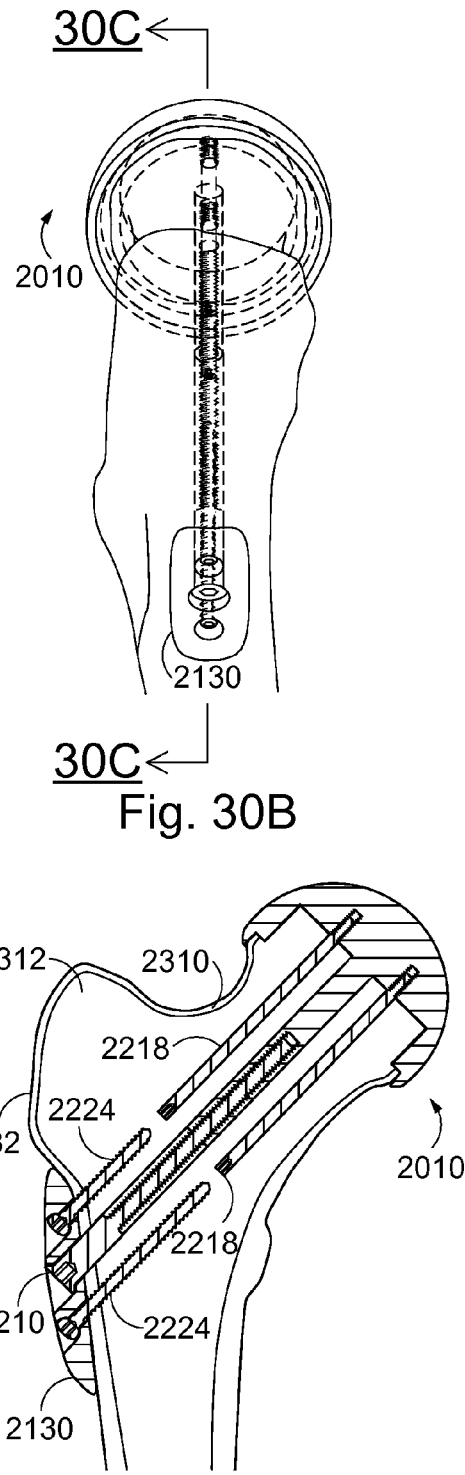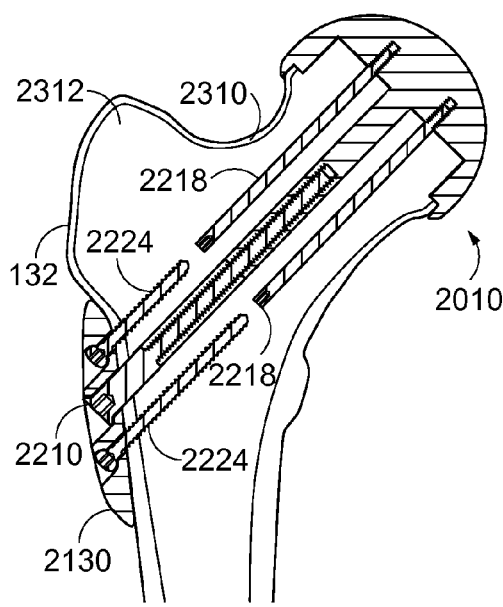
Fig. 30A
Fig. 30B
Fig. 30C

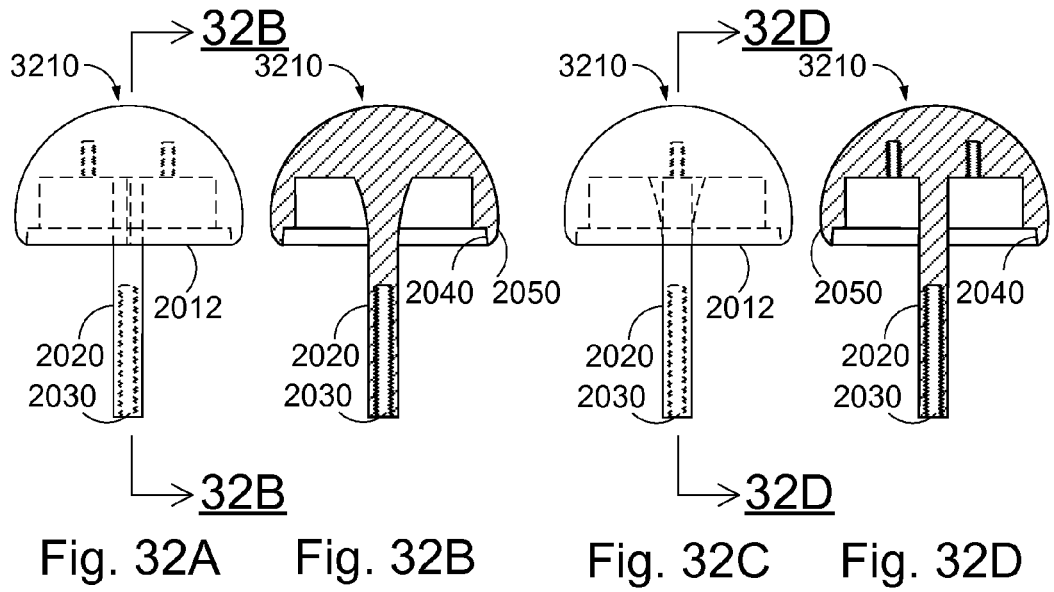
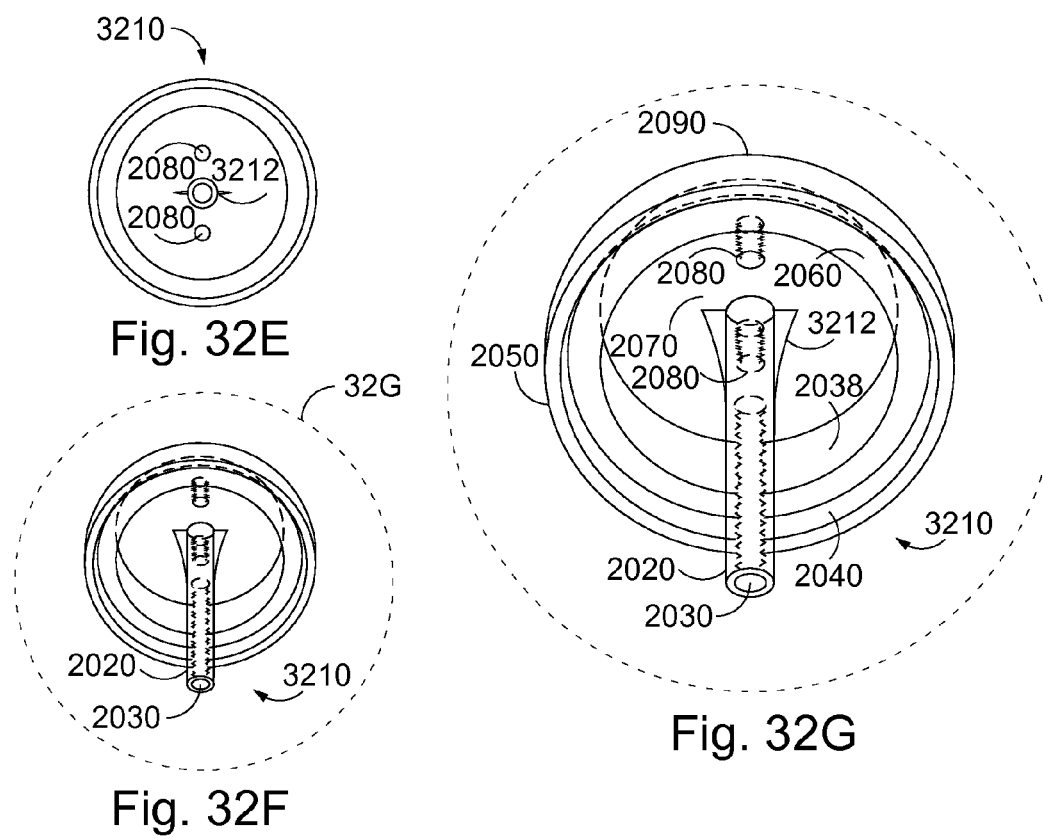
Fig. 32A  Fig. 32B  Fig. 32C  Fig. 32D
Fig. 32E
Fig. 32F
Fig. 32G

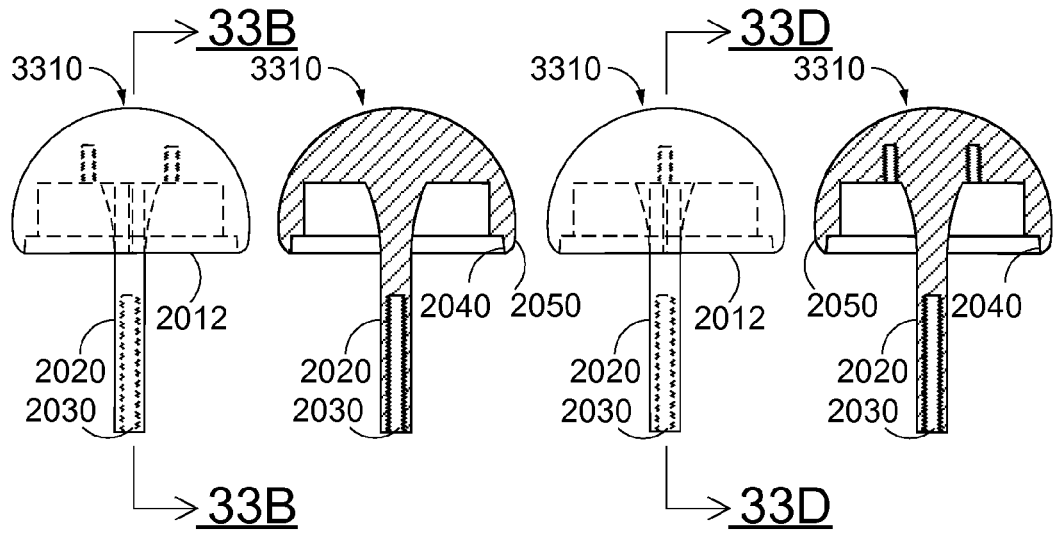
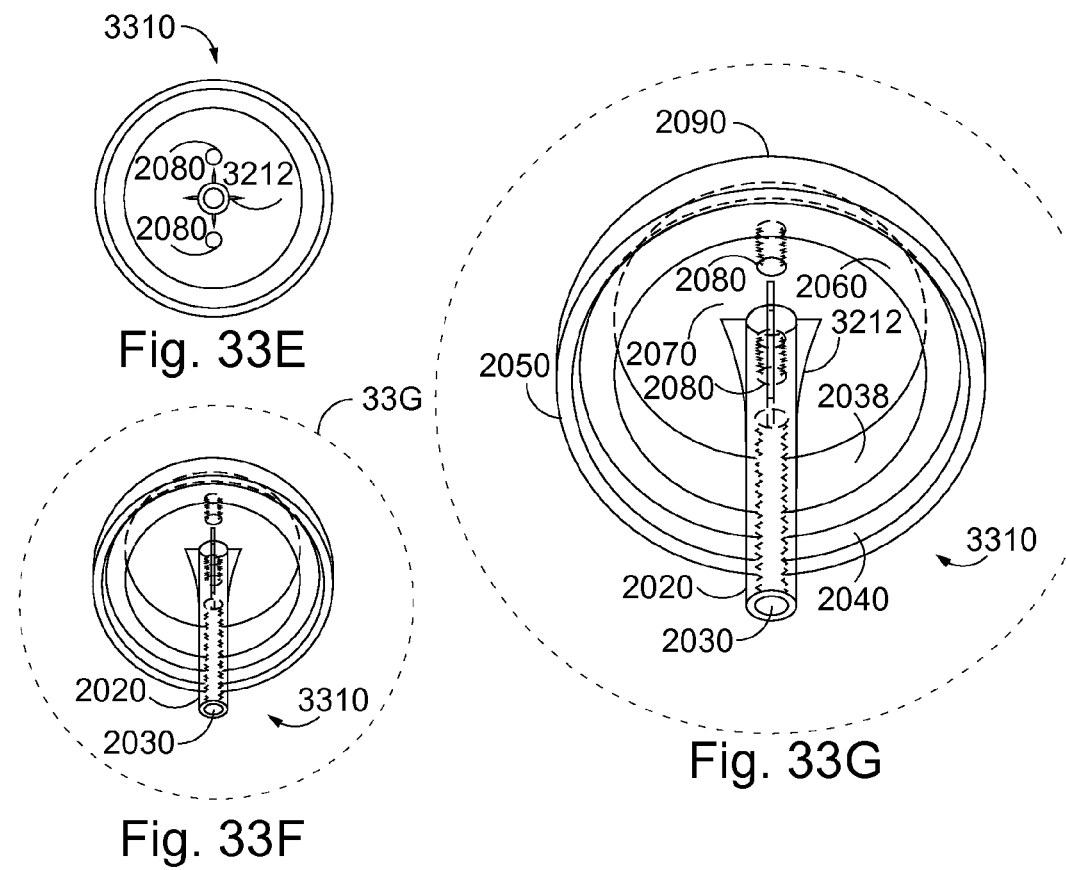
Fig. 33A   Fig. 33B   Fig. 33C   Fig. 33D
Fig. 33E
Fig. 33F
Fig. 33G

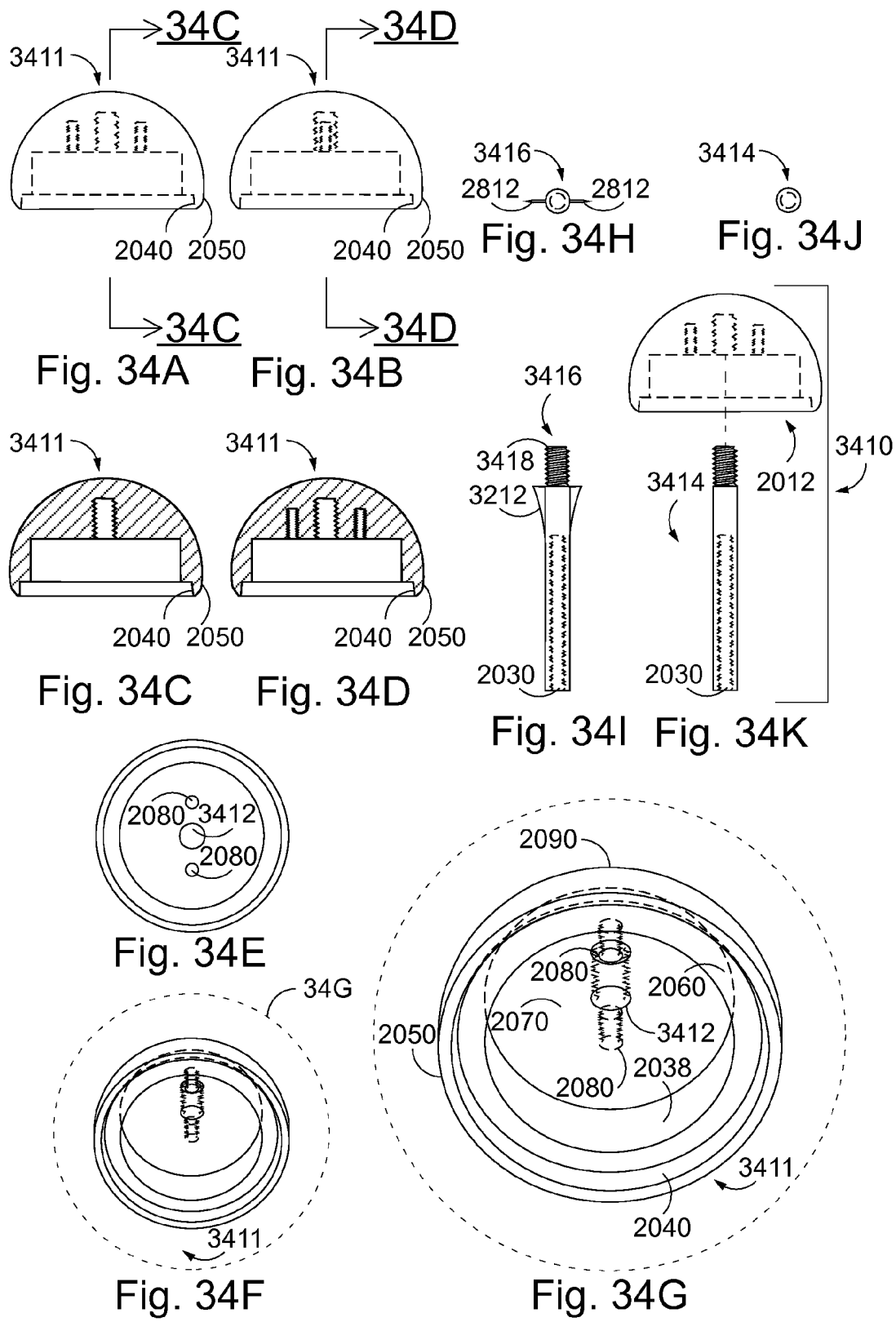

SYSTEM FOR MODULAR HIP RESURFACING

CROSS-REFERENCE TO RELATED APPLICATIONS

The present application claims the benefit of U.S. Provisional Patent Application Ser. No. 61/815,255, filed Apr. 23, 2013 and U.S. Provisional Patent Application Ser. No. 61/841,892, filed Jul. 1, 2013 by the present inventors, the entire contents of each of which is incorporated herein by reference thereto.

FIELD OF THE INVENTION

The present invention relates to hip resurfacing arthroplasty.

BACKGROUND INFORMATION

Hip joint disease is a common problem affecting large populations with multiple etiologies including osteoarthritis, avascular necrosis, post-traumatic arthritis and other hip joint pathologies. Over the course of the past century, many surgical techniques have been advocated in attempts to both provide pain relief and improve hip joint mechanics and patient function. Multiple techniques have been proposed and widely utilized over the years. Early techniques of joint replacement replaced the entire femoral head with a metallic implant, connected to a load-bearing femoral stem.

Hip Resurfacing Arthroplasty is a generally more conservative surgical technique that preserves more bone, including the femoral neck, since the surface of the femoral head is replaced using a hip resurfacing implant. The acetabulum is also resurfaced with implantation of an acetabular cup component. A common hip resurfacing femoral implant is illustrated as prior art in FIG. 1B.

Early Hip Resurfacing Arthoplasty is widely considered to have its roots in the work of John Charnley during the 1960's. More recently, Harlan Amstutz made further developments to hip resurfacing as illustrated in U.S. Pat. No. 4,123,806, showing a non-stemmed femoral hip resurfacing implant, and then in U.S. Pat. No. 6,156,069, showing a stemmed femoral hip resurfacing implant. A similar hip resurfacing system was developed by Derrick McMinn, an orthopedic surgeon from the West Midlands, UK. This system is known as the Birmingham Hip Resurfacing (BHR) system which uses a metal on metal design. Dr. McMinn subsequently developed the Birmingham Mid Head Resection (BMHR) implant, which is a modified version of the BHR system.

In all hip resurfacing systems, the femoral head needs to be prepared and shaped with a series of bone cuts. The Amstutz, BHR, and BMHR systems completely remove the dense, cortical bone of the femoral head leaving only the inner spongy, cancellous bone. In the Amstutz and BHR hip resurfacing implants, the upper, cap portion of the femoral implants seat onto the cancellous bone of the femoral head. The BMHR implant also does not utilize the femoral head cortex for implant support. This is a significant disadvantage of these implants as they do not gain additional peripheral stability from the strong and dense cortical bone of the femoral head. Bone preparation with the Amstutz, BHR, and BMHR systems include cylindrical reaming past the cartilage border, articular rim of the femoral head. This endangers the femoral neck as it may be notched during bone preparations from contact with the cylindrical reamer, which may then lead to the devastating complication of femoral neck fracture during subsequent load bearing.

Additionally, the Amstutz, BHR, and BMHR systems do not allow for additional threaded modular attachments for increasing fixation of the implant to the underlying bone. In the Amstutz, BHR, BMHR systems, bone cement is relied upon to secure the femoral implant to the underlying bone. While these implants are designed with porous surfaces allowing bony ingrowth, the implant is secured initially only with cement to the underlying bone. As the bony ingrowth takes time, bone cement is required for initial fixation of the device to the underlying bone of the femur. There are no additional fixation options for these implants in areas of poor bone quality. This is a another significant limitation as the strength of cancellous bone can be highly variable depending on local hip conditions including avascular necrosis, localized bone cysts and osteolysis. Soft cancellous bone can be encountered during surgery, but implant strength cannot be further increased with supplemental fixation. The BMHR system is designed to resect more of the cancellous bone of the femoral head, as compared to the BHR system, in order to attempt to address local bone deficiencies with use of an implant with a conical stem. However, this approach may remove healthy bone as a significant resection of femoral head bone is required during bone preparation for placement of the implant. The volume of bone resection required for the BMHR system is higher than that required for the BHR system. The Amstutz, BHR and BMHR designs also lack additional modular options for adding fixation. Thus, the Amstutz, BHR and BMHR hip resurfacing systems have limited flexibility to address bone deficiency.

Multiple surgical instruments are used to perform hip resurfacing arthroplasty. One such instrument is the alignment guide. A common example of an alignment guide used in hip resurfacing arthroplasty is the McMinn alignment guide from Smith & Nephew Orthopaedics Limited. Another such instrument is the cylindrical reamer, which is used to cut the bone of the femoral head, forming a cylindrical shape. A commonly used cylindrical reamer design for hip resurfacing arthroplasty is shown in U.S. Pat. No. 6,156,069. Following the cylindrical reaming procedure, a saw guide or cutoff guide is used to remove an additional small medial aspect of the bone of the femoral head.

SUMMARY

The modular hip resurfacing system according to an example embodiment of the present invention preserves a substantial collar of cortical bone, above the cartilage border, articular rim of the femoral head, and uses it for further implant support, as a periphery of the implant is partially mated to this strong, dense bone. Further, the modular hip resurfacing implant according to the present invention has threading at the base of its stem for modular attachments. This allows for the addition of a central screw, which can be used in combination with a femoral plate to significantly increase construct strength, when required.

Another benefit of the modular hip resurfacing implant according to an example embodiment of the present invention is additional threaded holes along the undersurface of the upper cap portion. These additional threaded holes provide for a wide range of fixation options, which can be used to further increase construct strength in the setting of localized bone deficiencies. Therefore, local cancellous bone deficiencies can be addressed in an individualized manner, depending on where the deficient cancellous bone is situated. The additional threaded holes on the undersurface of the upper cap portion of the modular hip resurfacing implant of the present invention greatly expand upon the fixation options available for the surgeon to address underlying bone deficiencies, and allow the use of additional screws and pegs for added fixation. In turn, these modular fixation options allow scalability for increasing implant strength, and provide durability and rotational stability during the lifecycle of the implant.

With respect to the tools used to perform hip resurfacing arthroplasty, there is a need for an alignment guide that ensures centralization of the guide pin within the femoral head, while also allowing for placement of the guide pin parallel to the femoral neck axis, as needed. There is also a need for an alignment guide that minimizes surgical access and exposure, and provides increased freedom for rotational adjustment. Further, there is a need for an alignment guide that does not involve manipulation of multiple adjustment joints for alternation of its orientation.

According to an example embodiment of the present invention, an alignment guide is provided that seats and secures only to the femoral head, and is located at a distance from the bone at the femoral head-neck junction. Such placement and fixation, ensures centralized insertion of guide pin within the femoral head, while also allowing placement of the guide pin parallel to the femoral neck axis, as needed. Once seated, it also allows for ample freedom of rotational adjustment.

There is also need for a cannulated cylindrical reamer that can protect the femoral neck from contact with the cylindrical reamer. Further, there is a need for a cannulated cylindrical reamer that can simultaneously drill a central bone channel while cutting away the peripheral bone of the femoral head to a predetermined latitudinal location. There is also a need for a cylindrical reamer that can be modularly adapted in order to drill multiple lengths of central bone channels.

According to an example embodiment of the present invention, a modular cannulated cylindrical reamer is provided that can cut away the peripheral bone of the femoral head to a predetermined latitudinal location about the femoral head without leaving a resultant bone sleeve, thereby forming a cylindrical shape, while leaving a collar of bone above the articular rim of the femoral head. Such a reamer reduces the risk of femoral neck notching. The modular cannulated cylindrical reamer of the present invention can simultaneously drill a central bone channel while cutting away the peripheral bone of the femoral head to a predetermined latitudinal location and can be modularly adapted to drill multiple bone channel lengths.

There is also a need for an improved saw guide to be used in hip resurfacing arthroplasty. According to an example embodiment of the present invention, a saw guide is provided that is manually seated, aided by multiple removable handles, upon a remaining collar of intact femoral head cortical bone to guide a surgical saw blade and proximal osteotomy to a precise height, further simplifying the process of performing the osteotomy. The saw guide has an option for placement of multiple removable handles to aid in seating and stabilizing the saw guide during use of a surgical saw.

According to an example embodiment of the present invention, a soft tissue protector is provided that allows for both shielding and retraction of soft tissues near the hip joint and is designed via a step-shaped design to accommodate simultaneous use of the soft tissue protector with the saw guide, while protecting soft tissue structures during use of a surgical saw. This can be advantageous during multiple stages of the procedure including cylindrical reaming and acetabular component placement.

According to an example embodiment of the present invention, a hip retractor is provided that is designed to seat onto a prepared femoral head with a post extending into the central bone channel. Such a retractor allows a surgeon to gain additional retraction after completion of cylindrical reaming, as required. It also helps shield the cancellous bone of the femoral head following cylindrical reaming, simultaneous drilling of the central bone channel, and proximal osteotomy completion.

According to an example embodiment of the present invention, an outer hole drill guide is provided that aids in the precise placement of guide pins for the subsequent drilling of outer holes for the modular hip resurfacing system and makes precise drilling of outer holes easier. Such a drill guide enables further modular attachments both above and below the central bone channel. It also preferably has a fixed handle to allow further manual stabilization during use.

BRIEF DESCRIPTION OF THE DRAWINGS

FIG. 2A is a top view illustrating an alignment guide for hip resurfacing, in accordance with one exemplary embodiment of the present invention.

FIG. 2B is a front view of the alignment guide shown in FIG. 2A.

FIG. 2C shows an enlarged front view of a section of the alignment guide, as indicated by the dashed circle in FIG. 2B.

FIG. 2D shows a cross-sectional left view of the alignment guide, as indicated by line 2D-2D in FIG. 2B.

FIG. 2E is a bottom view of the alignment guide shown in FIG. 2A.

FIG. 2F is a top view of a removable flat handle to aid placement of the alignment guide shown in FIG. 2A, in accordance with one exemplary embodiment of the present invention.

FIG. 2G is a rear view of the removable flat handle shown in FIG. 2F.

FIG. 2H is a front view of the removable flat handle shown in FIG. 2F.

FIG. 2I is a right view of the removable flat handle shown in FIG. 2F.

FIG. 2J is a rear view of an alignment pin to aid alignment of the alignment guide shown in FIG. 2A, in accordance with one exemplary embodiment of the present invention.

FIG. 2K is a front view of the alignment pin shown in FIG. 2J.

FIG. 2L is a right view of the alignment pin shown in FIG. 2J.

FIG. 2M is a top view of a cannulated guide pin screw for the alignment guide shown in FIG. 2A, in accordance with one exemplary embodiment of the present invention.

FIG. 2N is a front view of the cannulated guide pin screw shown in FIG. 2M.

FIG. 2O shows a cross-sectional left view of the cannulated guide pin screw shown in FIG. 2M, as indicated by line 2O-2O in FIG. 2N.

FIG. 2P is a bottom view of the cannulated guide pin screw shown in FIG. 2M.

FIG. 6A is a top view illustrating a cylindrical reamer for hip resurfacing, in accordance with one exemplary embodiment of the present invention.

FIG. 6B is a front view of the cylindrical reamer shown in FIG. 6A.

FIG. 6C is a bottom view of the cylindrical reamer shown in FIG. 6A.

FIG. 6D shows a cross-sectional left view of a cylindrical reamer shown in FIG. 6A, as indicated by line 6D-6D in FIG. 6B.

FIG. 6E is a top view illustrating a cylindrical reamer fastener, in accordance with one exemplary embodiment of the present invention.

FIG. 6F is a front view of the cylindrical reamer fastener shown in FIG. 6E.

FIG. 6G is a bottom view of the cylindrical reamer fastener shown in FIG. 6E.

FIG. 6H shows a cross-sectional left view of the cylindrical reamer fastener shown in FIG. 6E, as indicated by line 6H-6H in FIG. 6F.

FIG. 6I is a top view illustrating a cannulated cylindrical reamer drill base, in accordance with one exemplary embodiment of the present invention.

FIG. 6J is a front view of the cannulated cylindrical reamer drill base shown in FIG. 6I.

FIG. 6K shows a cross-sectional left view of the cannulated cylindrical reamer drill base shown in FIG. 6I, as indicated by line 6K-6K in FIG. 6J.

FIG. 6L is an front view of a cannulated cylindrical reamer drill base for a decreased resultant drilling depth according to an alternative exemplary embodiment of the present invention.

FIG. 6M is a bottom view of the cannulated cylindrical reamer drill base shown in FIG. 6L.

FIG. 16A is a top view of the seated hip retractor, following the osteotomies and central bone channel creation according to the present invention.

FIG. 16B is a front view further illustrating the seated hip retractor according to the present invention.

FIG. 16C is a front perspective view, further illustrating the seated hip retractor according to the present invention.

FIG. 17A is a top view illustrating an outer hole drill guide, in accordance with one exemplary embodiment of the present invention.

FIG. 17B is a front view of the outer hole drill guide shown in FIG. 17A.

FIG. 17C is a right view of the outer hole drill guide shown in FIG. 17A.

FIG. 17D is a bottom view of the outer hole drill guide shown in FIG. 17A.

FIG. 17E shows a cross-sectional left view of the outer hole drill guide shown in FIG. 17A, as indicated by line 17E-17E in FIG. 17B.

FIG. 17F shows a cross-sectional front view of the outer hole drill guide shown in FIG. 17A, as indicated by line 17F-17F in FIG. 17C.

FIG. 20A is a front view illustrating a modular hip resurfacing implant with a fixed central stem, in accordance with one exemplary embodiment of the present invention.

FIG. 20B is a cross-sectional left view of the modular hip resurfacing implant shown in FIG. 20A, as indicated by linen 20B-20B in FIG. 20A.

FIG. 20C is a right view of the modular hip resurfacing implant shown in FIG. 20A.

FIG. 20D is a cross-sectional front view of the modular hip resurfacing implant shown in FIG. 20A, as indicated by line 20D-20D in FIG. 20C.

FIG. 20E is a bottom view of the modular hip resurfacing implant shown in FIG. 20A.

FIG. 20F is a bottom perspective view of the modular hip resurfacing implant shown in FIG. 20A.

FIG. 20G is an enlarged bottom perspective view of the modular hip resurfacing implant shown in FIG. 20A in detail, as indicated by the dashed circle around FIG. 20F.

FIG. 21A is a top view of a one-hole plate according to one exemplary embodiment of the present invention.

FIG. 21B is a left view further illustrating the one-hole plate having a central hole shown in FIG. 21A.

FIG. 21C is a front view of the one-hole plate shown in FIG. 21A.

FIG. 21D is a right view of the one-hole plate shown in FIG. 21A.

FIG. 21E is a bottom view of the one-hole plate shown in FIG. 21A.

FIG. 21F is a top view of a two-hole plate according to one exemplary embodiment of the present invention.

FIG. 21G is a left view further illustrating the two-hole plate having a central hole and, above, an outer hole shown in FIG. 21F.

FIG. 21H is a front view of the two-hole plate shown in FIG. 21F.

FIG. 21I is a right view of the two-hole plate shown in FIG. 21F.

FIG. 21J is a bottom view of the two-hole plate shown in FIG. 21F.

FIG. 21K is a top view of a three-hole plate according to one exemplary embodiment of the present invention.

FIG. 21L is a left view further illustrating the three-hole plate having a central hole and two outer holes shown in FIG. 21K.

FIG. 21M is a front view of the three-hole plate shown in FIG. 21K.

FIG. 21N is a right view of the three-hole plate shown in FIG. 21K.

FIG. 21O is a bottom view of the three-hole plate shown in FIG. 21K.

FIG. 22A is a top view of a central screw according to one exemplary embodiment of the present invention.

FIG. 22B is a front view of the central screw shown in FIG. 22A.

FIG. 22C is a bottom view of the central screw shown in FIG. 22A.

FIG. 22D is an enlarged top view of the central screw shown in FIG. 22A in detail, as indicated by the dashed circle around FIG. 22A.

FIG. 22E is an enlarged front view of the lower aspect of the central screw shown in FIG. 22A in detail, as indicated by the dashed circle in FIG. 22B.

FIG. 22F is an enlarged bottom view of the central screw shown in FIG. 22A in detail, as indicated by the dashed circle around FIG. 22C.

FIG. 22G is a front view of an independent central screw according to one exemplary embodiment of the present invention.

FIG. 22H is a bottom view of the independent central screw shown in FIG. 22G.

FIG. 22I is a front view of an independent outer screw according to one exemplary embodiment of the present invention.

FIG. 22J is a bottom view of the independent outer screw shown in FIG. 22I.

FIG. 22K is a front view of a threaded central cap according to one exemplary embodiment of the present invention.

FIG. 22L is a bottom view of the threaded central cap shown in FIG. 22K.

FIG. 22M is a front view of an outer peg according to one exemplary embodiment of the present invention.

FIG. 22N is a bottom view of the outer peg shown in FIG. 22M.

FIG. 22O is an enlarged front view of the upper aspect of the outer peg screw shown in FIG. 22M in detail, as indicated by the dashed circle in FIG. 22M.

FIG. 22P is an enlarged bottom view of the outer peg shown in FIG. 22M in detail, as indicated by the dashed circle around FIG. 22N.

FIG. 22Q is a front view of an outer screw according to one exemplary embodiment of the present invention.

FIG. 22R is a bottom view of the outer screw shown in FIG. 22Q.

FIG. 22S is a front view of a cortical screw according to one exemplary embodiment of the present invention.

FIG. 22T is a bottom view of the cortical screw shown in FIG. 22S.

FIG. 23A is an exploded bottom perspective view, following associated bone cuts, illustrating placement of a modular hip resurfacing implant, one-hole plate, and a central screw, in accordance with one exemplary modular configuration of the present invention.

FIG. 23B is a bottom perspective view following placement of the modular hip resurfacing implant, one-hole plate, and a central screw shown in FIG. 23A.

FIG. 23C is a cross-sectional right view, as indicated by line 23C-23C in FIG. 23B, following placement of the modular hip resurfacing implant, one-hole plate, and a central screw shown in FIG. 23A.

Figure 24A:
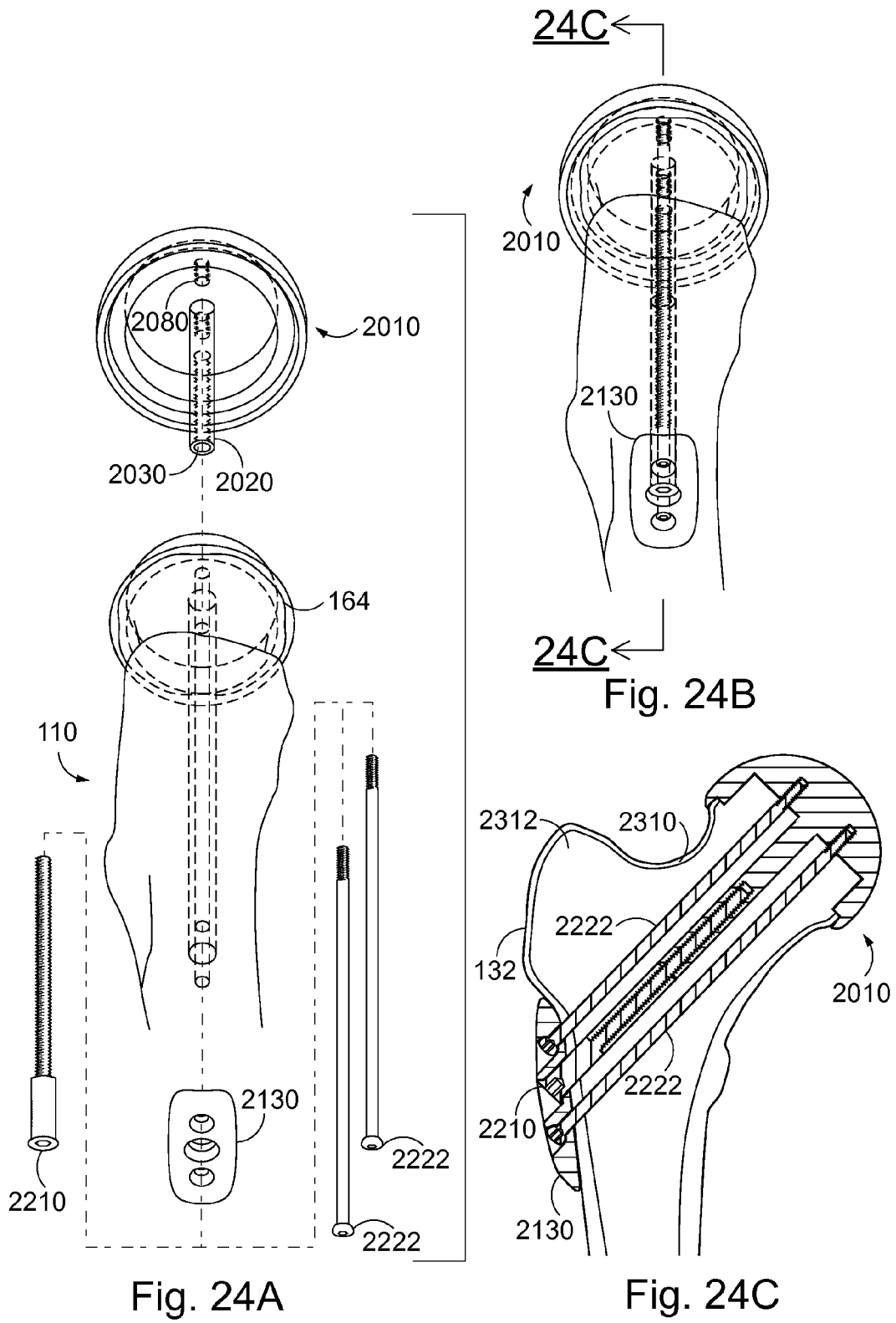

FIG. 24A is an exploded bottom perspective view, following associated bone cuts, illustrating placement of the modular hip resurfacing implant, three-hole plate, two outer screws, and a central screw, in accordance with another exemplary modular configuration of the present invention.

Figure 24B:
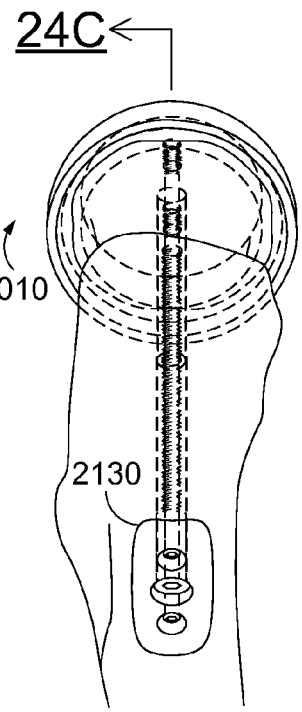

FIG. 24B is a bottom perspective view following placement of the modular hip resurfacing implant, three-hole plate, two outer screws, and a central screw shown in FIG. 24A.

Figure 24C:
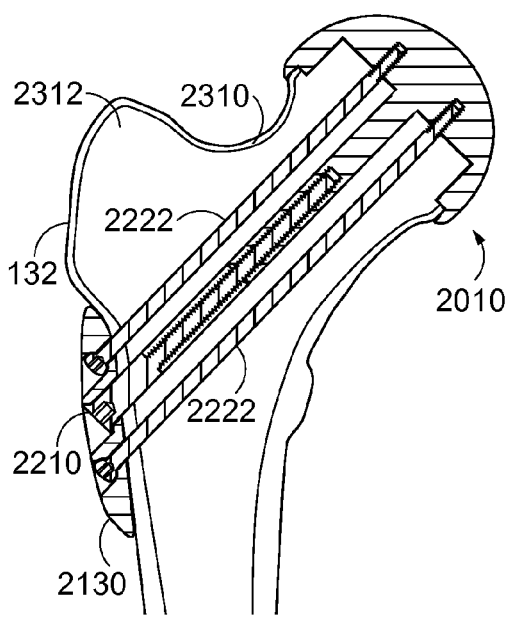

FIG. 24C is a cross-sectional right view, as indicated by line 24C-24C in FIG. 24B, following placement of the modular hip resurfacing implant, three-hole plate, two outer screws, and a central screw shown in FIG. 24A.

FIG. 25A is an exploded bottom perspective view, following associated bone cuts, illustrating placement of the modular hip resurfacing implant, an outer peg, two-hole plate, an outer screw and a central screw, in accordance with another exemplary modular configuration of the present invention.

FIG. 25B is a bottom perspective view following placement of the modular hip resurfacing implant, an outer peg, two-hole plate, outer screw, and a central screw shown in FIG. 25A.

FIG. 25C is a cross-sectional right view, as indicated by line 25C-25C in FIG. 25B, following placement of the modular hip resurfacing implant, outer peg, two-hole plate, outer screw, and a central screw shown in FIG. 25A.

FIG. 26A is an exploded bottom perspective view, following associated bone cuts, illustrating placement of the modular hip resurfacing implant, two outer pegs, one-hole plate and a central screw, in accordance with another exemplary modular configuration of the present invention.

FIG. 26B is a bottom perspective view following placement of the modular hip resurfacing implant, two outer pegs, one-hole plate, and a central screw shown in FIG. 26A.

FIG. 26C is a cross-sectional right view, as indicated by line 26C-26C in FIG. 26B, following placement of the modular hip resurfacing implant, two outer pegs, one-hole plate, and a central screw shown in FIG. 26A.

FIG. 27A is an exploded bottom perspective view, following associated bone cuts, illustrating placement of the modular hip resurfacing implant, two outer pegs, and a threaded central cap, in accordance with another exemplary modular configuration of the present invention.

FIG. 27B is a bottom perspective view following placement of the modular hip resurfacing implant, two outer pegs, and the threaded central cap shown in FIG. 27A.

FIG. 27C is a cross-sectional right view, as indicated by line 27C-27C in FIG. 27B, following placement of the modular hip resurfacing implant, two outer pegs, and the threaded central cap shown in FIG. 27A.

FIG. 28A is an exploded bottom perspective view, following associated bone cuts, illustrating placement of the modular hip resurfacing implant and the threaded central cap, in accordance with another exemplary modular configuration of the present invention.

FIG. 28B is a bottom perspective view following placement of the modular hip resurfacing implant, bone cement, and the threaded central cap shown in FIG. 28A.

FIG. 28C is a cross-sectional right view, as indicated by line 28C-28C in FIG. 28B, from anterior following placement of the modular hip resurfacing implant, bone cement, and the threaded central cap shown in FIG. 28A.

FIG. 29A is an exploded bottom perspective view, following associated bone cuts, illustrating placement of the modular hip resurfacing implant, three-hole plate, two cortical screws and the central screw, in accordance with another exemplary modular configuration of the present invention.

FIG. 29B is a bottom perspective view following placement of the modular hip resurfacing implant, three-hole plate, two cortical screws, and the central screw shown in FIG. 29A.

FIG. 29C is a cross-sectional right view, as indicated by line 29C-29C in FIG. 29B, following placement of the modular hip resurfacing implant, three-hole plate, two cortical screws, and the central screw shown in FIG. 29A.

FIG. 30A is an exploded bottom perspective view, following associated bone cuts, illustrating placement of the modular hip resurfacing implant, two outer pegs, three-hole plate, two cortical screws, and the central screw, in accordance with another exemplary modular configuration of the present invention.

FIG. 30B is a bottom perspective view following placement of the modular hip resurfacing implant, two outer pegs, three-hole plate, two cortical screws, and the central screw shown in FIG. 30A.

FIG. 30C is a cross-sectional right view, as indicated by line 30C-30C in FIG. 30B, following placement of the modular hip resurfacing implant, two outer pegs, three-hole plate, two cortical screws, and the central screw shown in FIG. 30A.

Figure 31A:
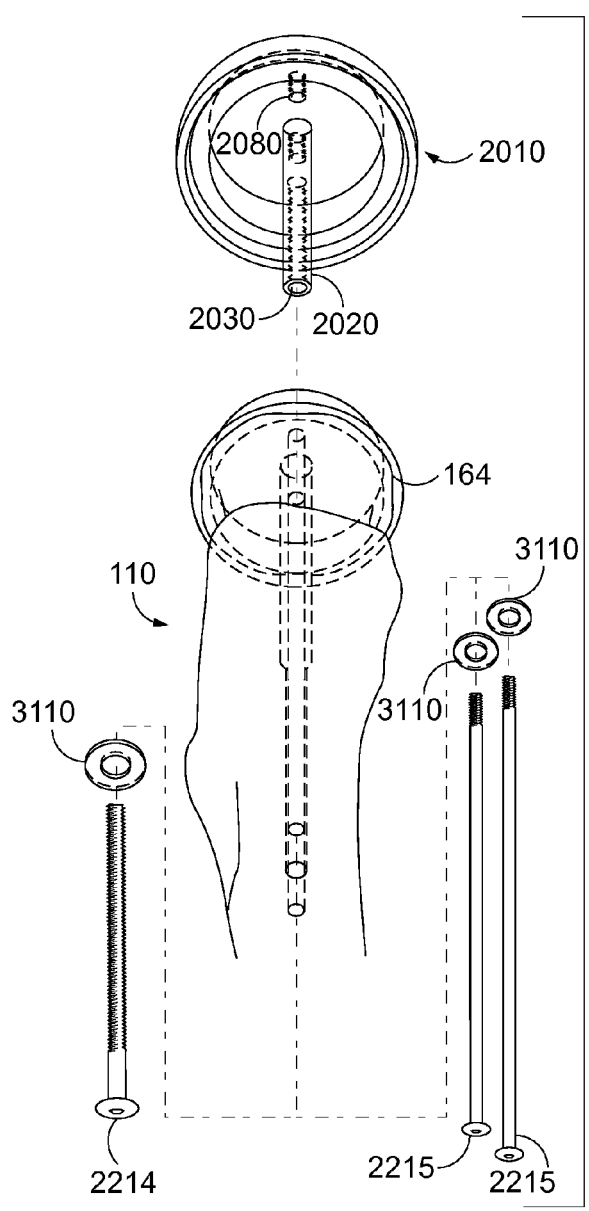

FIG. 31A is an exploded bottom perspective view, following associated bone cuts, illustrating placement of the modular hip resurfacing implant, an independent central screw with a washer, and two independent outer screws with washers, in accordance with another exemplary modular configuration of the present invention.

Figure 31B:
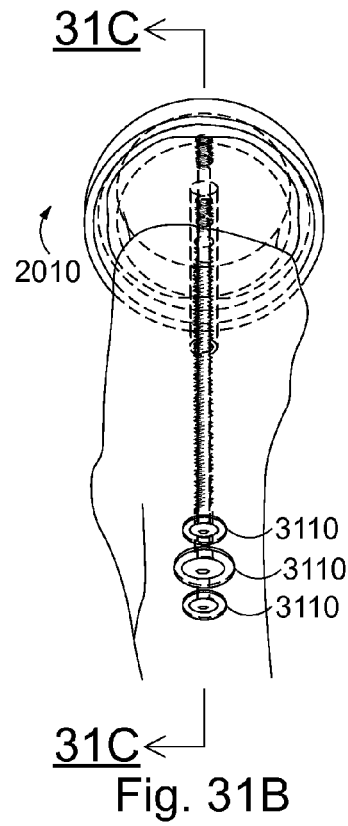

FIG. 31B is a bottom perspective view following placement of the modular hip resurfacing implant, an independent central screw with a washer, and two independent outer screws with washers shown in FIG. 31A.

Figure 31C:
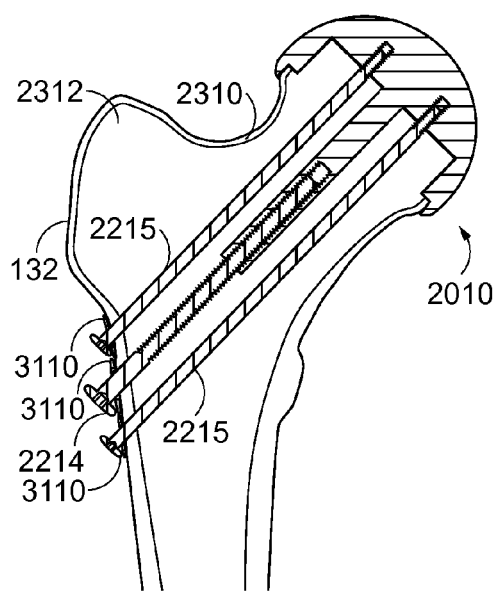

FIG. 31C is a cross-sectional right view, as indicated by line 31C-31C in FIG. 31B, following placement of the modular hip resurfacing implant, an independent central screw with a washer, and two independent outer screws with washers shown in FIG. 31A.

FIG. 32A is a front view illustrating a two-rib-modular hip resurfacing implant with a fixed central stem, in accordance with another exemplary embodiment of the modular hip resurfacing implant of the present invention.

FIG. 32B is a cross-sectional left view of the two-rib-modular hip resurfacing implant shown in FIG. 32A, as indicated by line 32B-32B in FIG. 32A.

FIG. 32C is a right view of the two-rib-modular hip resurfacing implant shown in FIG. 32A.

FIG. 32D is a cross-sectional front view of the two-rib-modular hip resurfacing implant shown in FIG. 32A, as indicated by line 32D-32D in FIG. 32C.

FIG. 32E is a bottom view of the two-rib-modular hip resurfacing implant shown in FIG. 32A.

FIG. 32F is a bottom perspective view of the two-rib-modular hip resurfacing implant shown in FIG. 32A.

FIG. 32G is an enlarged bottom perspective view of the two-rib-modular hip resurfacing implant shown in FIG. 32A in detail, as indicated by the dashed circle around FIG. 32F.

FIG. 33A is a front view illustrating a four-rib-modular hip resurfacing implant with a fixed central stem, in accordance with another exemplary embodiment of the modular hip resurfacing implant of the present invention.

FIG. 33B is a cross-sectional left view of the four-rib-modular hip resurfacing implant shown in FIG. 33A, as indicated by line 33B-33B in FIG. 33A.

FIG. 33C is a right view of the four-rib-modular hip resurfacing implant shown in FIG. 33A.

FIG. 33D is a cross-sectional front view of the four-rib-modular hip resurfacing implant shown in FIG. 33A, as indicated by linen 33D-33D in FIG. 33C.

FIG. 33E is a bottom view of the four-rib-modular hip resurfacing implant shown in FIG. 33A.

FIG. 33F is a bottom perspective view of the four-rib-modular hip resurfacing implant shown in FIG. 33A.

FIG. 33G is an enlarged bottom perspective view of the four-rib-modular hip resurfacing implant shown in FIG. 33A in detail, as indicated by the dashed circle around FIG. 33F.

FIG. 34A is a front view illustrating a cap portion of a modular stemmed implant, which is a component of a detachable stem-modular hip resurfacing implant, in accordance with another exemplary embodiment of the modular hip resurfacing implant of the present invention.

FIG. 34B is a right view of the cap portion of the modular stemmed implant shown in FIG. 34A.

FIG. 34C is a cross-sectional left view of the cap portion of the modular stemmed implant shown in FIG. 34A, as indicated by line 34C-34C in FIG. 34A.

FIG. 34D is a cross-sectional front view of the cap portion of the modular stemmed implant shown in FIG. 34A, as indicated by line 34D-34D in FIG. 34B.

FIG. 34E is a bottom view of the cap portion of the modular stemmed implant shown in FIG. 34A.

FIG. 34F is a bottom perspective view of the cap portion of the modular stemmed implant shown in FIG. 34A.

FIG. 34G is an enlarged bottom perspective view of the cap portion of the modular stemmed implant shown in FIG. 34A in detail, as indicated by the dashed circle around FIG. 34F.

FIG. 34H is a top view of a two-rib modular central stem according to one exemplary embodiment of the present invention.

FIG. 34I is a front view of the two-rib modular central stem shown in FIG. 34H.

FIG. 34J is a top view of a non-ribbed modular central stem according to one exemplary embodiment of the present invention.

FIG. 34K is an exploded front view illustrating the attachment of the non-ribbed modular central stem shown in FIG. 34J to the cap portion of the modular stemmed implant shown in FIG. 34A, according to one exemplary embodiment of the present invention.

DETAILED DESCRIPTION

Figure 1A:
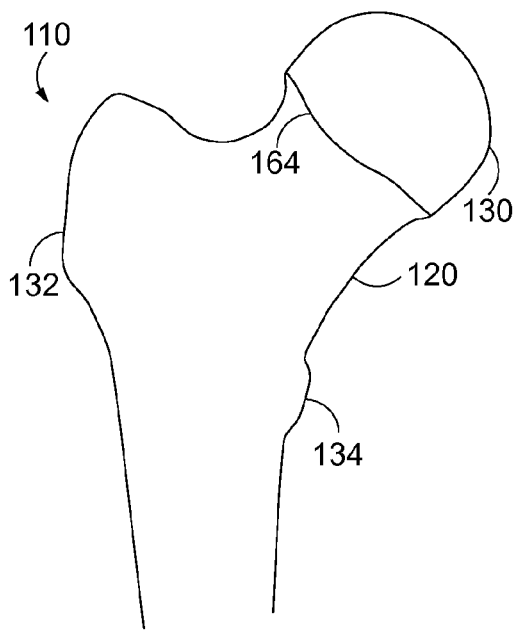
FIG. 1A is a front view from anterior of a human proximal femur.
Figure 1B:
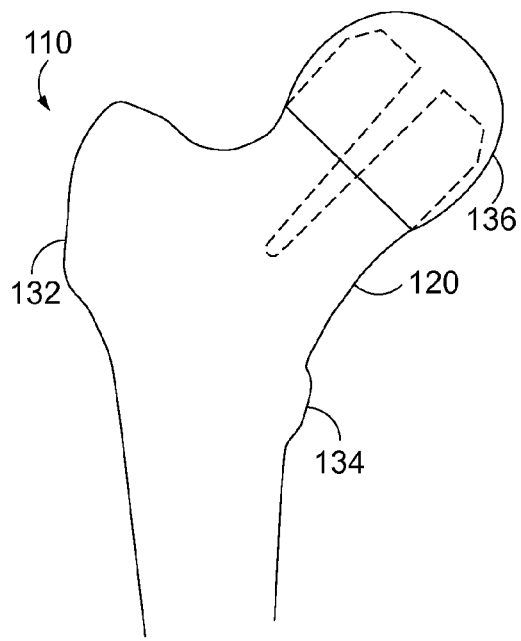
FIG. 1B is a front view illustrating a proximal femur following implantation of a hip resurfacing femoral implant with a solid joined stem, according to a previous device. The dashed line illustrates the required bone cuts for typical hip resurfacing femoral implants.

FIG. 1A is a front view from anterior of a human proximal femur 110 including femoral neck 120, femoral head 130, greater trochanter 132, lesser trochanter 134 and cartilage border, articular rim 164. FIG. 1B is a front view illustrating a proximal femur following bone cuts and implantation of a hip resurfacing femoral implant 136, according to previous devices such as the Birmingham Hip Resurfacing implant. The dashed line in FIG. 1B illustrates the required bone cuts following cylindrical reaming and osteotomies, for hip resurfacing femoral implants according to previous devices. Such a hip resurfacing femoral implant, as illustrated, has a solid stem without internal threading. Bone preparations for implantation of this hip resurfacing implant require cylindrical reaming of the femoral head past the cartilage edge, articular rim 164. As is typical with this implant, the outer, cortical, strongest bone of the femoral head is completely removed. The hip upper aspect of the hip resurfacing implant seats to the remaining spongy, less dense cancellous bone of the femoral head while the stem seats into the cancellous bone of the femoral neck. Therefore the denser, stronger cortical bone of the femoral head is neither available, nor used for support for the upper aspect of the implant, as the cortical bone is completed removed. This implant also has no additional threaded holes at its undersurface to accommodate optional threaded modular attachments, thus limiting implantation options.

Figure 1C:
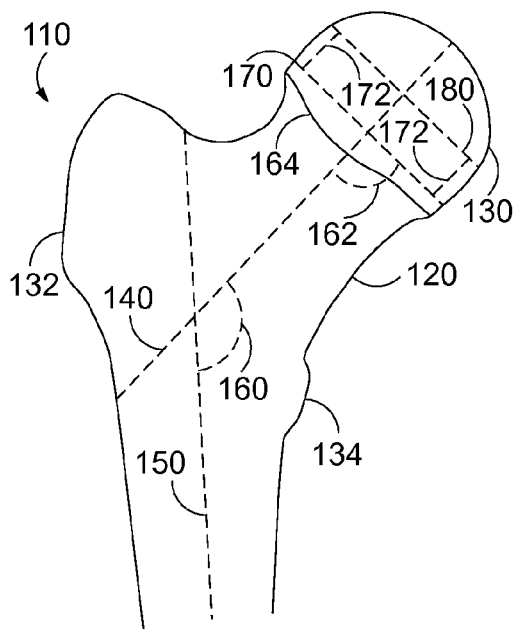
FIG. 1C is a front view of a human proximal femur illustrating reference lines and angles for surgical preparation for a modular hip resurfacing system according to the present invention.

FIG. 1C is a front view of a proximal femur illustrating the femoral neck 120, femoral head 130 and reference lines for neck-shaft angle 160, which most commonly lies between 120° to 140°, and is calculated based on the angle created by the intersection of the femoral neck axis 140 relative to the femoral shaft axis 150.

Figure 1D:
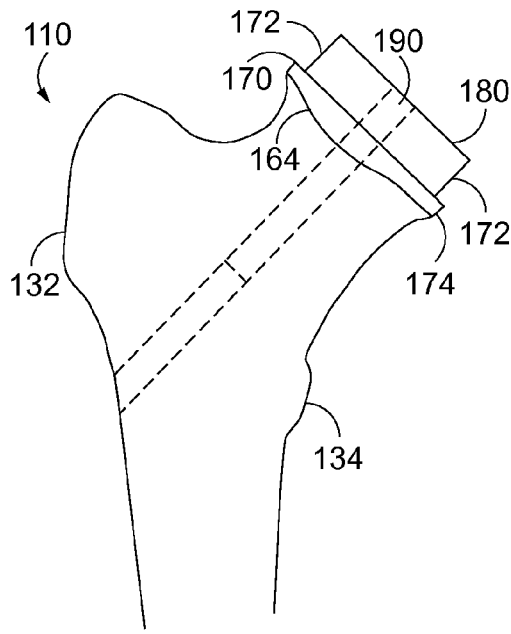
FIG. 1D is a front view of a proximal femur following bone cuts for a modular hip resurfacing system according to the present invention.

In preparation for the modular hip resurfacing system according to the present invention, a stepped cylindrical femoral head osteotomy is to be performed. This osteotomy includes a cylindrical osteotomy 172, distal osteotomy 170, and proximal osteotomy 180. The proximal and distal osteotomies are performed at a femoral neck-osteotomy angle 162 of approximately 90° in reference to the femoral neck axis 140. The distal osteotomy is performed proximal to the articular rim 164 of the femoral head 130, leaving a collar of intact cortical bone above the articular rim 164. The central bone channel 190 is drilled simultaneously during cylindrical reaming of the femoral head, as detailed below. FIG. 1D is a front view of a proximal femur following osteotomies including cylindrical reaming and simultaneous central bone channel drilling. The central bone channel can be drilled to a specific depth based on a selected exemplary embodiment, as illustrated with dashed lines in FIG. 1D.

FIGS. 2A and 2B are top and front views, respectively, illustrating an alignment guide 204 for hip resurfacing, in accordance with one exemplary embodiment of the present invention. The alignment guide of the present embodiment is useful for the proper insertion of a k-wire, guide pin, at an optimal position in the femoral head and neck for implant positioning. This alignment guide seats and secures only to the femoral head and ensures centralized insertion of the guide pin within the femoral head while also allowing placement of the guide pin parallel to the femoral neck axis, as needed. The alignment guide has four arms 208, without a vertical curvature along the height of each arm. The arms are centered at the front, right, back, and left aspects, and are equally spaced from one another, as illustrated. These arms are useful for assessing alignment with basic means of visual evaluation and with radiographic imaging, in reference to the femoral head. FIG. 2C shows an enlarged front view of a section of the alignment guide as indicated by the dashed circle in FIG. 2B. Each of the four arms 208 includes an alignment pin hole 212 along their lower aspect. Along the upper aspect of each arm are fixation holes 216 to accommodate insertion of k-wires used to secure the alignment guide to the femoral head. As illustrated in enlarged detail in FIG. 2C, all arms have thin, raised ridges, along the lower aspect of their outer surfaces. These include upper ridge 248 and lower ridge 252, both of which are used as visual reference guides. The upper ridge is used for reference for the planned proximal osteotomy 180 and the lower ridge is used for demarcation of the planned terminal point for the cylindrical reaming, distal osteotomy 170. At the top of the alignment guide is a ring 220, joined to all four arms, and centrally located between the arms. The ring has 2 handle holes 224, and one internally threaded ring hole 228. This threaded ring hole is centrally located within the ring and is also centrally located between the arms of the alignment guide.

The alignment guide can be produced to accommodate varying femoral head diameters. This is accomplished by manufacturing the alignment guide with the lower aspect of the opposing arms at increasing distances from each other while still keeping all arms equidistant from one another throughout all alignment guide sizes. The diameter of the ring remains constant through all alignment guide sizes. By having multiple alignment guide sizes to accommodate varying femoral head diameters, the alignment guide can also be used as an intraoperative measurement aid for assessing femoral head diameter. This is helpful as the femoral head diameter can be used to determine the appropriate diameter of the femoral head aspect for a planned femoral implant.

FIG. 2D shows a cross-sectional left view of the alignment guide as indicated by line 2D-2D in FIG. 2B. Two unthreaded ring holes 232 are located in the ring aspect. The internally threaded ring hole 228 passes through the ring, from the top to bottom. FIG. 2E is a bottom view of the alignment guide further showing its features including the alignment pin holes. The arms surround the periphery of the femoral head, without seating to the undersurface of the femoral head, with the arms lacking vertical curvature along the height of the arms in order to allow ample freedom of rotational adjustment. The alignment guide uses only the femoral head for its seating as it does not seat to the femoral neck or femoral head-neck junction.

FIG. 2F is a top view of a removable flat handle 236 to aid placement of the alignment guide and adjustment to its orientation and seating. The bent ridges illustrated along the surface stop the removable flat handle from inserting into the alignment guide beyond the beginning of each ridge and also can be helpful for gripping the removable flat handle. The separate ends of the removable flat handle can be squeezed by hand towards each other to decrease the distance between them and allow handle insertion into the handle holes 224 of the alignment guide. The distance between the handle ends is slightly wider than the distance between the handle holes in the alignment guide requiring pressure to be applied in a squeezing motion to insert the handle. This elastic aspect of the handle also helps keep the handle secured into place during usage, as the handle will apply pressure within the surfaces of the handle holes while seated into the alignment guide. The handles assist with alignment guide positioning. FIGS. 2G and 2H are rear and front views, respectively, of the removable flat handle. FIG. 2I is a right view of the removable flat handle further illustrating the location of the ridges along the surface of the removable flat handle.

FIGS. 2J and 2K are rear and front views, respectively, of an alignment pin 240 to aid in alignment of the alignment guide in relation to the proximal femur. FIG. 2L is a right view of the alignment pin. The alignment pins can be inserted into the alignment pin holes 212. The alignment pins aid the alignment of the alignment guide in relation to the femoral head and femoral neck axis, using basic means of visual evaluation, and through radiographic imaging when using fluoroscopic imaging during the surgical procedure. Following placing of the alignment guide onto the surface of the femoral head and insertion of the alignment pins and basic visual evaluation, fluoroscopic imaging can be used to confirm proper alignment of the alignment guide seating onto the femoral head, and that it is parallel to the femoral neck axis in coronal and sagittal planes, oblique, and additional radiographic imaging planes, if needed. The alignment guide can be rotated in all planes to adjust for femoral neck version and varus and valgus angulation. The alignment pins can be produced in varying lengths with respect to its length from its base to the bevel at the upper aspect, with the length of the beveled aspect remaining constant through all sizes. Alignment pin size selection is based on requirements for each case, surgical approach and available space for placement of the alignment pins.

FIGS. 2M and 2N are top and front views, respectively, of a cannulated guide pin screw 244, which is threaded into the threaded ring hole 228 of the alignment guide. The cannulated guide pin screw accommodates a guide pin to be inserted through its center from top to bottom. The hole in the guide pin screw is centrally located within the cannulated guide pin screw. As the threaded ring hole is centrally located between the arms, the hole in the cannulated guide pin screw is also centrally located between the arms, once seated. The cannulated guide pin screw has 4 wings located at its top aspect, all equally spaced from one another, to make manual tightening and loosening easier. The screw has an external thread pattern along its base, as illustrated. FIG. 2O shows a cross-sectional right view of the cannulated guide pin screw as indicated by line 2O-2O in FIG. 2N. FIG. 2P is a bottom view of the cannulated guide pin screw.

Figures 3A, 3B:
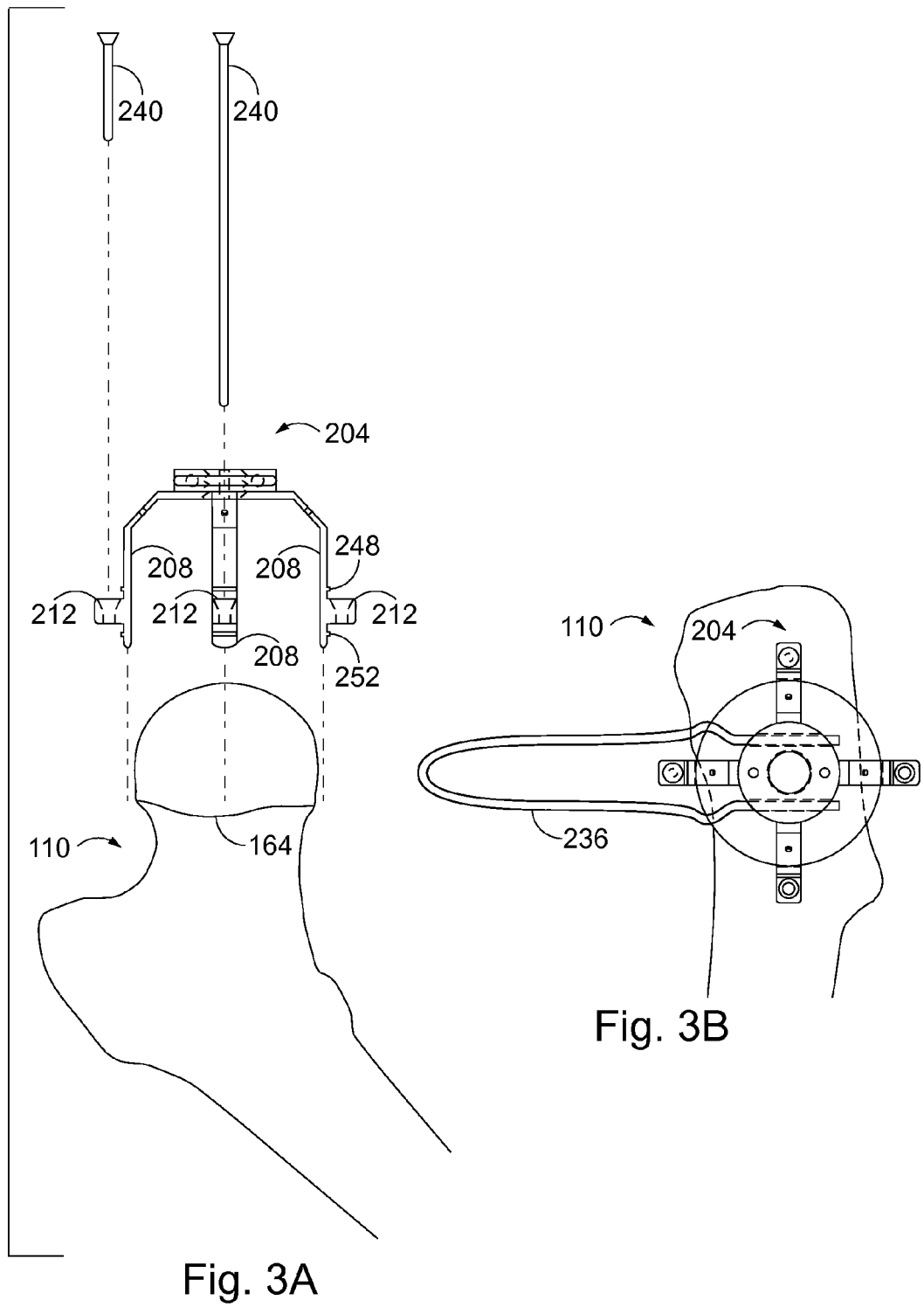
FIG. 3A is an exploded front view illustrating the alignment guide to be seated onto the femoral head with alignment pins to be inserted to aid alignment according to the present invention.
FIG. 3B is a top view of the alignment guide properly seated onto the femoral head with alignment pins inserted according to the present invention.

FIG. 3A is an exploded front view illustrating the alignment guide 204 to be seated onto the femoral head 130 with two alignment pins 240 to be inserted to aid in evaluation of alignment. Alignment pins can be inserted into the alignment pin holes 212, as demonstrated. Following a standard surgical approach for hip resurfacing arthroplasty, the hip is surgically dislocated, according to previous methods. According to the present invention, the alignment guide is placed so that the lower ridge 252 of each arm is always above the articular rim, as illustrated, which will result in a collar of intact cortical bone, secondary to alignment guide use and the subsequent cylindrical reaming procedure, described in detail below. FIG. 3B is a top view of the alignment guide seated onto the femoral head, with removable flat handle 236 inserted to aid manual adjustment and stabilization.

As described, the alignment guide can be produced in varying sizes. The femoral head diameter can easily be determined by attempting placement of the smallest size alignment guide and sequential fitment of the next larger size can be attempted, as needed. Once a selected alignment guide seats easily but securely to the femoral head in multiple longitudinal positions, the femoral head diameter is noted. The femoral head diameter is easily determined as the alignment guide diameter corresponds to the femoral head diameter. The alignment guide diameter measurement can be labeled on each alignment guide to make the femoral head diameter readily available for reference.

Figure 4A:
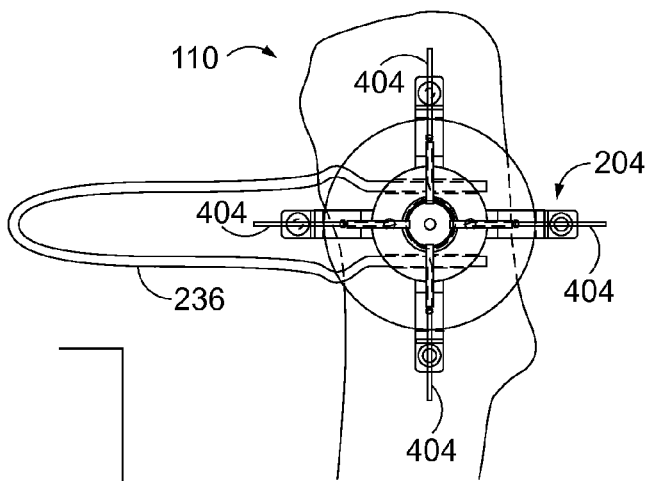
FIG. 4A is an exploded front view illustrating four k-wires to be inserted through the alignment guide into the femoral head and a cannulated guide pin screw to be threaded into the alignment guide until seated against the articular surface of the femoral head according to the present invention.

The orientation and seating of the alignment guide can be repeatedly checked with basic means of visual evaluation ensuring proper seating with its lower ridge above the articular rim, and using radiographic evaluation using intra-operative fluoroscopic imaging. Proper orientation is illustrated in FIGS. 3A, 3B and 4A. Fluoroscopic imaging is useful for checking seating and for confirming parallel positioning of the seated alignment pin(s) in reference to the femoral neck axis. The ring itself can also be beneficial for checking alignment. To aid visual and radiographic alignment with respect to the femoral head and femoral neck, the central, the threaded ring hole 228 (prior to placement of the cannulated guide pin screw 244) and unthreaded ring holes 232 in the ring can be used to check positioning as well as the outer edges of the ring and arms. The positioning of alignment guide can be adjusted on multiple planes including coronal and sagittal, oblique, and additional radiographic imaging planes as needed. Precise placement is possible using radiographic fluoroscopic imaging through use of the alignment pins by lining up the arms and alignment pins in relation to the femoral neck axis. Depending on both the visualization required and individual surgeon preference, the number of alignment pins 240 used during each procedure may be adjusted from zero to four (with four allowing one alignment pin on each arm of the alignment guide). The alignment pins can be produced in varying lengths, which can be selected based on the requirements of each case and the surgical exposure. The alignment pins may also be fully or partially inserted for an additional method for adjustment. The arms and alignment pins aid in proper orientation of the alignment guide through basic visual evaluation during the surgical procedure and can be confirmed with radiographic evaluation using fluoroscopic imaging.

FIG. 4A is an exploded front view illustrating four k-wires 404 to be inserted through the arm fixation holes 216 past the articular surface of the femoral head. The alignment guide can be seated along the articular surface of the femoral head, with the bottom edge of each arm of the alignment guide near the articular rim and with the lower ridge always above the articular rim, as illustrated, which can result in a collar of intact cortical bone, secondary to alignment guide use and the subsequent cylindrical reaming procedure, described in detail below. Thus, once proper positioning is achieved, as illustrated in FIG. 4A, the alignment guide is ready to be secured into position.

Figure 4B:
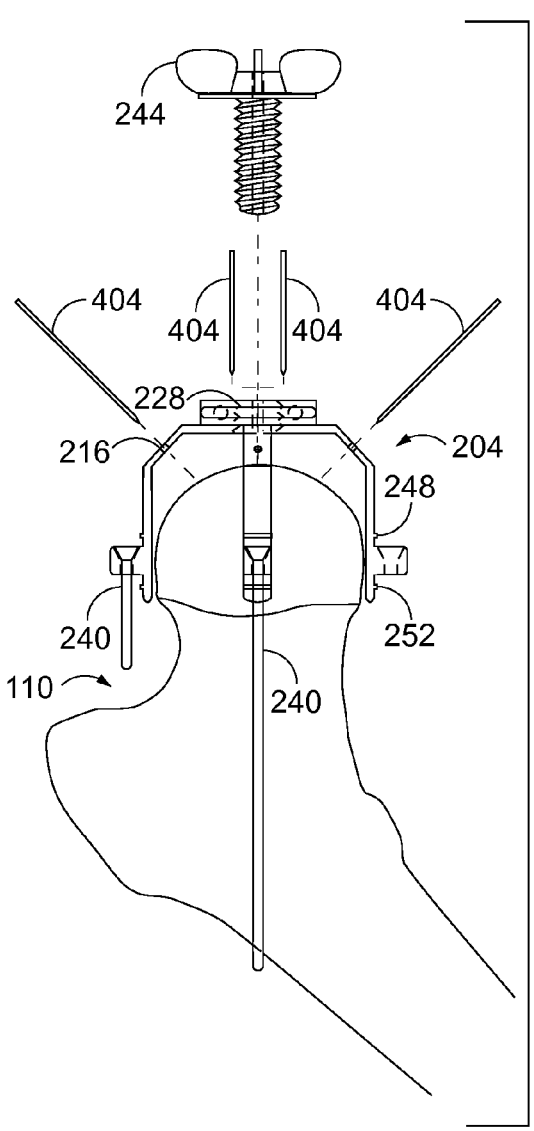
FIG. 4B is a top view of the alignment guide with four k-wires inserted through the alignment guide into the femoral head and the cannulated guide pin screw threaded into the alignment guide resting against the articular surface of the femoral head according to the present invention.
Figure 4C:
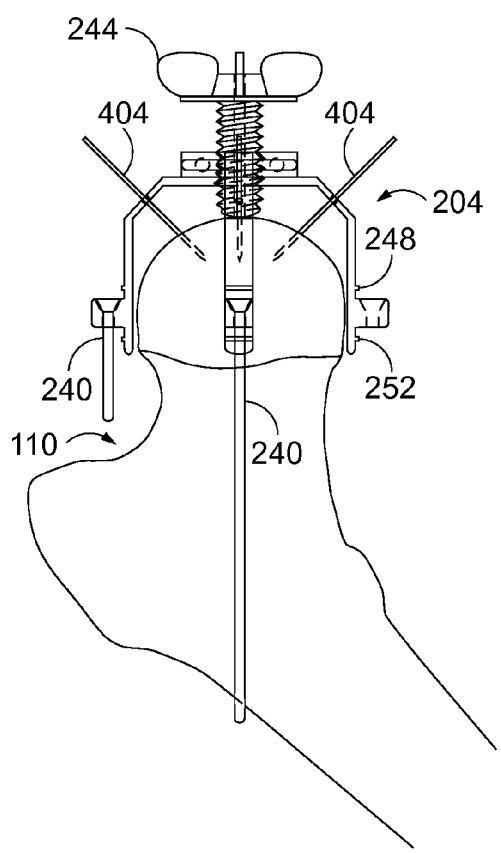
FIG. 4C is a front view further illustrating four k-wires inserted through the alignment guide into the femoral head and the cannulated guide pin screw threaded into the alignment guide and seated against the articular surface of the femoral head according to the present invention.

Insertion of the k-wires into the arm fixation holes 216 can be performed using a standard surgical pin driver or surgical drill. The k-wires are not deeply inserted into the femoral head in order to avoid the possibility of interfering with later guide pin insertion. The k-wires help secure the alignment guide into position for the next step of the procedure. After the k-wires are inserted, the cannulated guide pin screw 244 is threaded into the threaded ring hole of the alignment guide and loosely tightened by hand until it rests upon the articular surface of the femoral head. It is not tightened forcefully as it only needs to make contact with the articular surface of the femoral head for stability. FIG. 4B and. FIG. 4C are top and front views, respectively, of the alignment guide secured onto the femoral head with the k-wires correctly inserted through the arm fixation holes past the cortical bone of the femoral head. As illustrated, the cannulated guide pin screw is correctly inserted and seated, securely resting upon the articular surface of the femoral head. Additional fluoroscopic imaging is obtained at this point to confirm final positioning and orientation of the alignment guide, and reconfirming proper parallel alignment of alignment pin(s) in relation to the femoral neck axis. Further adjustment can be performed by sequential removal of k-wire fixation and careful readjustment, as required. K-wires can then once again be inserted through the arm fixation holes once proper orientation of the alignment guide is achieved.

Figures 5A, 5B:
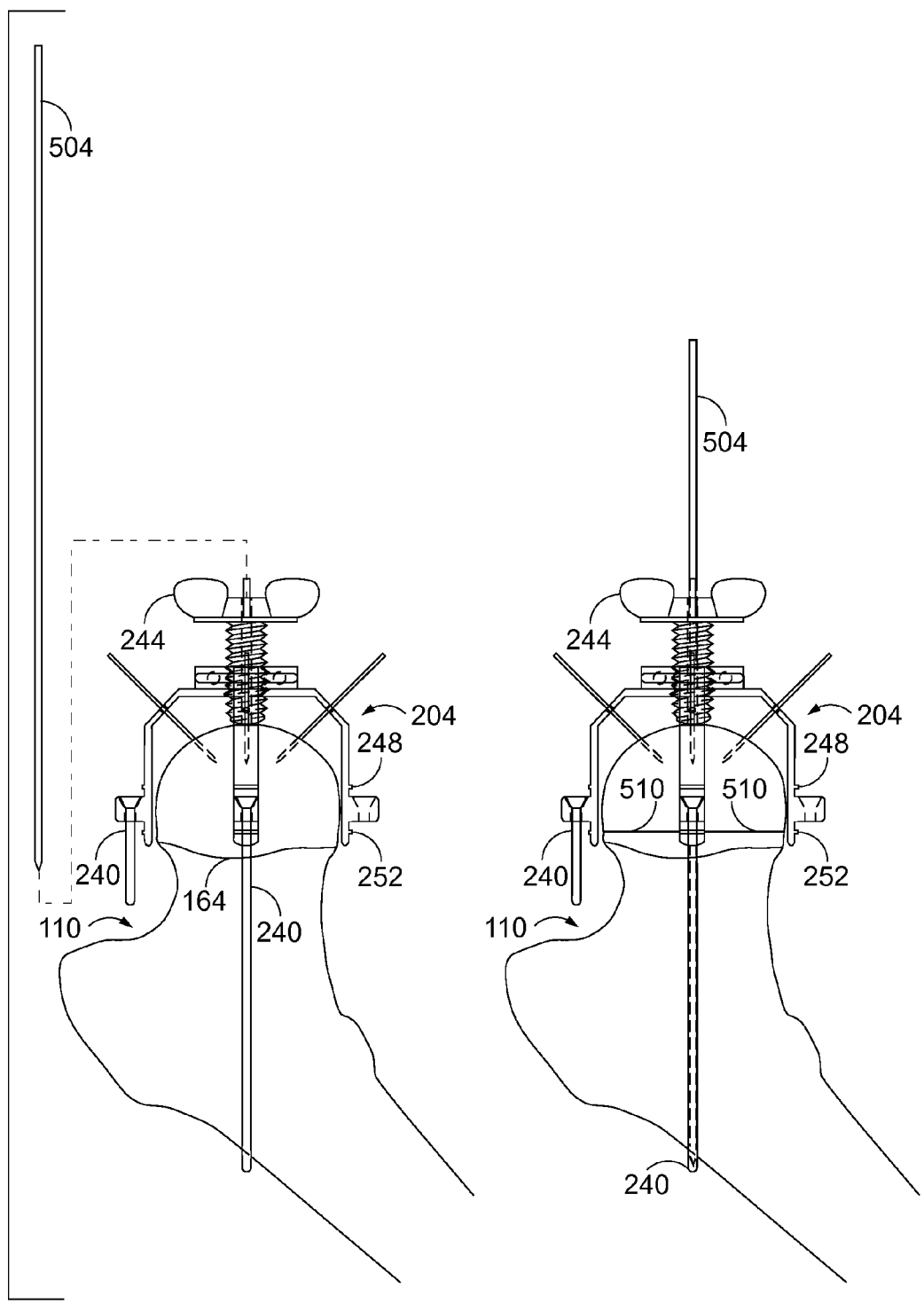
FIG. 5A is an exploded front view illustrating a guide pin to be inserted through the cannulated guide pin screw according to the present invention.
FIG. 5B is a front view illustrating the guide pin inserted through the cannulated guide pin screw past the articular surface of the femoral head through the femoral neck and just exiting through the lateral cortex of the femoral shaft below the greater trochanter according to the present invention. The planned terminal point for cylindrical reaming has also been demarcated according to the present invention.

FIG. 5A is an exploded front view illustrating the k-wire, guide pin 504 which is to be inserted through the cannulated guide pin screw. This step is accomplished using a standard surgical pin driver or surgical drill. As further illustrated in FIG. 5B, a front view, the guide pin is inserted so it passes through the cannulated guide pin screw, into the articular surface of the femoral head, through the femoral head and neck, and just to the point where it reaches and just exits the lateral cortex of the femoral shaft below the greater trochanter. Alternately, the guide pin screw may be inserted to a more shallow depth, as needed. In applications where the planned central bone channel does not exit the lateral cortex, guide pin insertion can stop before the lateral cortex. Intraoperative fluoroscopic imaging can also be used during this step to confirm appropriate depth and positioning of the guide pin in multiple radiographic image planes. A surgical marking pen is used to demarcate the planned terminal point 510 at a latitudinal location above the articular rim of the femoral head for the cylindrical reamer, within the areas between each arm of the alignment guide. The lower ridge 252 of the alignment guide on each arm is used as a reference for this line, as the demarcated line essentially intersects the lower ridge of each arm when properly marked. These lines are drawn so they meet the center of each lower ridge, as illustrated. The top or bottom edge of a surgical ruler can also be used as a straight edge during this step. Alternatively, the line may be scored along the articular surface using a scalpel with a sharp blade with or without a secondary use of surgical marking pen after for further marking of the terminal point for the cylindrical reamer. The upper ridge along each arm provides a relative visual reference for location of the proximal osteotomy. However, demarcation of a reference line using the upper ridges, is not required. The upper ridges are for reference only in the current exemplary embodiment as a proximal osteotomy is performed later in the surgical procedure, using a saw guide, which helps to create a precise proximal osteotomy following the cylindrical reaming procedure.

FIGS. 6A and 6B are top and front views, respectively, illustrating various aspects of a cylindrical reamer 604 for hip resurfacing, in accordance with one exemplary embodiment of the present invention. The center of the lower portion of the cylindrical reamer is hollow, as illustrated, in order to accommodate the central aspect of the femoral head. Within the top center of this hollow portion is a cylindrical reamer drill base receptacle 608. Along the bottom of the cylindrical reamer are wide cutting blades 610. These wide cutting blades allow for cutting away of the peripheral bone of the femoral head, to a predetermined latitudinal location above the articular rim, forming a cylindrical shape, without leaving a resultant sleeve of bone along the outer surface of the cylindrical reamer. FIG. 6C is a bottom view of the cylindrical reamer, further showing the cutting blades and cylindrical reamer drill base receptacle. FIG. 6D shows a cross-sectional left view of the cylindrical reamer, as indicated by line 6D-6D in FIG. 6B, further showing its features including the wide cutting blades.

FIG. 6E is a top view illustrating various aspects of a cylindrical reamer fastener 612, in accordance with one exemplary embodiment of the present invention. It has 4 wings located at its top aspect, equally spaced from one another, making manual tightening and loosening easier. FIG. 6F is a front view further illustrating the cylindrical reamer faster, which includes an internally threaded, fastener threaded hole 614. FIG. 6G is a bottom view of the cylindrical reamer fastener, further illustrating the wings along its top aspect. FIG. 6H shows a cross-sectional left view of the cylindrical reamer fastener, as indicated by line 6H-6H in FIG. 6F, further illustrating the fastener threaded hole.

FIGS. 6I and 6J are top and front views, respectively, illustrating various aspects of a cannulated cylindrical reamer drill base 616, in accordance with one exemplary embodiment of the present invention. Extending through cylindrical reamer drill base from top to bottom is a central channel, guide pin hole 620, as illustrated, which accommodates a guide pin. At the upper aspect of the cannulated cylindrical reamer drill base is a hex drill attachment point 624, which accommodates attachment to surgical drill. Under the hex drill attachment point is an externally threaded, threaded aspect 628, which mates with the cylindrical reamer fastener. This allows the cylindrical reamer to be secured to the cannulated cylindrical reamer drill base. Below the threaded aspect is a hex cylindrical reamer attachment aspect 632, which mates with the cylindrical reamer drill base receptacle 608, of the cylindrical reamer. Below the cylindrical reamer drill base receptacle is a drill cutting edge 636, which drills a central bone channel for the modular hip resurfacing implant. FIG. 6K shows a cross-sectional left view of the cannulated cylindrical reamer drill base, as indicated by line 6K-6K in FIG. 6J, further illustrating the guide pin hole. FIG. 6L is a front view of a shorter cannulated cylindrical reamer drill base for a decreased resultant drilling depth. The cannulated cylindrical reamer drill base can be produced in varying lengths, with the choice of length in each case being based on selection of implant and modular options detailed herein. Specifically, the section between the hex cylindrical reamer attachment aspect to the bottom edge of the cannulated cylindrical reamer drill base will vary in length while the length of upper aspect, above the above the hex cylindrical reamer attachment aspect, remains constant in length throughout all size options. This thereby allows modular configuration options for choice of central bone channel length or for custom selection based on any anatomic variation in femoral neck length between individuals. FIG. 6M is a bottom view of the cannulated cylindrical reamer drill base, further illustrating the lower aspects of the cannulated cylindrical reamer drill base.

Figures 7A, 7B:
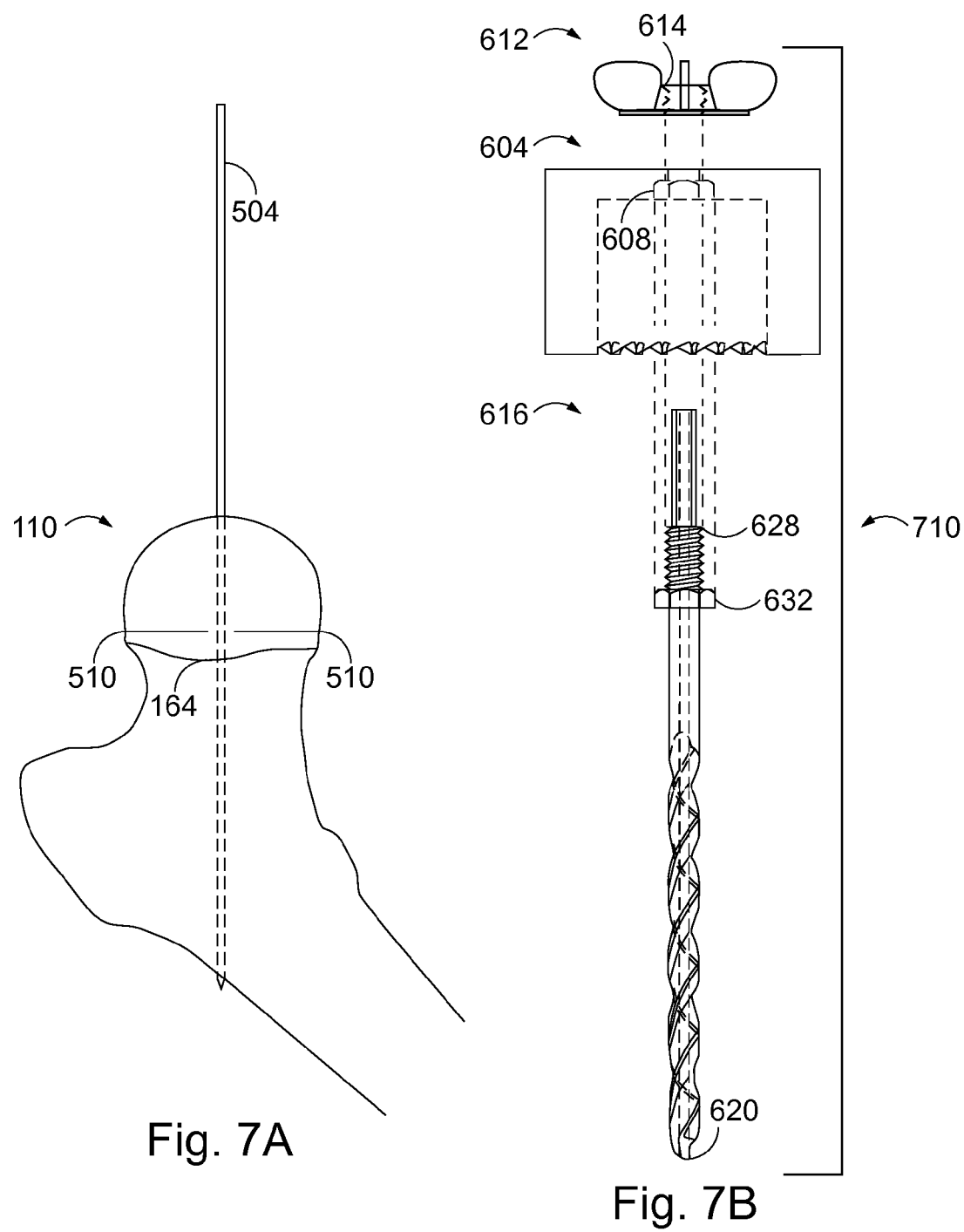
FIG. 7A is a front view illustrating the final position of the guide pin with the planned terminal point for cylindrical reaming demarcated according to the present invention.
FIG. 7B is an exploded front view illustrating assembly of a cylindrical reamer onto a cannulated cylindrical reamer drill base to be securely joined by a cylindrical reamer fastener according to the present invention.

FIG. 7A is a front view illustrating final position of the guide pin after the alignment guide is removed. As described, the alignment guide ensures centralized insertion of the guide pin within the femoral head while also allowing placement of the guide pin parallel to the femoral neck axis. The alignment guide also assists with planning and marking the correct planned terminal point 510 for cylindrical reaming aided by the lower ridge 252 of the alignment guide. The planned terminal point 510 for the cylindrical reamer is always above the articular rim 164, according to the present invention.

FIG. 7B is an exploded front view illustrating the assembly of the cylindrical reamer 604 onto the cannulated cylindrical reamer drill base 616 to be securely joined by the cylindrical reamer fastener 612 so that the hex cylindrical reamer attachment aspect 632 inserts into the cylindrical reamer base receptacle 608. The modular cannulated cylindrical reamer assembly 710 is now ready for use. The cylindrical reamer fastener is threaded into place with its fastener threaded hole 614 mated to the threaded aspect 628 of the cannulated cylindrical reamer drill base. Hand tightening using the wings located at the top surface of the cylindrical reamer fastener is typically sufficient. Thus, the modular cannulated cylindrical reamer assembly allows for the simultaneous cutting away of the peripheral bone of the femoral head, to a predetermined latitudinal location, at the same time as drilling of a central bone channel. Shorter cannulated cylindrical reamer drill bases can be used to accommodate modular hip resurfacing options requiring shorter central bone channels including central bone channels which do not extend through the lateral cortex of the femoral shaft.

Figure 8A:
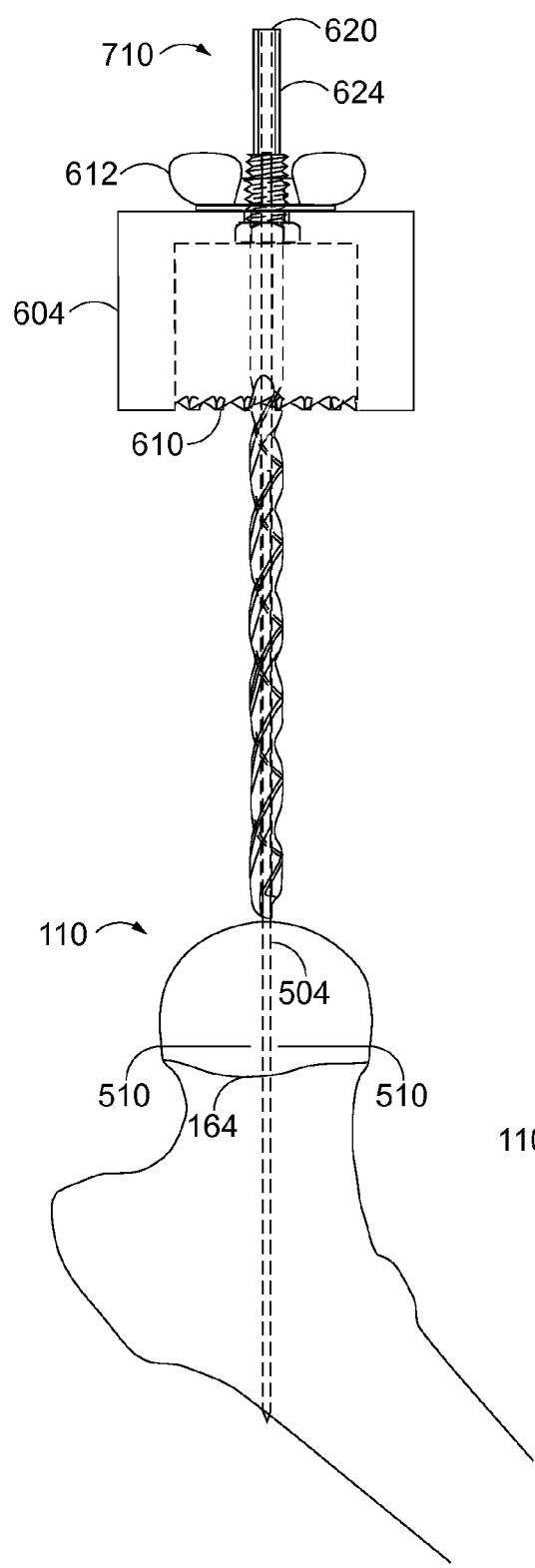
FIG. 8A is a front view illustrating placement of the modular cannulated cylindrical reamer assembly over the guide pin according to the present invention.
Figure 8B:
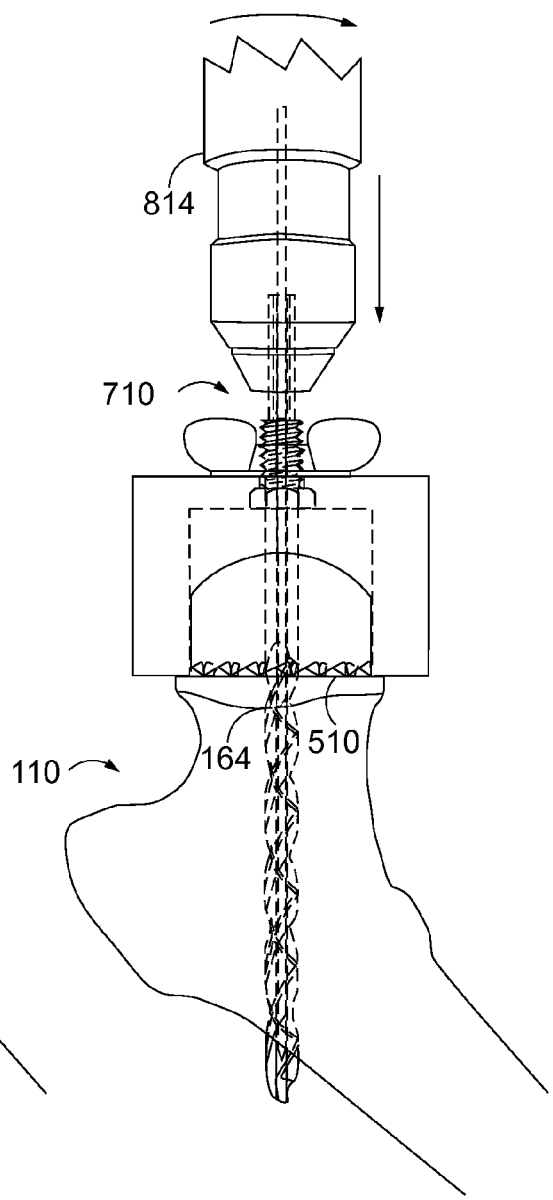
FIG. 8B is a front view illustrating the cylindrical reamer assembly, which has been connected to a surgical drill, and drilled to its previously demarcated planned latitudinal terminal point on the femoral head according to the present invention.

FIG. 8A is a front view illustrating placement of the modular cannulated cylindrical reamer assembly 710 over the guide pin. The assembled cannulated reamer is inserted and attached to a surgical drill in standard fashion using the hex drill attachment point 624. A sterile surgical cloth or another suitable material may be dampened with saline and placed peripherally around the femoral neck during the cylindrical reaming procedure in order to contain bone debris. 8B is a front view illustrating the cylindrical reamer, connected to a surgical drill 814, which is partially illustrated. If a long cylindrical reamer drill base is chosen for an application requiring drilling through the lateral cortex of the femur, a surgical retractor may be placed prior to drilling, with the retractor base centered near the guide pin exit point in the lateral cortex protecting nearby soft tissues. After the assembled cannulated reamer is placed so that the guide pin inserts into the guide pin hole 620, cylindrical reaming can begin with the surgical drill. During the cylindrical reaming procedure, slow, gentle downward pressure is applied along the axis of the guide pin while constantly monitoring the drill depth during the procedure. As illustrated, cylindrical reaming is completed when the bottom edge of the cutting blades 610 just reach the previously demarcated planned terminal point 510 on the femoral head. The surgical drilling speed is slowed as the terminal point for the cylindrical reamer is neared to ensure precision.

Figure 9A:
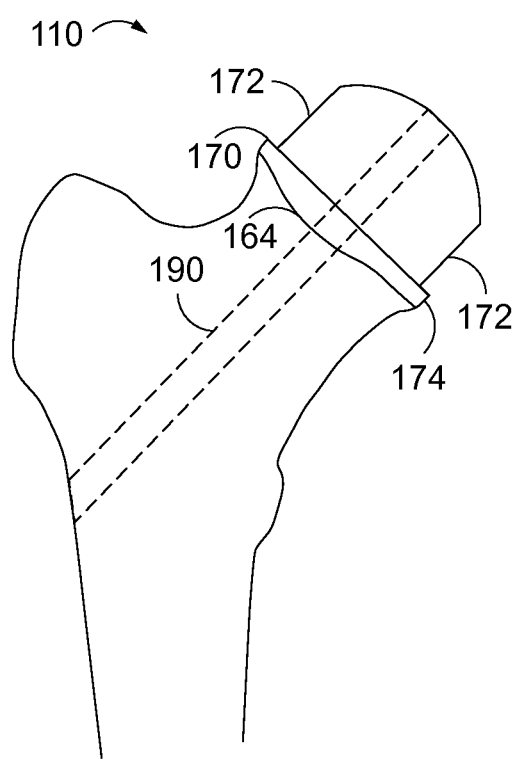
FIG. 9A is a front view illustrating the resultant cylindrical osteotomy of the femoral head and also the central bone channel according to the present invention.
Figure 9B:
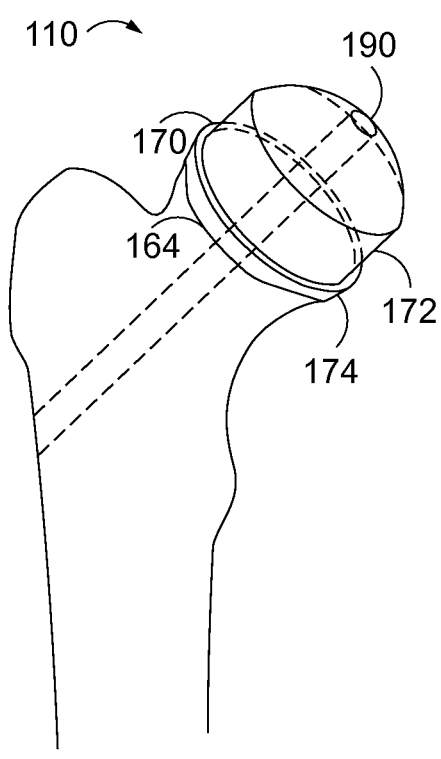
FIG. 9B is a front perspective view further illustrating the resultant cylindrical osteotomy of the femoral head and central bone channel according to the present invention.

FIG. 9A is a front view illustrating the proximal femur 110 with the resultant cylindrical osteotomy 172 of the femoral head and central bone channel. The distal osteotomy 170 is above the articular rim 164 of the femoral head leaving an intact collar of remaining femoral head cortex 174 above the articular rim following all osteotomies. The central bone channel 190 is also completed simultaneously and extends through the lateral cortex of the femoral shaft. A shorter central bone channel can be created, when required, through the use of a shorter cylindrical reamer drill base 616. FIG. 9B is a front perspective view further illustrating the resultant cylindrical reaming of the femoral head and central bone channel with the cylindrical osteotomy and distal osteotomy further illustrated.

Figure 10A:
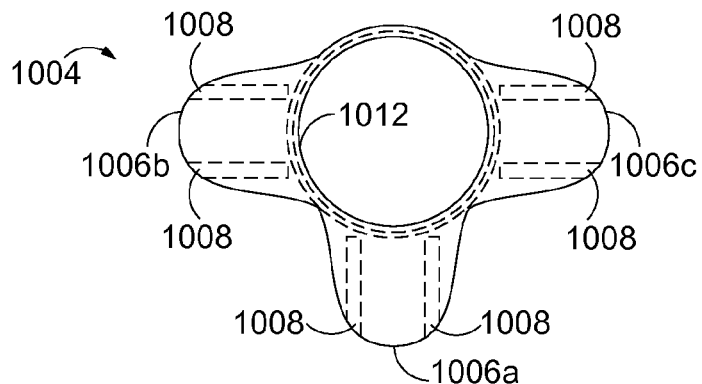
FIG. 10A is a top view illustrating a saw guide for hip resurfacing, in accordance with one exemplary embodiment of the present invention.
Figure 10B:
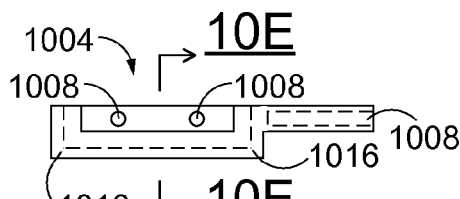
FIG. 10B is a left view of the saw guide shown in FIG. 10A.
Figure 10C:
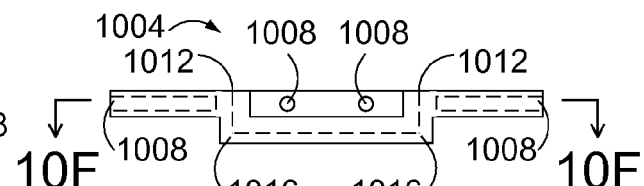
FIG. 10C is a front view of the saw guide shown in FIG. 10A.
Figure 10D:
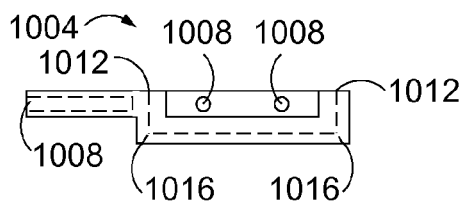
FIG. 10D is a right view of the saw guide shown in FIG. 10A.
Figure 10E:
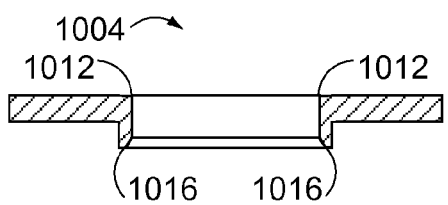
FIG. 10E is a cross-sectional rear view of the saw guide shown in FIG. 10A, as indicated by line 10E-10E in FIG. 10B.
Figure 10F:
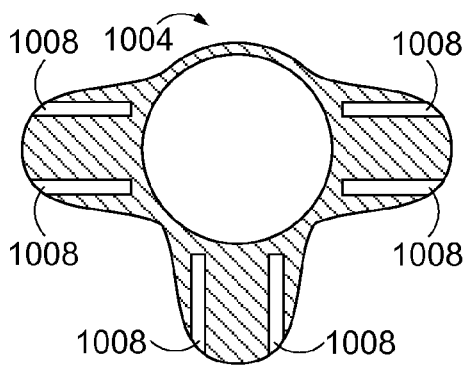
FIG. 10F is a cross-sectional top view of the saw guide shown in FIG. 10A, as indicated by line 10E-10F in FIG. 10C.

FIG. 10A is a top view illustrating various aspects of a saw guide 1004 for hip resurfacing, in accordance with one exemplary embodiment of the present invention. The saw guide has extensions along its front, left and right aspects. These include the front platform 1006a, left platform 1006B, and right platform 1006c. These platforms are enlarged smooth surfaces providing a flat and stabile base for an oscillating saw blade to gently rest and oscillate against. The saw guide seats onto the prepared femoral head and includes handle holes 1008 along the front, right and left aspects to accommodate removable handles. FIG. 10B is a left view of the saw guide, and FIG. 10C is a front view of the saw guide. At the center of the saw guide is a cylindrical, inner edge 1012, which transitions to a beveled lower edge 1016 at its base to make seating easier. The bottom surface of the saw guide is flat and designed to seat on the resultant collar of femoral head cortical bone above the articular rim. FIG. 10D is a right view of the saw guide, and FIG. 10E shows a cross-sectional front view of the saw guide, as indicated by line 10E-10E in FIG. 10B, further illustrating the inner surfaces. FIG. 10F shows a cross-sectional top view of the saw guide as indicated by line 10E-10F in FIG. 10C. The saw guide may be available in two or more heights to account for both smaller and larger femoral head diameters. The saw guide directs the surgical saw to a precise height, simplifying the process of performing this osteotomy at the correct location.

Figure 10G:
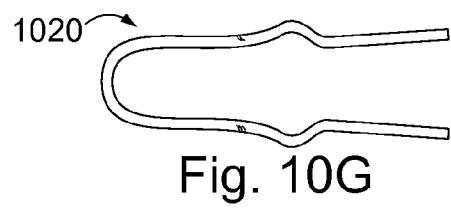
FIG. 10G is a top view of a removable angled handle, in accordance with one exemplary embodiment of the present invention.
Figure 10H:
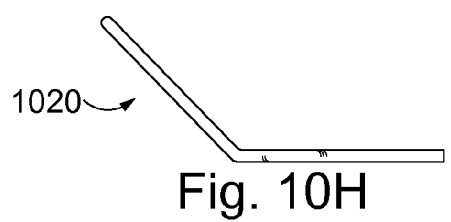
FIG. 10H is a right view of the removable angled handle shown in FIG. 10G.

FIG. 10G is a top view of a removable angled handle 1020 to aid in both placement of the saw guide and maintenance of its seating during use. The removable angled handle makes application of manually applied downward pressure easier, and also aids in stabilization of the saw guide during use of a surgical saw. There are bent ridges along the surface of the removable angled handle, as illustrated, which can be helpful for gripping the handle, and the outer aspect of the removable angled handle is angled upwards when properly seated into the handle holes of the saw guide. The separate ends of the handle can be squeezed by hand towards each other to decrease the distance between them and allow handle insertion into the handle holes 1008 of the saw guide. In the natural state of the removable angled handle, the distance between the handle ends are slightly wider than the distance between the handle holes requiring pressure to be applied in a squeezing motion in order to insert the handle. This elastic aspect of the handle also helps to keep the handle securely seated into the saw guide during usage since the handle will apply pressure within the handle holes while seated into the saw guide. FIG. 10H is a right view of the removable angled handle. The removable angled handle is angled upwards, as illustrated, in order to aid the user in applying continuous proper seating of the saw guide throughout use.

Figure 11A:
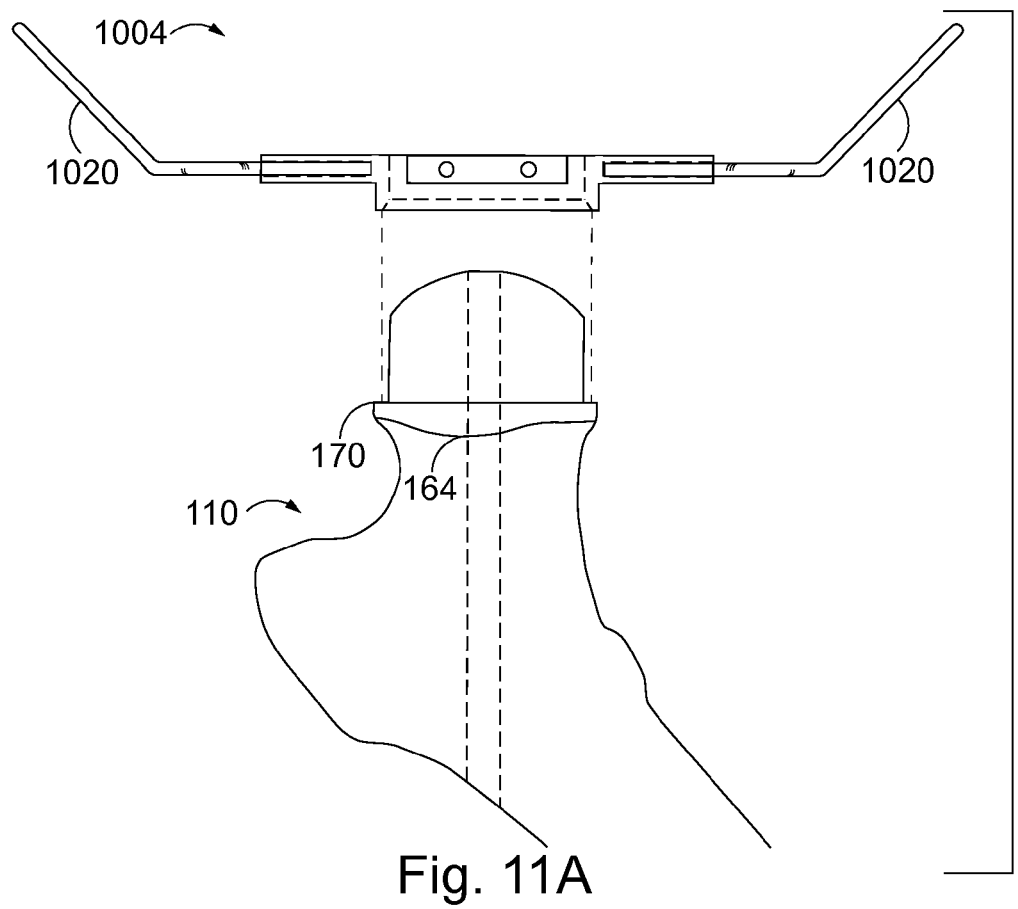
FIG. 11A is an exploded front view illustrating the seating of the saw guide, with two removable angled handles attached, to be placed over the upper cortical edge of the femoral head following cylindrical reaming according to the present invention.
Figure 11B:
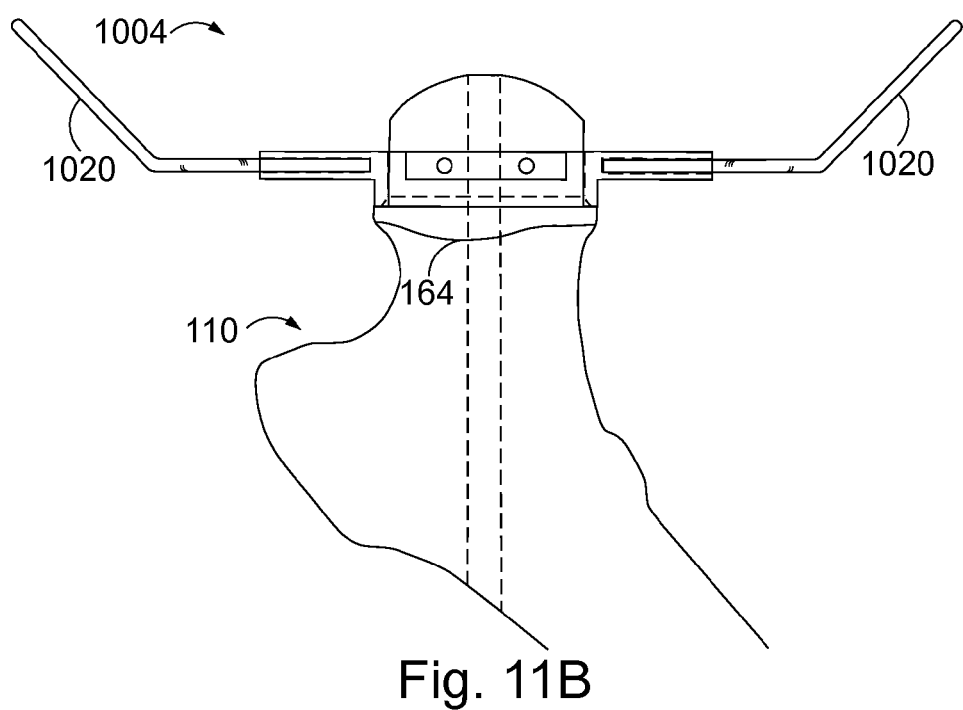
FIG. 11B is a front view illustrating final placement of the saw guide according to the present invention.

FIG. 11A is an exploded front view illustrating the saw guide 1004 which is to be seated onto the prepared proximal femur 110 with two removable angled handles 1020 inserted. Following completion of the prior cylindrical reaming procedure, the saw guide can be seated on top of the flat, planar bone surface at the distal osteotomy 170. FIG. 11B is a front view of the saw guide illustrating its final seating onto the femoral head. The top of the saw guide provides a flat surface for an oscillating saw to rest and oscillate against.

Figure 12A:
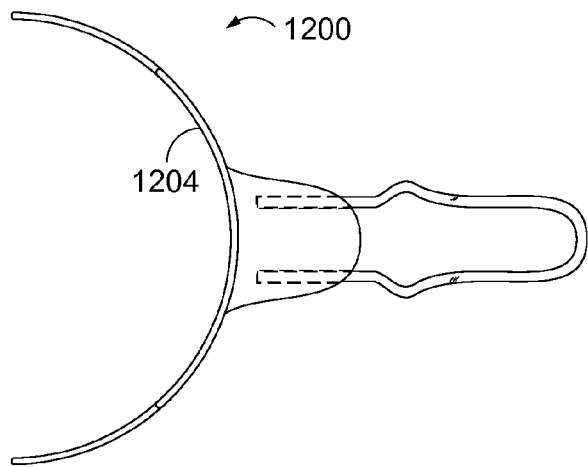
FIG. 12A is a top view illustrating a soft tissue protector, in accordance with one exemplary embodiment of the present invention.
Figure 12B:
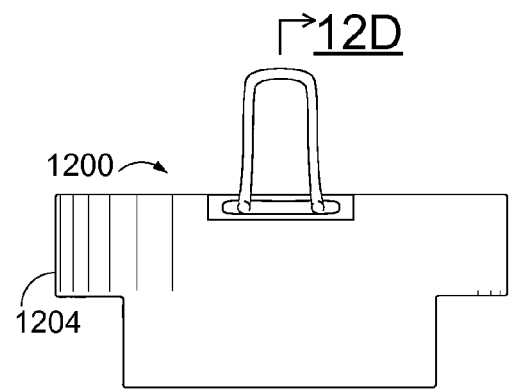
FIG. 12B is a front view of the soft tissue protector shown in FIG. 12A.
Figure 12C:
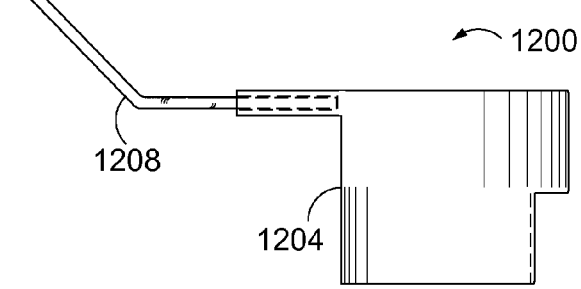
FIG. 12C is a right view of the soft tissue protector shown in FIG. 12A.
Figure 12D:
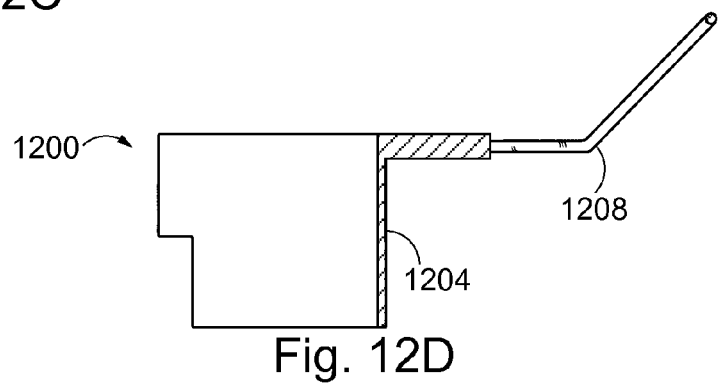
FIG. 12D shows a cross-sectional left view of the soft tissue protector shown in FIG. 12A, as indicated by linen 12D-12D in FIG. 12B.

FIG. 12A is a top view illustrating various aspects of a soft tissue protector 1200 which can be used for both shielding and retraction of soft tissues during the femoral head proximal osteotomy, in accordance with one exemplary embodiment of the present invention. It can also be used throughout other aspects of the present invention, as desired, such as during cylindrical reaming and acetabular component placement. The soft tissue protector has a curved protector aspect 1204, which also protects the soft tissues from the surgical saw blade during the proximal osteotomy as it is placed between the femoral head and soft tissues. The curved protector aspect of the soft tissue protector is also stepped along its outer bottom aspects, as illustrated, allowing placement partially over the removable angled handles of the saw guide permitting simultaneous use with the saw guide. A fixed angled handle 1208 is joined to the upper aspect of the soft tissue protector. The fixed angled handle aids in both retraction of soft tissues and maintenance of proper seating. The fixed angled handle is welded into place in this exemplary embodiment but may be formed as cast in alternate embodiments. There are bent ridges along the surface of the fixed angled handle, as illustrated, which can be helpful for gripping the handle. FIG. 12B is a front view of the soft tissue protector further illustrating the stepped aspects. FIG. 12C is a right view of the soft tissue protector further illustrating the semicircular shape of the curved protector aspect and the fixed angled handle. FIG. 12D shows a cross-sectional left view of the soft tissue protector as indicated by line 12D-12D in FIG. 12B.

Figure 13A:
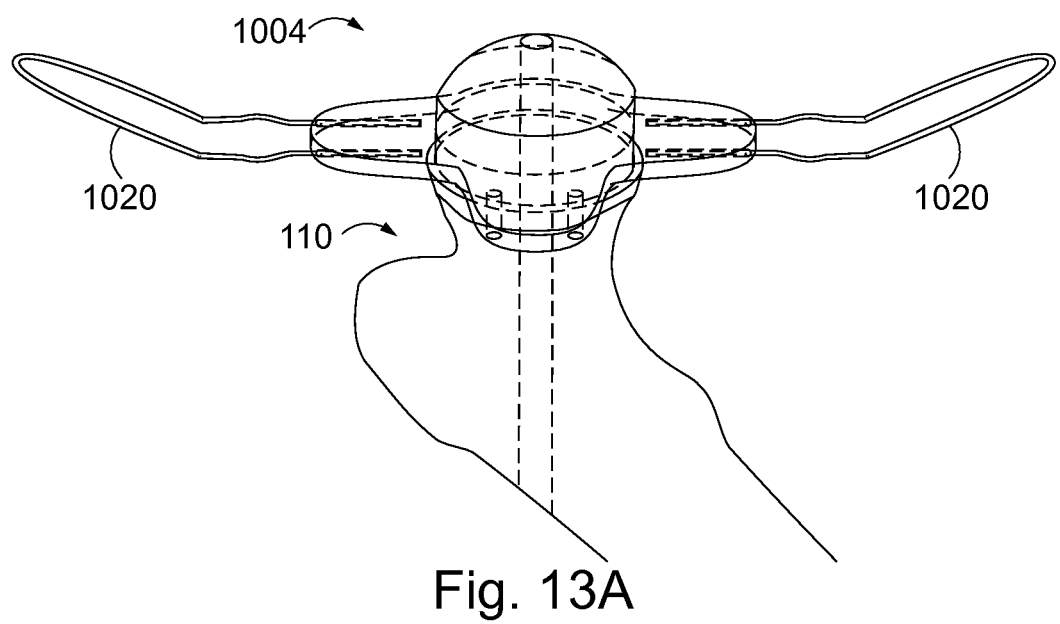
FIG. 13A is a front perspective view further illustrating final placement of the saw guide according to the present invention.
Figure 13B:
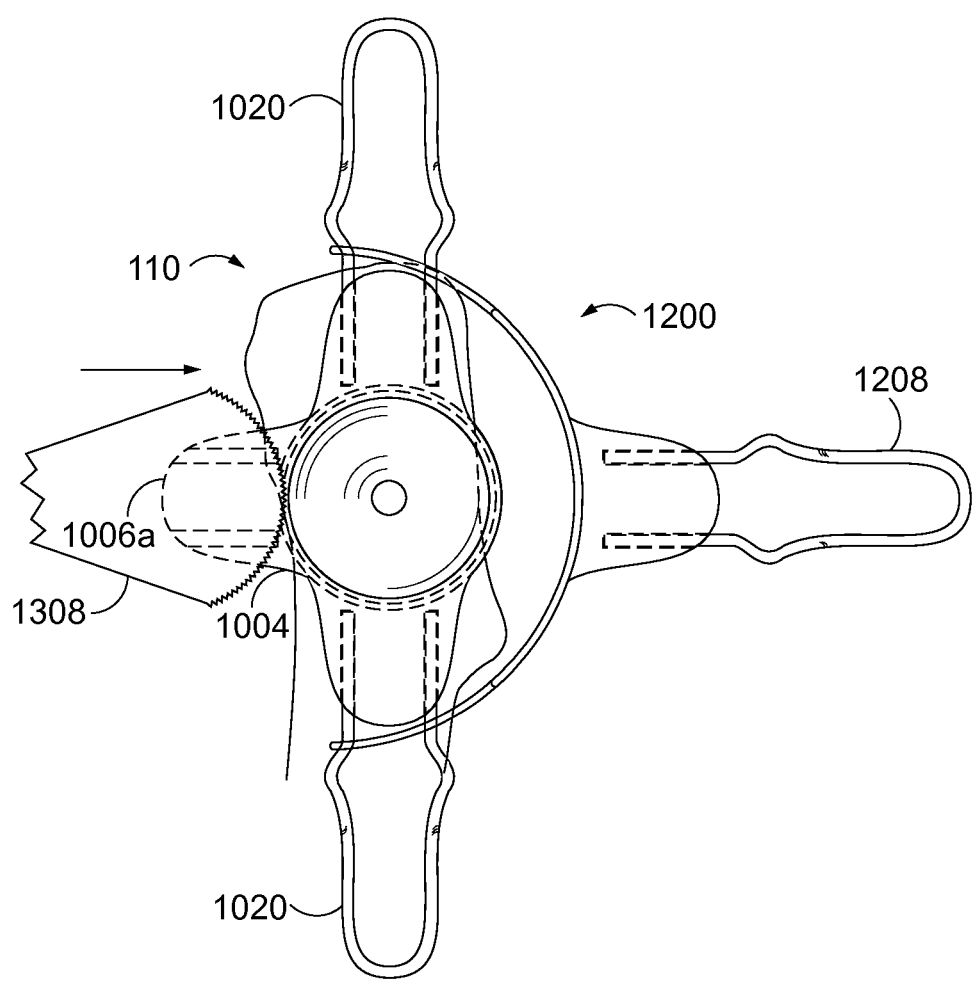
FIG. 13B is a top view of the soft tissue protector seated partially over the saw guide and positioning of a standard saw blade which, attached to a surgical oscillating saw, is advanced towards the femoral head as indicated with the bottom edge of the saw blade parallel and in direct contact with top of the saw guide, allowing a straight femoral head osteotomy parallel to the top edge of the saw guide according to the present invention.

FIG. 13A is a front perspective view further illustrating final placement of the saw guide with two removable angled handles attached. A sterile surgical cloth or another suitable material can be dampened with saline and placed peripherally around the femoral neck during use of the surgical saw in order to contain bone debris. Gentle downward pressure can be applied to keep the saw guide well seated to the underlying bone surface. FIG. 13B is a top view of the soft tissue protector 1200 which, when used, can be positioned partially over the removable angled handles of the saw guide. The soft tissue protector is seated with its curved protector aspect between the femoral head and the local soft tissue structures and can be positioned partially over the removable angled handles. While shielding the soft tissues during the next step involving the surgical saw, it can be used to provide simultaneous gentle retraction of the soft tissues using the fixed angled handle 1208. A surgical oscillating saw blade 1308, attached to a standard surgical oscillating saw (not illustrated), can be positioned with its undersurface against the top front surface of the saw guide, front platform 1006a. Alternately, the other platforms of the saw guide can also be used for the proximal osteotomy procedure, if desired. The surgical oscillating saw is positioned with the bottom surface of the saw blade resting parallel to and seated along the top surface of the front platform. The surgical saw is activated and advanced towards the exposed cancellous bone of the femoral head above the saw guide, with the platform providing a stabile base, as illustrated. Saline solution can be applied using a syringe to provide additional lubrication and cooling for the oscillating saw blade as it oscillates along the top surface of the saw guide. The oscillating saw is advanced as indicated until the proximal osteotomy is completed. A femoral head osteotomy is created parallel to the top edge of the saw guide, thereby creating the proximal osteotomy 180. Thus, the platforms of the saw guide are used for providing flat surfaces for the oscillating saw blade to rest and oscillate against, during the proximal osteotomy procedure, creating a flat and precise proximal osteotomy 180.

Figures 14A, 14B:
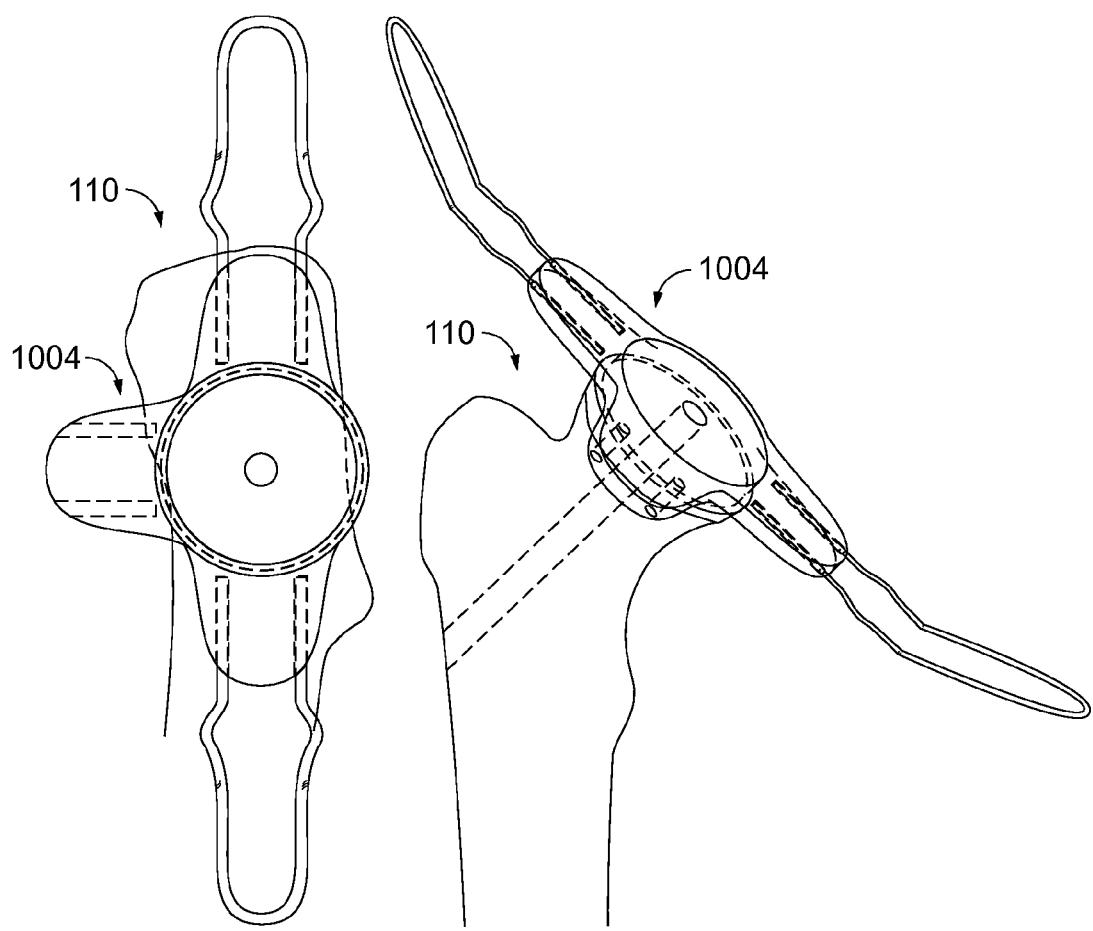
FIG. 14A is a top view the saw guide and bone cuts following oscillating saw use according to the present invention.
FIG. 14B is a front perspective view of the saw guide further illustrating the bone cuts following oscillating saw use according to the present invention.
Figures 14C, 14D, 14E:
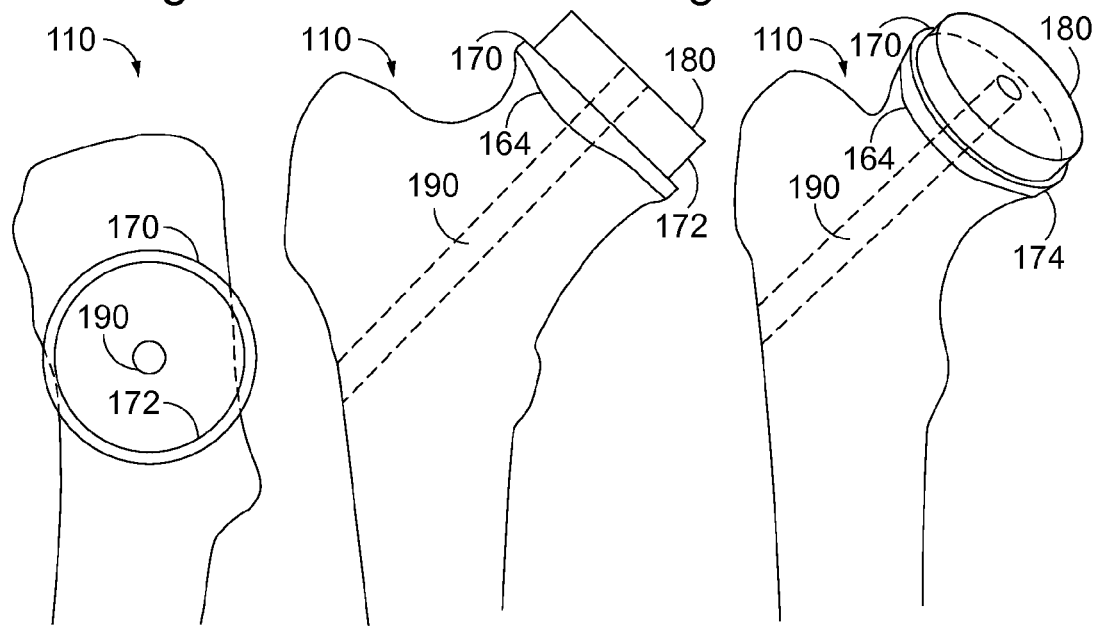
FIG. 14C is a top perspective view of the proximal femur with the saw guide removed further illustrating the osteotomies of the femoral head and the central bone channel according to the present invention.
FIG. 14D is a front view of the proximal femur illustrating the cylindrical osteotomy, central bone channel, distal osteotomy, and proximal osteotomy according to the present invention.
FIG. 14E is a front perspective view of the proximal femur further illustrating the bone cuts and central bone channel according to the present invention.

FIG. 14A is a top view of the saw guide 1004 and completed bone cuts, including the proximal osteotomy, and previous cylindrical reaming and associated simultaneous central bone channel drilling. FIG. 14B is a front perspective view of the saw guide further illustrating the bone cuts following oscillating saw use. Use of the saw guide during this procedure leads to a reliably flat and straight proximal osteotomy at a precise height. FIGS. 14C, 14D and 14E are a top perspective view, front view and front perspective view, respectively, of the proximal femur 110 further illustrating the resultant bone cuts following the prior procedures: cylindrical osteotomy 172 and distal osteotomy 170, central bone channel 190, and proximal osteotomy 180.

Figure 15A:
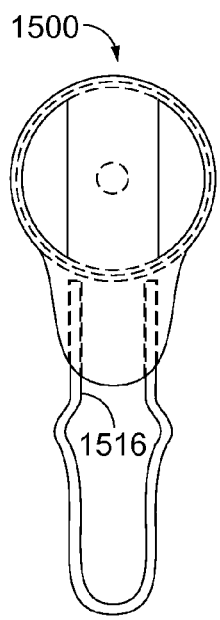
FIG. 15A is a top view illustrating a hip retractor, in accordance with one exemplary embodiment of the present invention.
Figure 15B:
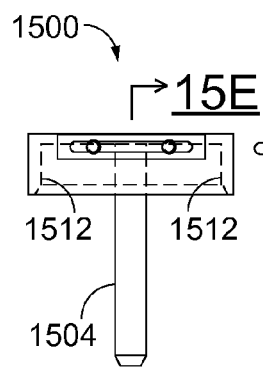
FIG. 15B is a front view of the hip retractor shown in FIG. 15A.
Figure 15C:
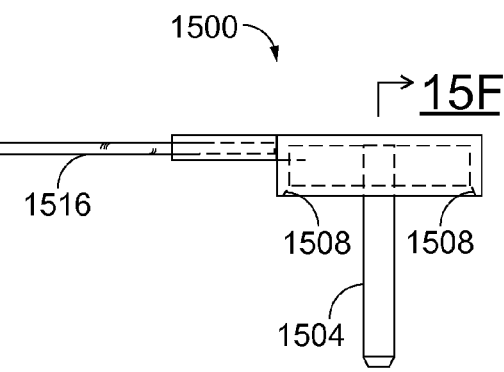
FIG. 15C is a right view of the hip retractor shown in FIG. 15A.

FIG. 15A is a top view illustrating various aspects of a hip retractor 1500, in accordance with one exemplary embodiment of the present invention. This surgical instrument can aid in hip retraction during placement of the acetabular component, if desired, and also helps shield the cancellous bone of the femoral head following cylindrical reaming and simultaneous central bone channel drilling and proximal osteotomy completion. Joined centrally to the base of the upper aspect of the hip retractor is a post 1504, which inserts into the central bone channel created after cylindrical reaming with simultaneous central bone channel drilling, and proximal osteotomy completion. The post has a beveled lower edge as illustrated. FIGS. 15B and 15C are a front view and a right view, respectively, of the hip retractor. Joined at the top of the post is the upper section of the hip retractor which seats to the femoral head following all osteotomies. The cylindrical inner edge 1512 transitions to a beveled lower edge 1508 at the base making seating easier. The hip retractor has a non-removable, fixed flat handle 1516 to aid manual retraction. The fixed flat handle is welded into place in this exemplary embodiment but may be formed as cast in alternate embodiments. There are bent ridges along the surface of the fixed flat handle, as illustrated, which can be helpful for gripping the handle.

Figure 15D:
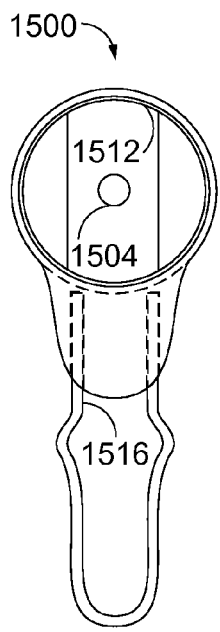
FIG. 15D is a bottom view of the hip retractor shown in FIG. 15A.
Figure 15E:
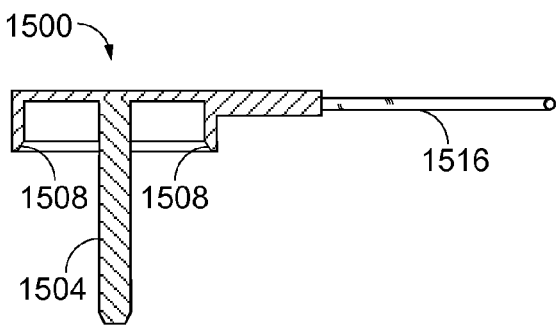
FIG. 15E shows a cross-sectional left view of the hip retractor shown in FIG. 15A, as indicated by line 15E-15E in FIG. 15B.
Figure 15F:
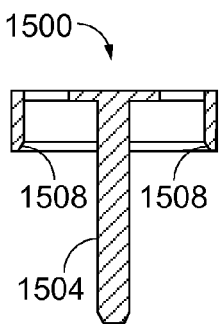
FIG. 15F shows a cross-sectional front view of the hip retractor shown in FIG. 15A, as indicated by line 15F-15F in FIG. 15C.

FIG. 15D is a bottom view of the hip retractor further illustrating its inner surfaces. FIG. 15E shows a cross-sectional left view of the hip retractor as indicated by line 15E-15E in FIG. 15B. FIG. 15F shows a cross-sectional front view of the hip retractor, as indicated by line 15F-15F in FIG. 15C, further illustrating its inner surfaces and beveled lower edge 1508. The top surface includes windows on its outer edges as illustrated, which can provide additional visualization of instrument seating to the cancellous bone during use. The top surface also has a central section, in between the windows, which includes a planar surface, as illustrated. This central section is designed to cover the cancellous bone between the windows. The hip retractor can be produced in two or more heights with respect to the distance between the undersurface of its top surface to the bottom surface of the hip retractor. Choice of hip retractor height should correspond to the selected saw guide height used earlier in the procedure and its associated resultant proximal osteotomy height.

FIG. 16A is a top perspective view of the proximal femur following bone preparation, and illustrating the seated hip retractor 1500 over the cancellous bone of the femoral head and seated with its beveled lower edge in contact with the underlying bone surface along the distal osteotomy and the post 1504 within the central bone channel. The post is joined to the upper aspect of the hip retractor and helps to further transmit forces through the femoral head and neck during manual retraction. The fixed flat handle 1516 is used for both maintenance of seating and for applying hip retraction. Seating can be confirmed visually ensuring the bottom surface of the hip retractor is in contact with the femoral head cortical bone at the distal osteotomy and also can be visualized through the windows along the top surface by examining its positioning relative to the underlying cancellous bone. Once fully seated, as illustrated, gentle hip retraction can be applied if needed during preparation of the acetabulum for placement of the acetabular cup component. The central section at the upper aspect of the hip retractor, between the windows, helps shield the cancellous bone of the femoral head from impact with surgical instruments, as the cancellous bone is partially covered during use of the hip retractor. Care is taken to ensure the hip retractor is fully seated throughout use by applying gentle downward pressure using the handle. FIG. 16B is a front view further illustrating the hip retractor seated onto the femoral head. FIG. 16C is a front perspective view further illustrating the hip retractor seated onto the femoral head. The hip retractor can be produced in multiple size options including the post 1504 being manufactured in multiple lengths for differing applications. At times the central bone channel is drilled to a shorter depth that does not reach the lateral cortex of the femoral shaft. This decision is dependent on implant choice with the associated modular hip resurfacing system as further detailed herein. The length of cannulated cylindrical reamer drill base 616 used in the modular cannulated cylindrical reamer assembly 710 determines the depth of the central bone channel. A hip retractor with a longer post may be used in applications with longer central bone channels. Thus, choice of a specific hip retractor can be based upon the selected application.

FIG. 17A is a top view illustrating various aspects of an outer hole drill guide 1700, in accordance with one exemplary embodiment of the present invention. This surgical instrument aids in the precise placement of guide pins parallel to the central bone channel for the subsequent drilling of outer holes using cannulated drill bits in order to drill outer holes for some applications of the modular hip resurfacing system according to the present invention. Centrally joined along the base of the upper surface of the upper aspect of the outer hole drill guide is a post 1704, which is designed to insert into the central bone channel created after cylindrical reaming and simultaneous central bone channel drilling following all osteotomies. This post has a beveled lower edge as illustrated. Joined at the top of the post is the upper section of the outer hole drill guide which seats to the femoral head. There are two raised drill guides 1718 joined to the upper aspect of the outer hole drill guide. Each of the raised drill guides 1718 has a drill guide hole 1720, which passes completely through the undersurface of the drill guide. FIGS. 17B and 17C are a front view and a right view, respectively, of the outer hole drill guide. The cylindrical inner edge 1712 transitions to a beveled lower edge 1708 at the base making seating easier. The outer hole drill guide has a non-removable, fixed flat handle 1716 to aid seating and retraction, as needed. There are bent ridges along the surface of the fixed flat handle, as illustrated, which can be helpful for gripping the handle. The fixed flat handle is welded into place in this exemplary embodiment but may be formed as cast in alternate embodiments. FIG. 17D is a bottom view of the outer hole drill guide further illustrating the inner surfaces. FIG. 17E shows a cross-sectional left view of the outer hole drill guide as indicated by line 17E-17E in FIG. 17B. FIG. 17F shows a cross-sectional front view of the outer hole drill guide, as indicated by line 17F-17F in FIG. 17C, further illustrating its inner surfaces including the raised drill guides 1718 and drill guide holes 1720. The top surface includes windows on its outer edges as illustrated, which can provide additional visualization of instrument seating to the cancellous bone during use. The top surface also has a central section, in between the windows, which includes a planar surface. This central section is designed to cover the cancellous bone between the windows. This central section also includes the two raised drill guides, as illustrated. The outer hole drill guide can be produced in two or more heights with respect to the distance between the undersurface of its top surface to the bottom surface of the outer hole drill guide. Choice of outer hole drill guide height will correspond to the selected saw guide height used earlier in the procedure and its associated resultant proximal osteotomy height. The outer hole drill guide can be produced in multiple size options including the post 1704 being manufactured in multiple lengths for differing applications based on associated central bone channel depth.

Figures 18A, 18B:
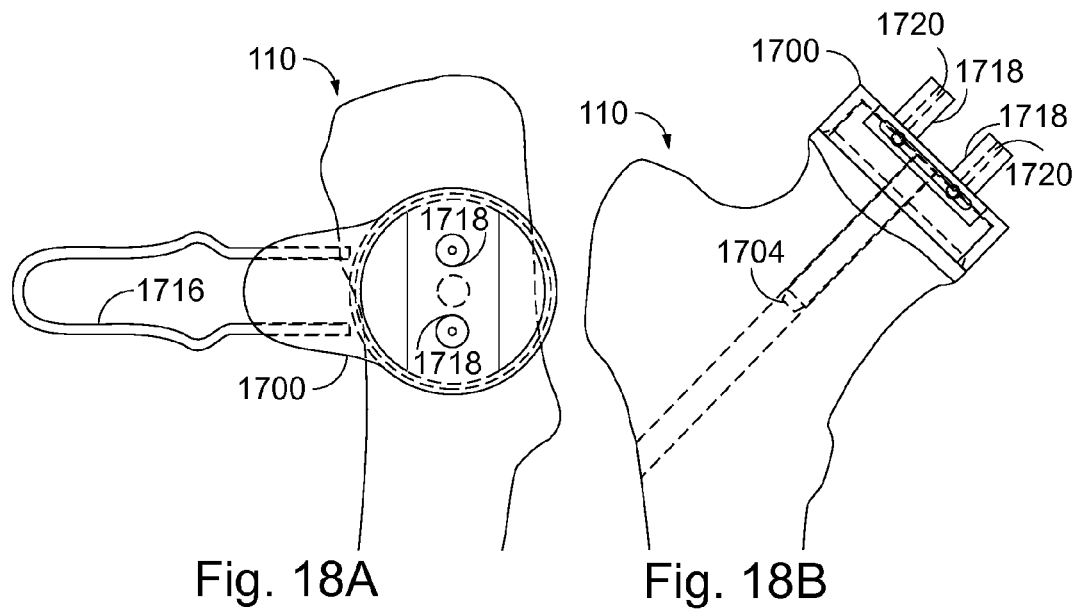
FIG. 18A is a top view of the seated outer hole drill guide, following the osteotomies and central bone channel creation according to the present invention.
FIG. 18B is a front view further illustrating the seated outer hole drill guide according to the present invention.
Figures 18C, 18D:
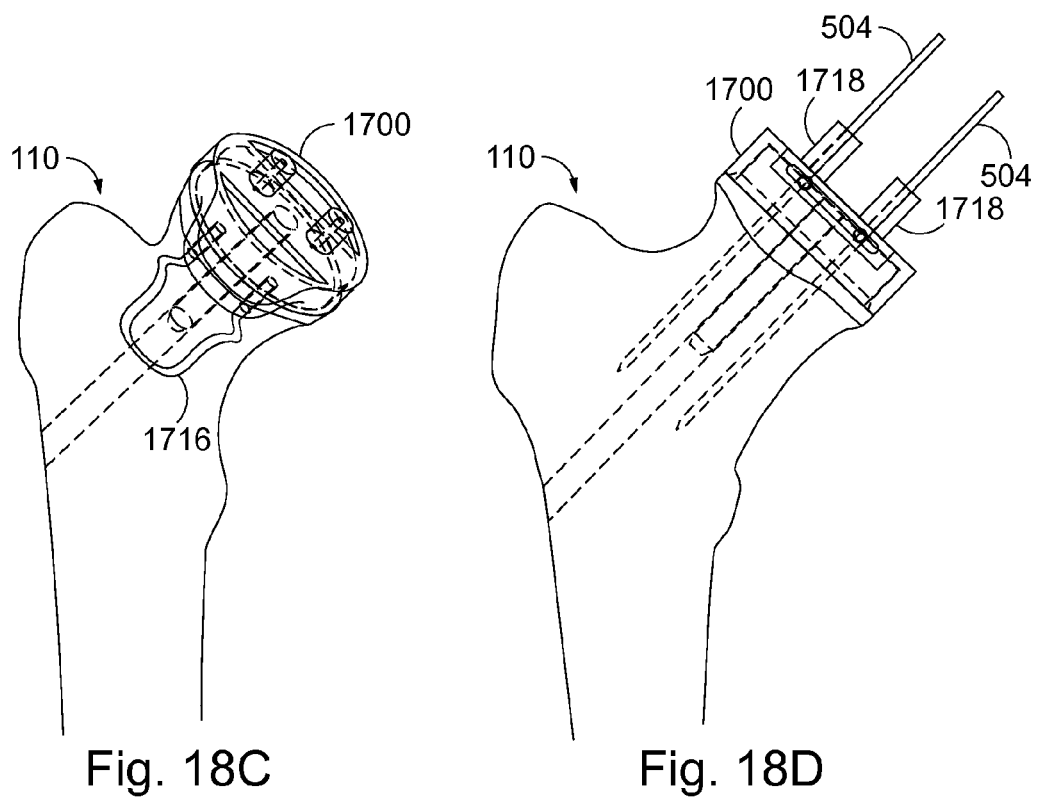
FIG. 18C is a front perspective view, further illustrating the seated outer hole drill guide according to the present invention.
FIG. 18D is a front view illustrating proximal and distal guide pins inserted for precise drilling of outer holes according to the present invention.

FIGS. 18A and 18B are top and front views, respectively, of the seated outer hole drill guide 1700, following the osteotomies and central bone channel drilling. Seating can be confirmed visually ensuring the bottom surface of the outer hole drill guide is in contact with the femoral head cortical bone at the distal osteotomy and also can be visualized through the windows along the top surface by examining its positioning relative to the cancellous bone. The outer hole drill guide is used when the modular options are selected requiring additional drilling of outer holes. The modular hip resurfacing system according to the present invention includes applications not requiring drilling of additional outer holes, as well as applications requiring drilling of one or two outer holes, as detailed in the exemplary embodiments herein. The outer hole drill guide is positioned into place, with its post 1704 inserted into the central bone channel, as illustrated. The outer hole drill guide is properly oriented and seated when the raised drill guides 1718 are at the superior and inferior aspects of the femoral head so that they are centrally located relative to the femoral shaft and lateral cortex, as illustrated. Intraoperative fluoroscopic imaging can be performed in multiple imaging planes to further confirm proper seating. FIG. 18C is a front perspective view, further illustrating the seated outer hole drill guide. Proper seating can be further confirmed by checking its relative positioning along the underlying bone surface at the distal osteotomy and through the windows along its upper surface. The central section at the upper aspect of the outer hole drill guide, between the windows, helps shield the cancellous bone of the femoral head from impact with surgical instruments, as the cancellous bone is partially covered during use of the outer hole drill guide. Once the outer hole drill guide is properly positioned, a k-wire, guide pin 504 can be inserted into each guide pin hole 1720, as needed, using a surgical pin driver or surgical drill. FIG. 18D is a front view illustrating proximal and distal guide pins inserted for precise drilling of two outer holes. Longer guide pins may be used and can be inserted to a greater depth, passing through the lateral cortex depending on the specific application requirements.

Figures 19A, 19B, 19C, 19D:
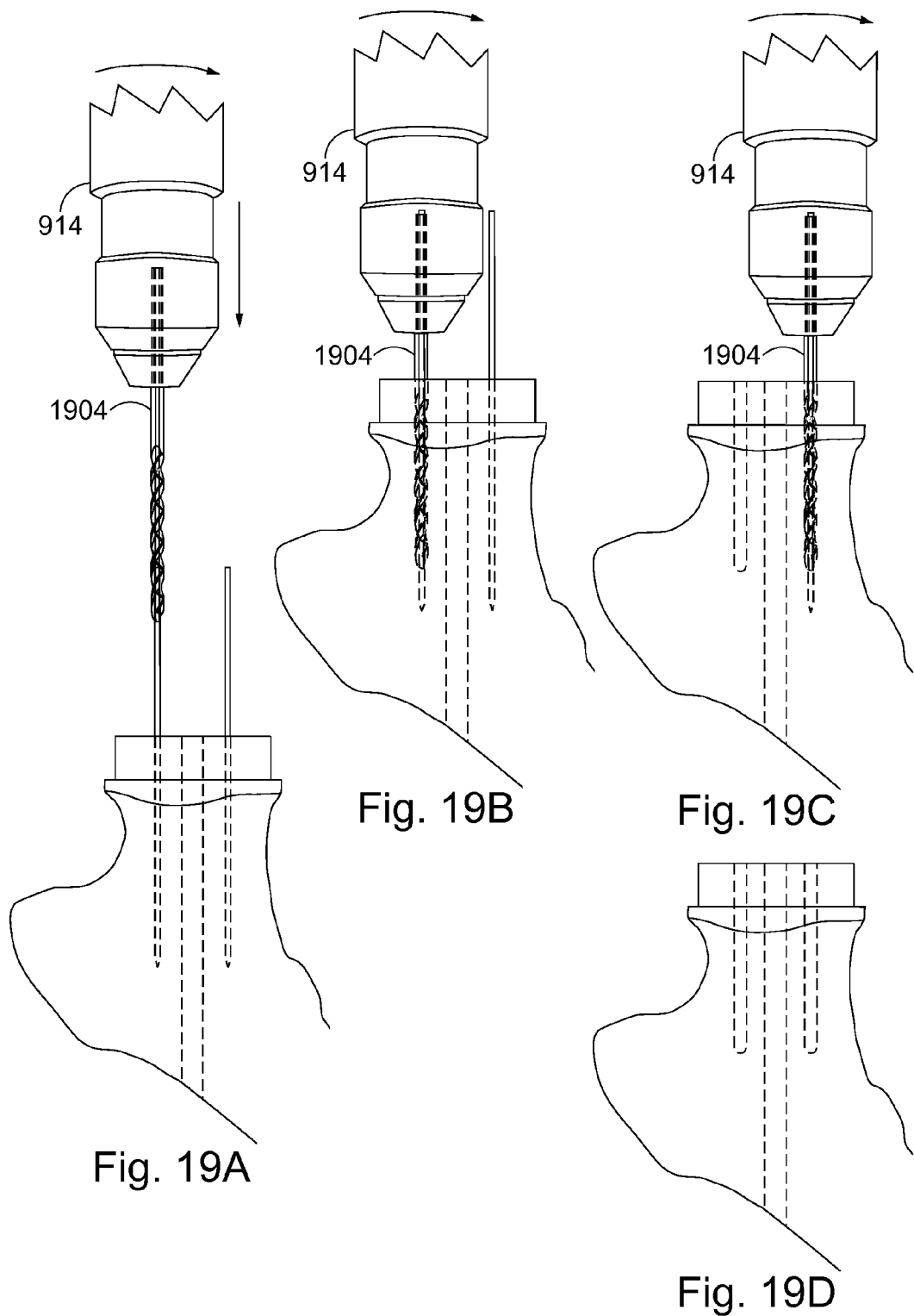
FIG. 19A is a front view illustrating placement of a surgical cannulated drill bit, which is attached to a surgical drill, over the proximal guide pin according to the present invention.
FIG. 19B is a front view illustrating advancement of the cannulated drill bit over the proximal guide pin according to the present invention.
FIG. 19C is a front view illustrating advancement of the cannulated drill bit over the distal guide pin according to the present invention.
FIG. 19D is a front view illustrating the resultant drill holes following drilling over the proximal and distal guide pins according to the present invention.

FIG. 19A is a front view illustrating placement of a surgical cannulated drill bit 1904, attached to a surgical drill 914, which is partially illustrated, over the proximal guide pin. The surgical drill is activated and advanced downwards until the desired drill depth is reached, depending on specific application requirements. FIG. 19B is a front view illustrating completed advancement of the cannulated drill bit over the proximal guide pin, and FIG. 19C is a front view illustrating completed advancement of the cannulated drill bit over the distal guide pin. FIG. 19D is a front view illustrating the drill holes following drilling over the proximal and distal guide pins.

FIG. 20A is a front view illustrating various aspects of a modular hip resurfacing implant 2010, in accordance with one exemplary embodiment of the implant according to the present invention. The modular hip resurfacing implant allows for modular attachment of multiple threaded accessories to increase fixation in the setting of bone deficiencies. This implant includes an upper, cap portion 2012 and a lower, central stem portion 2020. The non-removable, fixed, central stem is attached to the modular hip resurfacing implant and centrally joined to the undersurface of the cap portion.

The modular hip resurfacing implant may be produced with central stems of varying lengths to accommodate anatomic variability in femoral neck length between patients and for varying applications, as needed. FIG. 20B is a cross-sectional left view of the modular hip resurfacing implant as indicated by line 20B-20B in FIG. 20A. The central stem also has an internally threaded, central stem threaded hole 2030 at the lower aspect of its stem. FIG. 20C is a right view of the modular hip resurfacing implant. FIG. 20D is a cross-sectional front view of the modular hip resurfacing implant, as indicated by line 20D-20D in FIG. 20C.

FIG. 20E is a bottom view of the modular hip resurfacing implant further illustrating the undersurface of the implant. FIG. 20F is a bottom perspective view of the modular hip resurfacing implant further showing its undersurfaces. FIG. 20G is an enlarged bottom perspective view of the modular hip resurfacing implant in detail, as indicated by the dashed circle around FIG. 20F. Following preparation of the proximal femur, the central stem of the implant inserts into the central bone channel 190 and the outer planar surface 2060 seats onto the planar surface created by the distal osteotomy 170, with this surface including cortical and cancellous bone. Both the central rim 2038 and inner rim 2040 can provide for additional stability for the modular hip resurfacing implant by further constraining its movement.

As described, the articular rim of the femoral head and a cortical collar of bone proximal to it is preserved with the modular hip resurfacing system according to the present invention. Thus a collar of dense, strong cortical bone above the articular rim remains. The outer, bearing surface of the cap portion of the implant extends just beyond a hemispherical shape, as illustrated. This area beyond equator is comprised of the inner rim 2040 and outer rim 2050. The inner rim surrounds the collar of cortical bone of the femoral head following the osteotomies, above the articular rim. This collar of dense, cortical bone of the femoral head can provide additional peripheral support along the inner rim of the implant.

The undersurface of the cap portion has two internally threaded, implant threaded holes 2080. In applications utilizing the implant threaded holes for modular threaded attachments, with typically one implant threaded hole oriented superiorly relative to the most proximal aspect of the femoral neck and the other oriented inferiorly relative to the most distal aspect of the femoral neck. These implant threaded holes are located along the undersurface of the upper aspect, cap portion 2012, as illustrated. The modular hip resurfacing implant allows multiple modular fixation options using its multiple modular attachment points which include the central stem threaded hole and the two implant threaded holes. In the setting of decreased bone quality, additional modular threaded attachments can be used to supplement implant fixation.

The outer surface of the cap portion has a bearing surface 2090. The modular hip resurfacing implant can be produced with varying cap portion diameters to accommodate anatomical differences of femoral head sizes. Various size options for the modular hip resurfacing implant include cap portions sized from 38 mm to 56 mm in 2 mm increments, with additional sizes for custom applications as needed. The cap portion can be produced in multiple diameters by decreasing or increasing, respectively, the distance between the central rim 2038 and outer rim 2050. This is accomplished by making the entire cap portion larger while retaining the substantially hemispherical shape of its bearing surface, as the entire outer surface is enlarged accordingly. The stepped shape of the undersurface of the implant can be present in all available femoral head diameters for the implant, matching the associated stepped cylindrical femoral head osteotomies.

Along the bottom edge of the bearing surface is the outer rim 2050, which surrounds the remaining femoral head cortex following all osteotomies of the femoral head, including completion of the stepped cylindrical femoral head osteotomies and final implant seating. The outer rim has a fillet edge at its base, as illustrated, for improved bearing surface articulation and may also be polished as with the rest of the bearing surface. The outer, cortical surfaces of the remaining cortical rim of the femoral head provide additional stability along the implant-bone interface. A porous, textured, granular and/or beaded surface may be used on all undersurfaces and on the central stem of the modular hip resurfacing implant for promotion of bony ingrowth at the interface of the implant and bone, as is known in the art. This porous surface is present on the implant at the interface of the implant and femoral bone. The porous surface provides additional construct strength over time with development of bony ingrowth. The undersurfaces and central stem may also include a hydroxy apatite coating to further promote bone ingrowth. The inner planar surface 2070 of the modular hip resurfacing implant seats to the cylindrical planar surface of the remaining cancellous, trabecular, spongy bone of the femoral head following the stepped cylindrical femoral head osteotomies, specifically the proximal osteotomy 180. The central rim 2038 is situated between the outer planar surface 2060 and the inner planar surface 2070.

The modular hip resurfacing implant including its fixed stem may be manufactured using a high carbon cobalt chrome (CoCr) alloy. The modular hip resurfacing implant may also be made of an alternate metal or metal alloy including stainless steel, titanium, or another suitable material. The central stem, and cap portion of the implant may be manufactured as cast or using additional standard techniques including injection molding or forging. The central stem and cap portion of the implant may be manufactured separately and welded together or otherwise joined. In that case, a central hole can be present in the femoral head portion of the implant where the central stem may be inserted and joined using welding processes, or welding processes in addition to use of threading or other standard methods of joining metal, as is known in the art.

FIG. 21A is a top view illustrating various aspects of a one-hole plate 2110. FIGS. 21B, 21C, 21D and 21E are left, front, right and bottom views, respectively, further illustrating the one-hole plate and a central hole 2112. FIG. 21F is a top view illustrating various aspects of a two-hole plate 2120. FIGS. 21G, 21H, 21I and 21J are left, front, right and bottom views, respectively, further illustrating the two-hole plate, central hole 2112, and an outer hole 2122. FIG. 21K is a front view illustrating various aspects of a three-hole plate 2130. FIGS. 21L, 21M, 21N, and 21O are left, front, right and bottom views, respectively, further illustrating the three-hole plate, central hole 2112, and two outer holes 2122. The one-, two-, and three-hole plates are used for some modular configurations of the modular hip resurfacing system according to the present invention, as detailed herein.

FIGS. 22A, 22B and 22C are top, front, and bottom views illustrating various aspects of a central screw 2210, which can be produced in varying lengths. FIGS. 22D, 22E and 22F are enlarged bottom, enlarged front and enlarged bottom views of the central screw, in detail, as indicated by dashed circles in FIGS. 22A, 22B, and 22C, respectively. FIGS. 22G and 22H are front and bottom views, respectively, of an independent central screw 2214, which can be produced in varying lengths. FIGS. 22I and 22J are front and bottom views, respectively, of an independent outer screw 2215, which can be produced in varying lengths. FIGS. 22K and 22L are front and bottom views of a threaded central cap 2216, which can be produced in varying lengths. FIGS. 22M and 22N are front and bottom views, respectively, of an outer peg 2218, which can be produced in varying lengths. FIGS. 22O and 22P are enlarged front and enlarged bottom views, respectively, of the outer peg screw in detail, as indicated by dashed circles in FIGS. 22M and 22N. FIGS. 22Q and 22R are front and bottom views, respectively, of an outer screw 2222, which can be produced in varying lengths. FIGS. 22S and 22T are front and bottom views, respectively, of a cortical screw 2224, which can be produced in varying lengths. The aforementioned screws are used for various exemplary embodiments of the modular hip resurfacing system according to the present invention, as detailed herein.

FIG. 23A is an exploded bottom perspective view illustrating placement of the modular hip resurfacing 2010 implant, one-hole plate 2110, and central screw 2210 into the prepared proximal femur 110, in accordance with one exemplary modular configuration of the present invention.

The stepped cylindrical femoral head osteotomies and drilling of the central bone channel through the lateral femoral cortex are completed prior to implantation.

The central stem of the modular hip resurfacing implant is inserted into the central bone channel and the implant is seated. The one-hole plate is placed onto the lateral femoral cortex and a central screw is inserted through the plate into the central bone channel and twisted, engaging the central stem threaded hole 2030, with the plate oriented along the femur as illustrated. Central screw tightening is completed once the modular hip resurfacing implant is fully seated, and the central screw is tightly secured into the central stem threaded hole.

FIG. 23B is a bottom perspective view following placement of the modular hip resurfacing implant, one-hole plate and central screw. FIG. 23C is a cross-sectional right view, as indicated by line 23C-23C in FIG. 23B, further illustrating the construct. Final seating is illustrated of the modular hip resurfacing implant with the central screw securely tightened. The one-hole plate is positioned below the greater trochanter 132.

Implantation of this exemplary modular configuration of the hip resurfacing system may be accomplished through the following steps. A posterior surgical approach to the hip joint is performed and the lateral cortex of the femur is exposed for access. The soft tissues are elevated just distal to the greater trochanter where the plate can be seated onto the lateral cortex. The hip is surgically dislocated posteriorly following a standard capsulotomy and careful capsular release in standard fashion for hip resurfacing arthroplasty. The stepped cylindrical femoral head osteotomies are performed, as described and illustrated in FIGS. 3A to 3B, 4A to 4C, 5A to 5B, 7A to 7B, 8A to 8B, 11A to 11B, and 13A to 13B, with the central bone channel being fully drilled through the lateral cortex. Preparation for placement of a standard acetabular component, which is proportionally sized, is undertaken and the acetabular component is implanted, as routinely performed for hip resurfacing arthroplasty.

Following osteotomies and central bone channel drilling, the articular cartilage, overlying the remaining collar of femoral head cortical bone above the articular rim, is excised using standard surgical instruments including scalpels. This is performed while leaving the remaining femoral head cortical bone intact. This step allows increased cortical contact at the interface of the outer rim and the remaining femoral head cortex following all osteotomies.

The modular hip resurfacing implant is fully inserted into the central bone channel with an implant threaded hole oriented towards the remaining superior anatomic cortex of the femoral head. The one-hole plate is placed on the lateral cortex and the central screw is inserted through the plate and twisted, engaging the central stem threaded hole. The modular hip resurfacing implant is fully seated once its inner and outer planar surfaces are mated to the osteotomized surfaces of the femoral head and the central screw is tightly secured into the central stem threaded hole, as illustrated in FIG. 23C. The implant is mated to both the cortical bone 2310 and cancellous bone 2312.

The resurfaced hip is relocated into the acetabular component and the hip capsule closed, in standard fashion for hip resurfacing, and the deep and superficial soft tissues are then sutured. This exemplary modular configuration is beneficial in the setting of good bone quality in the superior and inferior femoral head, and the plate and central screw provide strong fixation, with the plate on the lateral cortex acting as a further buttress.

The exemplary modular configuration illustrated in FIGS. 24A to 24C is the same as that illustrated in FIGS. 23A to 23C with a few differences, which are described below. FIG. 24A is an exploded bottom perspective view illustrating placement of the modular hip resurfacing implant 2010, three-hole plate 2130, two outer screws 2222, and a central screw 2210, into the prepared proximal femur 110, in accordance with another exemplary modular configuration. FIG. 24B is a bottom perspective view, and FIG. 24C is a cross-sectional right view, as indicated by line 24C-24C in FIG. 24B, further illustrating the final construct.

The steps required for implantation are the same as those described with reference to FIGS. 23A to 23C with the following few differences. Two additional holes are drilled in order to accommodate two outer screws using the outer hole drill guide 1700 with placement of guide pins, as described and illustrated in FIGS. 18A to 18D and 19A to 19D. These drilled holes align with the implant threaded holes and are parallel to the central bone channel. Further, the holes are drilled with a long standard surgical cannulated drill bit attached to a surgical drill, and are drilled completely through the lateral cortex of the femur to allow full insertion of the two outer screws.

The modular hip resurfacing implant is inserted into the central bone channel with an implant threaded hole oriented toward the superior most aspect of the remaining femoral head cortex. A three-hole plate is placed on the lateral cortex and two outer screws are inserted through the top and bottom holes of the plate. The outer screws are partially tightened after engaging the threads of the implant threaded holes. Then the central screw is inserted engaging the central stem threaded hole 2030 and is tightened. Full tightening of the outer screws is then completed.

The outer screws provide further resistance to rotational forces during central screw tightening. The outer screws also provide additional fixation in the setting of decreased bone quality. The modular hip resurfacing implant is fully seated, with the central screw tightly secured into the central stem threaded hole. The outer screws are also tightly secured. The implant is mated to both the cortical bone 2310 and cancellous bone 2312.

The resurfaced hip is relocated into the acetabular component and the hip capsule closed, in standard fashion for hip resurfacing, and the deep and superficial soft tissues are then sutured. This exemplary modular configuration is beneficial in the setting of decreased bone quality in the superior and inferior femoral head and neck as the outer screws in combination with the three-hole plate and central screw provide strong fixation, and the plate on the lateral cortex acts as a further buttress.

The exemplary modular configuration illustrated in FIGS. 25A to 25C is the same as that illustrated in FIGS. 24A to 24C with a few differences, which are described below. FIG. 25A is an exploded bottom perspective view illustrating placement of the modular hip resurfacing implant 2010, one outer peg 2218, two-hole plate 2120, one outer screw 2222, and a central screw, into the prepared proximal femur 110, in accordance with another exemplary modular configuration. FIG. 25B is a bottom perspective view, and FIG. 25C is a cross-sectional right view, as indicated by line 25C-25C in FIG. 25B, further illustrating the final construct.

The steps for implantation are the same as those described with reference to FIGS. 24A to 24C with the following differences. The bottom outer hole to be drilled, which corresponds with the bottom implant hole, is drilled to a shorter depth to match the chosen length of the outer peg 2218. This process is performed using the outer hole drill guide and surgical cannulated drill bit attached to a surgical drill, as described and illustrated in FIGS. 18A to 18D and 19A to 19D. This bottom hole accommodates the outer peg once secured to the implant threaded hole 2080 of the modular hip resurfacing implant. The outer pegs can be produced in various sizes to accommodate anatomic variability and application. The corresponding hole is drilled parallel to the central bone channel to be precisely oriented for proper seating when the outer peg attached to the modular hip resurfacing implant is fully inserted. A standard surgical drill depth gauge can be used to aid in this step. The depth of the drill hole matches the depth of the peg to be used. An additional hole is drilled above the central bone channel, through the lateral femoral cortex using the outer hole drill guide. This additional hole accommodates an outer screw corresponding with the top implant threaded hole, as described in FIGS. 24A to 24C.

Multiple lengths of outer pegs can be available allowing selection based upon anatomic variation in femoral neck length and underlying bone degenerative hip joint disease. As such, outer pegs are sized to extend past the femoral neck approximately to the inter-trochanteric ridge. In this mode, the outer peg bypasses the femoral neck, further shielding it from stress concentration allowing stresses to be transmitted to the femoral shaft. The outer peg is threaded into the bottom implant threaded hole and secured.

The modular hip resurfacing implant with the attached outer peg is inserted into the prepared femur, with the outer peg oriented towards the inferior most aspect of the remaining femoral head cortex. A two-hole plate is placed onto the lateral femoral cortex just below the greater trochanter, as illustrated, and one outer screw 2222 is inserted through the upper plate hole. The outer screw is partially tightened after engaging the threads of the implant threaded hole. Then the central screw is inserted through the plate and tightened once engaged into the central stem threaded hole 2030.

Rotational forces are further resisted by the outer screw and outer peg during tightening. The modular hip resurfacing implant is fully seated once its inner and outer planar surfaces are mated to the osteotomized surfaces of the femoral head and the central screw is tightly secured into the central stem threaded hole and the outer screw is tightened. The implant is mated to both the cortical bone 2310 and cancellous bone 2312.

The resurfaced hip is relocated into the acetabular component and the hip capsule is closed in standard fashion with sutures and the deep and superficial soft tissues are then sutured. This exemplary modular configuration is beneficial in the setting of decreased bone quality in the superior femoral head and neck, for example in the setting of mild bone deficiency of the superior femoral head. The upper outer screw in combination with the 2-hole plate, central screw, and lower outer peg provides strongest fixation superiorly and still provides strong fixation inferiorly, and the plate on the lateral cortex acts as a further buttress.

The exemplary modular configuration illustrated in FIGS. 26A to 26C is the same as that illustrated in FIGS. 25A to 25C with a few differences described below. FIG. 26A is an exploded bottom perspective view illustrating placement of the modular hip resurfacing implant 2010, two outer pegs 2218, one-hole plate 2110, and a central screw 2210 into the prepared proximal femur 110, in accordance with another exemplary modular configuration. FIG. 26B is a bottom perspective view, and FIG. 26C is a cross-sectional right view, as indicated by line 26C-26C in FIG. 26B, further illustrating the final construct.

The steps for implantation are the same as those described with reference to FIGS. 25A to 25C with a few differences described below. The upper and lower outer holes are drilled to accommodate two outer pegs using the outer hole drill guide 1700 above and below the central bone channel and are drilled to match the length of the selected outer pegs. The selected outer pegs are threaded into the top and bottom implant threaded holes and tightly secured. The modular hip resurfacing implant is inserted into the prepared proximal femur, sliding the central stem with attached outer pegs into the corresponding holes in the femoral head, as configured.

The modular hip resurfacing implant is seated. A one-hole plate is placed on the lateral cortex. Then the central screw is inserted through the plate into the central bone channel and twisted, engaging the central stem threaded hole 2030. The modular hip resurfacing implant is fully seated once its inner and outer planar surfaces are mated to the osteotomized surfaces of the femoral head and the central screw is tightly secured into the central stem threaded hole. The implant is mated to both the cortical bone 2310 and cancellous bone 2312. Rotational forces during extended use of the implant are further also resisted by the outer pegs.

The hip is relocated into the acetabular component and the hip capsule is closed in standard fashion with sutures and the deep and superficial soft tissues are then sutured. The upper and lower outer pegs attached to the modular hip resurfacing implant in combination with the one-hole plate and central screw provides strong fixation setting of compromised bone quality in the femoral head and good bone quality in the femoral neck, and the plate on the lateral cortex acts as a further buttress.

The exemplary modular configuration illustrated in FIGS. 27A to 27C is the same as that illustrated in FIGS. 26A to 26C with a few differences described below. FIG. 27A is an exploded bottom perspective view illustrating placement of the modular hip resurfacing implant 2010, two outer pegs 2218, and a threaded central cap 2216 into the prepared proximal femur 110, in accordance with another exemplary modular configuration. FIG. 27B is a bottom perspective view, and FIG. 27C is a cross-sectional right view, as indicated by line 27C-27C in FIG. 27B, further illustrating the final construct.

The steps for implantation are the same as those described with reference to FIGS. 26A to 26C with a few differences described below. The lateral cortex of the femur is not prepared for plate placement, as a plate is not used in this exemplary modular configuration.

The central bone channel is drilled to the depth required for final seating of the modular hip resurfacing implant with the attached threaded central cap, without reaching the lateral cortex. The depth of the central bone channel does not need to extend past the depth required for final seating in this modular configuration. A standard surgical drill depth gauge can be used to further facilitate this step. The upper and lower outer holes are drilled to accommodate two outer pegs, as described in FIG. 26A to 26C. The selected outer pegs are tightly secured into the implant threaded holes. The threaded central cap is tightly secured into the central stem threaded hole 2030. Bone cement is placed along the cancellous bone at the proximal osteotomy to mate with the implant inner planar surface. The modular hip resurfacing implant is inserted, sliding the central stem and attached outer pegs into the corresponding drilled holes, as configured. The modular hip resurfacing implant is inserted, and pressed into place until fully seated. The implant is firmly seated into place as illustrated.

Rotational forces during extended use of the implant are further also resisted by the outer pegs. The modular hip resurfacing implant is fully seated once its inner and outer planar surfaces are mated to the osteotomized surfaces of the femoral head. The resurfaced hip is relocated into the acetabular component and the hip capsule is closed in standard fashion with sutures and the deep and superficial soft tissues are then sutured. The upper and lower outer pegs attached to the modular hip resurfacing implant in combination with the threaded central cap attached to the central stem in this cemented application provides strong fixation in a wide range of bone quality in the femoral head and neck.

The modular configuration illustrated in FIGS. 28A to 28C is the same as that illustrated in FIGS. 27A to 27C with a few differences described below. FIG. 28A is an exploded bottom perspective view illustrating placement of the modular hip resurfacing implant 2010, and a threaded central cap 2216 into the prepared proximal femur 110, in accordance with another exemplary modular configuration. FIG. 28B is a bottom perspective view, and FIG. 28C is a cross-sectional right view, as indicated by line 28C-28C in FIG. 28B, further illustrating the final construct.

The steps for implantation are the same as those described with reference to FIGS. 27A to 27C with a few differences described below. Outer pegs are not used in this modular configuration. A threaded central cap is attached to the central stem threaded hole 2030 and tightly secured. Bone cement is applied as described in FIGS. 27A to 27C and the modular hip resurfacing implant is inserted and pressed into place until fully seated, as described in FIGS. 27A to 27C.

The resurfaced hip is relocated into the acetabular component and the hip capsule is closed in standard fashion with sutures and the deep and superficial soft tissues are then sutured. The modular hip resurfacing implant in combination with the threaded central cap attached to the central stem in a cemented application provides strong fixation in a wide range of bone quality in the femoral head and neck.

The exemplary modular configuration illustrated in FIGS. 29A to 29C is the same as that illustrated in FIGS. 24A to 24C with a few differences described below. FIG. 29A is an exploded bottom perspective view illustrating placement of the modular hip resurfacing implant 2010, three-hole plate 2130, two cortical screws 2224 and the central screw 2210, into the prepared proximal femur 110, in accordance with another exemplary modular configuration. FIG. 29B is a bottom perspective view, and FIG. 29C is a cross-sectional right view, as indicated by line 29C-29C in FIG. 29B, further illustrating the final construct.

The steps for implantation is the same as those described with reference to FIGS. 24A to 24C with a few differences described below. The central stem of the modular hip resurfacing implant is inserted into the central bone channel and fully seated. The central screw is inserted through the three-hole plate. The central screw is twisted, engaging the central stem threaded hole 2030 and is tightened. The modular hip resurfacing implant is fully seated once its inner and outer planar surfaces are mated to the osteotomized surfaces of the femoral head and the central screw is tightly secured into the central stem threaded hole.

Additional holes are drilled from lateral to medial through the outer holes of the three-hole plate. These additional holes are drilled to accommodate two cortical screws and are drilled with guidance from intraoperative fluoroscopic imaging. These holes are drilled parallel with the central bone channel and neck-shaft angle using standard surgical drill and drill bits. Standard surgical instruments are used to retract and shield the soft tissues during drilling and the depth of the hole matches the depth of the chosen length of cortical screw to be used. A standard surgical drill depth gauge can be used to further facilitate this step.

Two cortical screws are inserted through the outer holes of the three-hole plate and tightened. The central screw is checked again to ensure it remains secured to the central stem threaded hole. Cortical screws may vary in length, the application of which depends on individual characteristics of underlying bone quality. In the setting of poor bone quality longer cortical screws are selected to provide increased screw purchase into the cancellous bone. The implant is mated to both the cortical bone 2310 and cancellous bone 2312.

The resurfaced hip is relocated into the acetabular component and the hip capsule is closed in standard fashion with sutures and the deep and superficial soft tissues are then sutured. The modular hip resurfacing implant in combination with the central screw attached to the central stem, three-hole plate and cortical screws provides strong fixation in the setting of good bone quality at the femoral head and diminished bone quality laterally, and the plate on the lateral cortex acts as a further buttress.

The exemplary modular configuration illustrated in FIGS. 30A to 30C is the same as that illustrated in FIGS. 26A to 26C with a few differences described below. FIG. 30A is an exploded bottom perspective view illustrating placement of the modular hip resurfacing implant 2010, two outer pegs 2218, three-hole plate 2130, two cortical screws 2224 and the central screw 2210, into the prepared proximal femur 110, in accordance with another exemplary modular configuration. FIG. 30B is a bottom perspective view, and FIG. 30C is a cross-sectional right view, as indicated by line 30C-30C in FIG. 30B, further illustrating the final construct.

The steps for implantation are the same as those described with reference to FIGS. 26A to 26C with a few differences described below. As described in FIGS. 26A to 26C, two holes are drilled using the outer hole drill guide 1700 above and below the central bone channel in order to accommodate outer pegs. The outer pegs are secured to the modular hip resurfacing implant, and the modular hip resurfacing implant is seated to the proximal femur, accordingly.

The central screw is inserted through the three-hole plate. The central screw is twisted, engaging the central stem threaded hole 2030 and tightened. The modular hip resurfacing implant is fully seated once its inner and outer planar surfaces are mated to the osteotomized surfaces of the femoral head and the central screw is tightly secured into the central stem threaded hole.

Additional holes are drilled from lateral to medial through the outer holes of the three-hole plate. These additional holes are drilled to accommodate two cortical screws and are drilled with guidance from intraoperative fluoroscopic imaging. These holes are drilled parallel with the central bone channel and neck-shaft angle using standard surgical drill and drill bits. Standard surgical instruments are used to retract and shield the soft tissues during drilling and the depth of the hole matches the depth of the chosen length of cortical screw to be used. Shorter screws are used in this exemplary modular configuration as compared to that shown in FIGS. 29A to 29C. These screws are selected, and corresponding holes drilled to a distance where the screws do not meet the outer pegs. A standard surgical drill depth gauge can be used to further facilitate this step.

Two cortical screws are inserted through the outer holes of the three-hole plate and tightened. The central screw is checked again to ensure it remains secured to the central stem threaded hole. The implant is mated to both the cortical bone 2310 and cancellous bone 2312.

The resurfaced hip is relocated into the acetabular component and the hip capsule is closed in standard fashion with sutures and the deep and superficial soft tissues are then sutured. The modular hip resurfacing implant in combination with the central screw attached to the central stem, outer pegs, three-hole plate and cortical screws provides strong fixation in the setting of diminished bone quality in the femoral head along with better bone quality along the femoral shaft and lateral cortex, and the plate on the lateral cortex acts as a further buttress.

The exemplary modular configuration illustrated in FIGS. 31A to 31C is the same as that illustrated in FIGS. 24A to 24C with a few differences described below. FIG. 31A is an exploded bottom perspective view illustrating placement of the modular hip resurfacing implant 2010, an independent central screw 2214 with a washer 3110, and two independent outer screws 2215 with washers 3110, into the prepared proximal femur 110, in accordance with another exemplary modular configuration. FIG. 31B is a bottom perspective view, and FIG. 31C is a cross-sectional right view, as indicated by line 31C-31C in FIG. 31B, further illustrating the final construct.

The steps required for implantation are the same as those described with reference to FIGS. 24A to 24C with a few differences described below. An independent central screw and two independent outer screws are used along with washers without the use of a plate in the current exemplary modular configuration. The femur is prepared with holes drilled in the same manner as described in FIGS. 24A to 24C for placement of the modular hip resurfacing implant, and the modular hip resurfacing implant is seated to the proximal femur, accordingly.

Two independent outer screws with associated washers are inserted, through the top and bottom holes, to be attached to the implant threaded holes. The independent outer screws are partially tightened after engaging the threads of the implant threaded holes. Then a centrally placed independent central screw with a washer is inserted engaging the central stem threaded hole 2030 and is tightened.

The independent outer screws provide further resistance to rotational forces during central screw tightening. The independent outer screws also provide additional fixation in the setting of decreased bone quality. The modular hip resurfacing implant is fully seated, with the independent central screw tightly secured into the central stem threaded hole. The independent outer screws are also tightly secured. The implant is mated to both the cortical bone 2310 and cancellous bone 2312.

The resurfaced hip is relocated into the acetabular component and the hip capsule closed, in standard fashion for hip resurfacing, and the deep and superficial soft tissues are then sutured. This modular configuration is beneficial in the setting of decreased bone quality in the superior and inferior femoral head and femoral head-neck junction as the independent outer screws and independent central screw in combination with washers provide strong fixation, and the fixation to the lateral cortex provides additional construct support acting as a further buttress. This modular configuration may be beneficial in clinical scenarios where washers may be preferred over use of a plate to reduce the overall profile of the lateral construct.

FIG. 32A is a front view and FIG. 32B is a cross-sectional left view, as indicated by line 32B-32B in FIG. 32A, both illustrating various aspects of a two-rib implant 3210, in accordance with another exemplary embodiment of the modular hip resurfacing implant according to the present invention. FIG. 32C is a right view of the two-rib-modular hip resurfacing implant and FIG. 32D is a cross-sectional front view of the two-rib-modular hip resurfacing implant, as indicated by line 32D-32D in FIG. 32C. FIG. 32E is a bottom view of the two-rib-modular hip resurfacing implant further showing its undersurface. The two-rib implant is the same as the implant described in FIGS. 20A to 20G with the following differences. In the present, two-rib exemplary embodiment, the central stem has two equally spaced ribs 3212, circumferentially joined to the top of the central stem, joined to and extending from the undersurface of the cap portion partially downward along the central stem. The ribs are joined to the flat, inner planar surface 2070 of the implant and are also joined to the central stem. They are located at opposite sides of the central stem, at 180 degrees from each other, as illustrated. The ribs extend from the inner planar undersurface of the implant down the central shaft to the level of the outer rim, but may vary in alternate embodiments. The ribs have sharp outer edges to ease implantation. The implant is designed to be inserted into the central bone channel with one of the two implant threaded holes 2080 oriented superiorly relative to the femoral neck cortex. The ribs in this exemplary embodiment provide support for the implant in the axial plane, improved stress transmission from the femoral head portion of implant to the central stem and provide further rotational control during implantation and extended use. A porous surface may be used on the implant undersurface in the same manner as the exemplary embodiment described in FIGS. 20A to 20G.

FIG. 32F is a bottom perspective view of the two-rib-modular hip resurfacing implant and FIG. 32G is an enlarged bottom perspective view of the two-rib-modular hip resurfacing implant in detail, as indicated by a dashed circle around FIG. 32F. The two-rib implant allows for the modular fixation options illustrated in FIGS. 23 to 31, the choice of which are based on individual characteristics of the underlying bone quality and severity of degenerative hip joint disease present. The two added ribs in this exemplary embodiment along the upper aspect of the central stem provide additional rotational resistance during implantation and extended use.

FIG. 33A is a front view and FIG. 33B is a cross-sectional left view, as indicated by line 33B-33B in FIG. 33A, both illustrating various aspects of a four-rib implant 3310, in accordance with another exemplary embodiment of the modular hip resurfacing implant according to the present invention. FIG. 33C is a right view of the two-rib-modular hip resurfacing implant and FIG. 33D is a cross-sectional front view of the two-rib-modular hip resurfacing implant, as indicated by line 33D-33D in FIG. 33C. FIG. 33E is a bottom view of the two-rib-modular hip resurfacing implant further showing its undersurface. The four-rib implant is the same as the implant described in FIGS. 32A to 32G with the following differences. In the present, four-rib exemplary embodiment, the central stem has four equally spaced ribs 3212, circumferentially joined to the top of the central stem. The ribs are joined to the flat, inner planar surface 2070 of the implant and are also joined to the central stem. They are located around the periphery of the central stem, at 90° from each other, as illustrated. The ribs extend from the inner planar undersurface of the implant down the central shaft to the level of the outer rim, but may vary in alternate embodiments. The ribs have sharp outer edges to ease implantation. The implant is designed to be inserted into the central bone channel with one of the two implant threaded holes 2080 oriented superiorly relative to the femoral neck cortex. The ribs in this exemplary embodiment provide support for the implant in both axial and sagittal planes, improved force transmission from the femoral head portion of implant to the central stem and provide rotational resistance during implantation and extended use. A porous surface may be used in the same manner as the exemplary embodiment described in FIGS. 20A to 20G.

FIG. 33F is a bottom perspective view of the four-rib-modular hip resurfacing implant and FIG. 33G is an enlarged bottom perspective view of the four-rib-modular hip resurfacing implant in detail, as indicated by a dashed circle around FIG. 33F. The two-rib implant allows for the modular fixation options illustrated in FIGS. 23 to 31, the choice of which are based on individual characteristics of the underlying bone quality and severity of degenerative hip joint disease present. The four ribs in this exemplary embodiment along the upper aspect of the central stem provide additional rotation resistance during implantation and extended use.

FIG. 34A is a front view and FIG. 34B is a right view, both illustrating various aspects of a cap portion 3411 of a modular stemmed implant, which is a component of a detachable stem-modular hip resurfacing implant, in accordance with another exemplary embodiment of the modular hip resurfacing implant according to the present invention. FIGS. 34C and 34D are cross-sectional left and cross-sectional front views, as illustrated by lines 34C-34C and 34D-34D in FIGS. 34A and 34B, respectively, of the cap portion. The current exemplary embodiment, modular stemmed implant, is the same as the implant described in FIGS. 20A to 20G with the following differences. In the present, modular stemmed implant, the cap portion has a threaded central hole, which receives a modular central stem. A porous surface may be used in the same manner as the exemplary embodiment described in FIGS. 20A to 20G.

FIG. 34E is a bottom view of the cap portion of the modular stemmed implant further showing its undersurface. FIG. 34F is a bottom perspective view of the cap portion of the modular stemmed implant and FIG. 34G is an enlarged bottom perspective view of the cap portion of the modular stemmed implant in detail, as indicated by a dashed circle around FIG. 34F.

FIGS. 34H and 34I are top and front views of a two-rib modular central stem 3416, respectively. The upper threaded aspect of the two-rib modular central stem allows for threaded attachment to the threaded central hole 3412 of the cap portion 3411. FIG. 34J is a top view of a non-ribbed modular central stem 3414. A porous surface may be used in the same manner as the exemplary embodiment described in FIGS. 20A to 20G. FIG. 34K is an exploded front view illustrating the attachment of the non-ribbed modular central stem shown in FIG. 34J to the cap portion of the modular stemmed implant shown in FIG. 34A. This assembly of the detachable stem-modular hip resurfacing 3410 is useful for applications where extensive custom sizing for the central stem is needed for varying applications.

The surgical instruments for hip resurfacing according to the present invention provide means for preparing the proximal femur for a hip resurfacing system including bone cuts along the femoral head while protecting nearby soft tissues, a precise central bone channel within the femoral head and neck, outer holes above and below the central bone channel, and the ability to retract the femoral head following the associated bone cuts. Using these surgical instruments, a precise stepped femoral head osteotomy can be created to accommodate implants designed to match the resulting contours of the femoral head and central bone channel.

Furthermore, the modular hip resurfacing system provides means for both un-cemented and cemented applications and options for multiple modular threaded attachments. Additionally, in multiple exemplary embodiments, additional construct support is provided with fixation at the lateral cortex of the proximal femur with placement of the central screw fitted through the one-hole plate, two-hole plate, or three-hole plate or without a plate. Additional modular options in this system include outer screws, outer pegs, cortical screws, and independent outer screws. In various exemplary embodiments, threaded attachments provide additional construct support for enhanced scalability and resistance to rotation when needed, including for example outer screws, outer pegs, cortical screws and independent outer screws.

Additionally, the alignment guide of the present invention ensures centralized insertion of the guide within the femoral head, while also allowing placement of the guide pin parallel to the femoral neck axis, as needed. Once seated it also allows for ample freedom for rotational adjustment as its arms are without vertical curvature along the height of the arms. Correct positioning can be reliably achieved and confirmed with radiographic imaging using intra-operative fluoroscopic imaging. The alignment pins, arms, ring and the threaded and unthreaded holes allow both visual and radiographic assessment of correct alignment guide seating in multiple image planes. Thereby, the alignment guide permits confirmation of its proper seating onto the femoral head and parallel positioning with respect to the femoral neck axis in coronal and sagittal planes, and additional radiographic imaging planes, as needed. The alignment guide also allows for demarcation of a planned terminal point for cylindrical reaming at a latitudinal location along the surface of the femoral head. The alignment guide makes it possible to insert the guide pin screw, followed by a guide pin. The guide pin can be centered in the femoral head when the alignment guide is utilized and can also be inserted parallel to the femoral neck axis.

The modular cannulated cylindrical reamer is compatible with the guide pin associated with the alignment guide, and can cut away the peripheral bone of the femoral head, to a predetermined latitudinal location about the femoral head, forming a cylindrical shape, without leaving a resultant bone sleeve, while leaving a collar of cortical bone above the articular rim of the femoral head, whereby also reducing risk femoral neck notching. It can simultaneously drill a central bone channel while cutting away the peripheral bone of the femoral head to a predetermined latitudinal location. Another benefit is that it can be modularly adapted in order to drill multiple channel lengths.

The modular hip resurfacing system according to the present invention provides a method for preparing the femoral head and proximal femur for implantation of the associated femoral implant using a novel stepped cylindrical femoral head osteotomy. This includes a cylindrical osteotomy with an associated distal femoral head osteotomy, proximal femoral head osteotomy and central bone channel drilling. The distal osteotomy is performed proximal to the articular rim of the femoral head while leaving the articular rim and a collar of cortical bone above intact. This collar of intact bone above the articular rim is beneficial as it can provide peripheral support of the inner rim of the implant. The orthopedic surgical instruments and modular hip resurfacing femoral implants according to the present invention allow multiple modular fixation options, which are selected to adapt for individual characteristics of associated hip joint disease and underlying bone quality.

While the above description contains much specificity, this should not be construed as limitations on the scope, but rather an exemplification of one or more exemplary embodiments as detailed. Multiple additional modular configurations are possible using the modular hip resurfacing system. For example, another modular configuration can be employed including the modular hip resurfacing implant, a single outer peg above or below the stem, a one-hole plate, and a central screw. Many other variations are possible of the surgical instruments and implants for hip resurfacing according to the present invention.

One such variation relates to the alignment guide. The alignment guide according to at least one embodiment of the present invention ensures centralized insertion of a guide pin within the femoral head, while also allowing placement of the guide pin parallel to the femoral neck axis, as needed. The alignment guide of the present invention also seats and secures only to the femoral head and has multiple arms extending from its base. These arms surround the periphery of the femoral head without seating to the undersurface of the femoral head, with the arms lacking a vertical curvature along the height of the arms in order to allow for ample freedom of rotational adjustment. Furthermore, the alignment guide of the present invention does not utilize a stylus or feeler guide for checking of alignment. Lastly, the alignment guide of the present invention does require adjustment using complex adjustment joints for alternation of its orientation.

With respect to other possible variations of the alignment guide of the present invention, unthreaded holes along the ring at the upper aspect may be added or removed, and arms may be added or removed while keeping at least two arms. It may also be made of alternate materials such as carbon fiber. Additionally, alternate handle designs may be used including alternate removable handles, handles with threaded ends and handles having modified shapes, and additional handle holes may be added to accommodate additional handles. The end of the handle may be angled upwards. Alternately, the removable handle may also be fixed and non-removable. The wings of the guide pin screw may be replaced by other head designs including a hex head while still always retaining the central cannulated aspect. The ring may be enlarged or reduced in diameter. The alignment pins may be modified to include threads to engage the alignment guide. In alternate embodiments, the cannulated guide pin screw may be reduced or enlarged in length with respect to the length of the threaded aspect, or may use a different attachment method including a quick release design. Arm fixation holes may be added or omitted although including them provides a means for securing the alignment guide. Arm fixation holes can also include an internal threading pattern to accept a k-wire with threading at its upper aspect. The upper and/or the lower ridge may be omitted in alternate embodiments. Another alternate alignment guide modification is inclusion of a concave inner surface on each arm, along the width of each arm, while still keeping each arm without a vertical curvature along the height of each arm. The alignment guide may also be manufactured so that the cannulated guide pin screw is non-removable or produced in a manner which includes a hole for the guide pin integral to the alignment guide itself, without use of a cannulated guide pin screw.

The cannulated modular cylindrical reamer assembly creates a precise cylindrical osteotomy of the femoral head and simultaneously drills a central bone channel in the femoral head, femoral neck, and, when required, extending through the lateral cortex of the femoral shaft. The stepped cylindrical femoral head osteotomy as illustrated in FIGS. 1C and 1D is presently preferred as it offers dual planar surfaces at the proximal and distal osteotomy sites and maintains a collar of femoral head cortex above the articular rim. In contrast to previous devices such as the commonly used Birmingham Hip Resurfacing system that involves complete removal of the femoral head cortex above the articular rim, as illustrated in FIG. 1B, the stepped cylindrical femoral head osteotomy according to the present invention provides an advantage in ability for gaining additional peripheral implant support. The modular hip resurfacing system according to the present invention maintains this dense collar of femoral head cortical bone above the articular rim and can utilize it for peripheral support of the inner rim of the implant. Additional alternate embodiments can include wider cutting blades to the cylindrical reamer. Also the cylindrical reamer drill base receptacle may be modified to use a modified attachment method. The cylindrical reamer fastener may also be modified. For example, a spring type split-cotter may be used with a corresponding hole in the upper shaft of the cylindrical reamer drill base to secure the cylindrical reamer just below this point. The hex drill attachment point can be modified to make it cylindrical, still allowing it to be secured to a surgical drill. The overall length of the drill cutting edge can be shortened or lengthened with respect to the total length of the cannulated cylindrical reamer drill base. The modular cylindrical reamer assembly may also be altered and produced so that one or more constituent parts of the modular cylindrical reamer assembly are joined and non-removable.

The saw guide allows for a precise proximal osteotomy at a set distance above the terminal point from the cylindrical reaming. This permits precise fitment of implants matching the contours of the associated bone cuts while ensuring minimal variation in osteotomies between hip resurfacing procedures using the associated surgical instruments of the modular hip resurfacing system. The saw guide allows for the surgical oscillating saw blade to seat and oscillate along the top surface of the saw guide while cutting, thereby ensuring a straight cut at a set height above the distal osteotomy. Additional embodiments of the saw guide can have modified platforms so that the front platform for the oscillating saw guide is still at the correct height corresponding to the proximal osteotomy, but is higher than the left and right platforms in order to lower the left and right platforms away from the oscillating saw blade. Additional embodiments can include wider outer surfaces for the oscillating saw to seat and oscillate along and alteration of the handle design including flat handles, non-removable handles, or use a threaded handle design for an altered method of attachment. The number of platforms may also be reduced. Also, the upper-outer edges of the saw guide including the platforms can have filleted corners. In alternate embodiments the beveled lower edge may be modified to use a fillet edge or may have not bevel or fillet. Additionally, the lower edge may be extended and shaped to surround the collar of intact cortical bone of the femoral head following cylindrical reaming to a predetermined latitudinal location above the articular rim of the femoral head, with different sizes available for varying femoral head diameters. Additionally, alternate handle designs may be used including alternate removable handles, handles with threaded ends and handles having modified shapes. The angled aspect of the handle may have an alternate bend or may be made flat so that the entire aspect of the handle does not angle upwards. Alternately, the removable handle may also be fixed and non-removable. The soft tissue protector with a non-removable handle allows for both protection and retraction of soft tissues near the hip joint and is designed to accommodate simultaneous use of the saw guide. This can be useful during the use of the oscillating saw, cylindrical reaming, fitment of the acetabular cup component and other aspects of the hip resurfacing procedure as well as other surgical procedures around the hip joint where soft tissue retraction and protection are needed. Alternate embodiments can include modifications to the handle including altered shapes, an increased angle along the surface of the handle or alternate bend, and possible use of threaded holes or other attachment points to allow it to be removable accommodating various handle shapes, as desired. Additionally, the curved protector aspect may be modified so that it has a more narrow width and/or does not contain stepped contours along its bottom outer aspects, whereby still allowing simultaneous use with the saw guide. Additionally, alternate handle designs may be used including use of removable handles, handles with threaded ends and handles having modified shapes, or inclusion of additional handles. The angled aspect of the handle may be made flat so that the entire aspect of the handle does not angle upwards.

The hip retractor makes it easier to gain additional retraction after completion of associated cylindrical reaming. The hip retractor can be used to help provide gentle hip retraction during placement of the acetabular component for hip resurfacing while simultaneously protecting the cancellous bone of the femoral head following cylindrical reaming with simultaneous drilling of the central bone channel and proximal osteotomy completion. Alternate embodiments can include one or more threaded removable handles with multiple attachment points. The extended aspect of the hip retractor which includes the handle holes may be removed all together making the upper aspect fully cylindrical and thereby having it serve as more of a protective cap during the procedure rather than a retraction tool. Additional handles can be added or the existing handle can be removed. Additional embodiments can locate the handle centrally at the top surface of the retractor. Additionally, alternate handle designs may be used including use of removable handles, handles with threaded ends and handles having modified shapes. The outer aspect of the handle may be made so that it angles upward. Also, in alternate embodiments the beveled lower edge may be modified to a fillet edge or may have not bevel or fillet. Additionally, the lower edge may be extended and shaped to surround the collar of intact cortical bone of the femoral head following cylindrical reaming to a predetermined latitudinal location above the articular rim of the femoral head, with different sizes available for varying femoral head diameters. The top surface may be modified on alternate embodiments so that it completely covers the cancellous bone, effectively omitting the windows along its outer edges. Or one of the two windows may be omitted. However, inclusion of the windows of the illustrated embodiment can be beneficial as it provides additional visualization of instrument seating. Additional material may be removed from the top surface of the hip retractor, effectively increasing the size of the windows, while keeping the top surface contiguous with the post and remaining upper aspect of the hip retractor.

The outer hole drill guide makes precise drilling of outer holes easier, both above and below the central bone channel. These holes can be used for modular configurations of the modular hip resurfacing system involving use of implant threaded hole/s which are located between the central stem and central rim of the implant. Alternate embodiments can include the addition of extra handles or versions without handles. Additionally, alternate handle designs may be used including use of removable handles, handles with threaded ends and handles having modified shapes. The outer aspect of the handle may be made so that it angles upward. Also, in alternate embodiments the beveled lower edge may be modified to a fillet edge or may have not bevel or fillet. Additionally, the lower edge may be extended and shaped to surround the collar of intact cortical bone of the femoral head following cylindrical reaming to a predetermined latitudinal location above the articular rim of the femoral head, with different sizes available for varying femoral head diameters. The top surface may be modified on alternate embodiments so that it completely covers the cancellous bone, effectively omitting the windows along its outer edges. Or one of the two windows may be omitted. However, inclusion of the windows of the illustrated embodiment can be beneficial as it provides additional visualization of instrument seating. Additional material may be removed from the top surface of the outer hole drill guide, effectively increasing the size of the windows, while retaining the raised drill guides and underlying material and keeping the top surface contiguous with the post and upper aspect of the outer hole drill guide. Also alternate embodiments can include a single raised drill guide for applications where it is desired to only drill a single outer hole. However, two raised drill guides, on either side of the post, is preferred for increased flexibility.

Furthermore, alternate embodiments the modular hip resurfacing implant can include an underside of the cap portion with a concave surface configured to match a convex shape following a cylindrical reaming of the femoral head with a cylindrical reamer which produces a femoral head shape with a convex proximal aspect. The illustrated stepped cylindrical femoral head osteotomy in FIGS. 14C to 14E and configuration of the illustrated embodiments of the modular hip resurfacing implant in FIGS. 20A to 20G, are presently preferred, as this offers dual planar surfaces perpendicular to the implant inner and outer planar surfaces for implant support. The stepped cylindrical femoral head osteotomy can also be modified so that the cylindrical edge of the proximal osteotomy is filleted or chamfered instead of its present 90-degree angle configuration. The present configuration, using a stepped cylindrical femoral head osteotomy, is preferred as it preserves more bone within the femoral head. The present bone cuts are preferred as they retain a collar of femoral head cortex above the articular rim, which provides strong, dense peripheral cortical bone and allowing peripheral support of the inner rim of the implant.

Additional alternate embodiments and ramifications are possible of the modular hip resurfacing femoral implant according to the present invention. The central stem can be modified so that it includes a tapered shape with a wider diameter at the upper aspect transitioning to a narrower diameter along its base. The central stem threaded hole may be omitted although its presence is preferred for providing further modular capabilities. The implant threaded holes may be moved on alternate embodiments to other locations on the implant undersurface, or additional implant threaded holes may be added; corresponding additions may be made to the outer hole drill guide. One or both of the implant threaded holes may also be omitted in alternate embodiments; however, they are desirable as they provide for increased modularity and stability when needed. For example, in the setting of poorer bone quality, the added construct rigidity afforded by addition of outer screws and/or outer pegs, may be especially beneficial and can help further increase durability. Additional embodiments may also include a version of the modular hip resurfacing implant with an inner rim that is taller with corresponding changes made to the bone cuts. However, the current design of the inner rim is presently preferred. Another additional embodiment of the implant may include a version without a joined or removable central stem. Additionally, the central screw may be used to directly engage the cap portion of the modular stemmed implant at a central threaded hole along the base of the cap portion, thereby obviating the need for the removable central stem. Another additional embodiment of the modular hip resurfacing implant with a central stem can be modified to have external exposed threads with corresponding modifications made to its associated modular attachments including the central screw and central cap to have internal threads. This would essentially change the central stem to male, external threads, and the central screw and central cap to female, internal threads. The plates of the modular hip resurfacing system may also be made with alternate contours. The bottom surface contours, which mate to the femoral cortex, can be made to accommodate a slightly more proximal seating so that it seats over the greater trochanter or a slightly more distal seating. Alternately, the plates may be made to have a taller dimension so that they overlap the greater trochanter proximally, and more of the femoral shaft distally. Additional plate designs are possible to accommodate further modular configurations as desired.

Another alternate embodiment of the modular hip resurfacing implant may include wider and longer ribs on the ribbed versions of the central stem, and also a one-, three- or more rib version can be produced. Additionally, with respect to the modular stemmed embodiment of the implant according to the present invention, a one-, two-, three-, four- or more rib version of the stem can be produced. Additionally the plates may be modified to accommodate additional modular configurations. Specifically a two-hole plate can be manufactured to accommodate the central screw with use of an outer screw or cortical screw below it. Additional plates and screws may also be modified to allow the screw threading to engage threading within the hole in the plate, as is well known in the art.

The alignment guide, removable flat handle, alignment pins, cannulated guide pin screw, cylindrical reamer, cannulated cylindrical reamer drill base, cylindrical reamer fastener, cannulated center aspect, saw guide, removable angled handle, fixed angled handle, fixed flat handle, soft tissue protector, hip retractor, outer hole drill guide, screws, and plates may each be made of metal or metal alloy including stainless steel, titanium or aluminum, or another suitable material, or combination of suitable materials. They may be manufactured as cast or using additional standard techniques including injection molding, forging, bending during the machining process, and can be manufactured in segments and welded or otherwise joined, e.g., with an inference fit.

Furthermore, the alignment guide, removable flat handle, cannulated guide pin screw, removable angled handle, soft tissue protector, fixed angled handle, hip retractor, and fixed flat handle, can each further be made from surgical plastic and carbon fiber, or another suitable material, or combination of suitable materials. The cylindrical reamer and cannulated cylindrical reamer drill base can each further be made from surgical plastic, carbon fiber, carbide, and can be manufactured in part and welded or otherwise joined along with additional sharpening of the cutting blades. The cannulated center aspect can further be made using a drill press or other standard techniques. The screws and plates can further be made of high carbon cobalt chrome (CoCr) alloy.

Although the present invention has been described with reference to particular examples and exemplary embodiments, it should be understood that the foregoing description is in no manner limiting. For example, although the present invention has been described with reference to particular materials, manufacturing methods and joining methods, it should be understood that other suitable materials such as for example plastics, other manufacturing methods such as for example injection molding, laser cutting or alternate machining methods, and other joining methods such as for example friction fitting may be encompassed by the present invention. Moreover, the features described herein may be used in any combination.

What is claimed is:

1. A system for performing modular hip resurfacing, comprising:
    an alignment guide configured for sizing of a femoral head and for insertion of a guide pin into the femoral head and a femoral neck;
    a modular cannulated cylindrical reamer assembly configured for cylindrical reaming of the femoral head, distal osteotomy of the femoral head above an articular rim of the femoral head, and drilling of a central bone channel into the femoral head and femoral neck;
    a saw guide configured for guiding a proximal osteotomy of the femoral head, the proximal osteotomy spaced apart from the distal osteotomy and located proximal to the articular rim;
    a soft tissue protector configured for protection and retraction of soft tissues;
    a hip retractor configured for retracting a hip joint following the cylindrical reaming;
    an outer hole drill guide configured for drilling outer holes adjacent to the central bone channel; and
    a modular hip resurfacing implant, the modular hip resurfacing implant including a cap portion and a central stem,
    wherein an underside of the cap portion includes at least one implant threaded hole located between the central stem and a central rim of the cap portion, the at least one implant threaded hole configured for use with modular threaded attachments that are extendable into the femoral head, the femoral neck, and a lateral femoral shaft cortex of a proximal femur, wherein the central stem extends away from the cap portion from a first end to a second end opposite the first end, wherein the second end has threading configured to accommodate threaded attachments;
    wherein the modular cannulated cylindrical reamer assembly includes:
        a cylindrical reamer having (i) cutting blades and (ii) a cylindrical reamer receptacle for modular attachment to a cannulated cylindrical reamer drill base, the cannulated cylindrical reamer drill base having a guide pin hole to accommodate the guide pin; and
        a cylindrical reamer fastener for joining the cylindrical reamer to the cannulated cylindrical reamer drill base;
        wherein when the modular cannulated cylindrical reamer assembly is assembled and secured to a surgical drill, a cylindrical osteotomy associated with the distal osteotomy and the proximal osteotomy is configured to be performed by placing the modular cannulated cylindrical reamer assembly over the guide pin.

2. The system according to claim 1, wherein the modular cannulated cylindrical reamer assembly is configured for drilling into the femoral head, the femoral neck, and through the lateral femoral shaft cortex of the proximal femur.

3. The system according to claim 1, wherein the central stem is removable.

4. The system according to claim 1, wherein the threading at the second end of the central stem includes internal threading.

5. The system according to claim 1, wherein the threading at the second end of the central stem includes external threading.

6. The system according to claim 1, wherein the central stem includes at least one external rib extending at least partially downward from the underside of the cap portion.

7. The system according to claim 1, wherein after bone cuts and seating of the implant, an inner rim of the cap portion is configured to surround a femoral head cortex remaining above the articular rim.

8. The system according to claim 1, wherein the underside of the cap portion further includes at least one of (i) at least one surface configured to match at least one surface of the femoral head, and (ii) at least one porous surface configured to promote bony ingrowth.

9. The system according to claim 8, wherein the modular hip resurfacing implant further includes at least one of:
   a central screw configured to extend from the lateral femoral shaft cortex of the proximal femur to the threading at the second end of the central stem;
   a central cap configured to attach to the threading at the second end of the central stem;
   an independent central screw configured to extend from the lateral femoral shaft cortex of the proximal femur to the threading at the second end of the central stem;
   at least one outer screw configured to extend from the lateral femoral shaft cortex of the proximal femur to the at least one implant threaded hole on the underside of the cap portion;
   at least one independent outer screw configured to extend from the lateral femoral shaft cortex of the proximal femur to the at least one implant threaded hole on the underside of the cap portion;
   at least one outer peg attached to the at least one implant threaded hole on the underside of the cap portion; and
   at least one cortical screw configured to extend from the lateral femoral shaft cortex of the proximal femur.

10. The system according to claim 9, wherein the modular hip resurfacing implant further includes at least one of:
    a plate situated at the lateral femoral shaft cortex of the proximal femur and having at least one hole through which at least one of the (i) central screw, (ii) at least one outer screw, and (iii) at least one cortical screw extends; and
    at least one washer situated at the lateral femoral shaft cortex of the proximal femur and having at least one hole through which at least one of the (i) independent central screw, (ii) at least one independent outer screw, and (iii) at least one cortical screw extends.

11. The system according to claim 1, wherein the modular hip resurfacing implant is configured to be implanted with cement.

12. The system according to claim 1, wherein the alignment guide includes: a plurality of arms joined to and extending from a base of a ring, the plurality of arms having no vertical curvature along a height of each of the plurality of arms, wherein when the alignment guide is seated to the femoral head, the alignment guide is configured to freely rotationally adjust, and the alignment guide is configured to seat and secure only to the femoral head.

13. The system according to claim 12, wherein each arm of the plurality of arms further includes at least one fixation hole configured for insertion of a k-wire to aid in securing the alignment guide to the femoral head.

14. The system according to claim 12, wherein the alignment guide further includes:
    an alignment pin which is configured to be seated into the alignment guide for aiding a positioning of the alignment guide along the femoral head.

15. The system according to claim 12, wherein the alignment guide further includes:
    a removable flat handle having bent ridges along an outer surface thereof, wherein the removable flat handle is not angled upward along an outer side of the ring into which the flat handle is inserted when properly positioned, wherein the removable flat handle is configured to be inserted into handle holes of the alignment guide, and wherein when the removable flat handle is inserted into the alignment guide it aids in a positioning of the alignment guide along the femoral head.

16. The system according to claim 12, wherein the ring includes a threaded ring hole centrally located between the arms of the alignment guide, and wherein the alignment guide further includes: a cannulated guide pin screw which is configured for threading into the threaded ring hole at an upper side of the alignment guide for positioning of the guide pin, and wherein when the cannulated guide pin screw is threaded into the alignment guide, a central hole of the cannulated guide pin screw is disposed at a center of the alignment guide.

17. The system according to claim 1, wherein the saw guide includes:
    at least one platform extending from an upper side of the saw guide;
    a cylindrical inner edge;
    a flat lower bottom surface;
    wherein when the saw guide is placed at a preset latitudinal location above the femoral head following cylindrical reaming, the saw guide is configured to seat upon a flat, planar bone surface at the distal osteotomy and above a remaining collar of intact femoral head cortical bone, and the saw guide is further configured to guide the proximal osteotomy to a height above the distal osteotomy while providing a flat and stabile base for a surgical saw blade.

18. The system according to claim 17, further comprising at least one removable angled handle having bent ridges along an outer surface thereof, the removable angled handle is angled upward when the removable angled handle is positioned properly for insertion into handle holes of the saw guide, and wherein when the removable angled handle is inserted into the saw guide it aids in seating of the saw guide onto the femoral head and stabilization of the saw guide during use of the surgical saw blade.

19. The system according to claim 18, wherein the soft tissue protector includes:
    a curved inner protector side with a stepped shape along its bottom outer sides;
    wherein the soft tissue protector is configured to be simultaneously used and the saw guide, wherein the stepped shape is configured to partially position the soft tissue protector over the at least one removable angled handle of the saw guide allowing for both shielding and retraction of soft tissue near the hip joint.

20. The system according to claim 1, wherein the hip retractor includes:

a post centrally joined to a bottom surface of a base of the hip retractor;

an upper edge of an outer cylindrical surface with at least one fixed handle or configured to be joined to at least one removable handle;

and a cylindrical inner surface opposite the outer cylindrical surface and joined to the base, wherein when the hip retractor is seated to the proximal femur, the hip retractor provides for gentle hip retraction while helping to shield cancellous bone of the femoral head.

21. The system according to claim 1, wherein the outer hole drill guide includes:

a post centrally joined to a top surface of a base at an upper side of the outer hole drill guide;

the upper side further including a cylindrical inner edge joined to the base; and at least one raised drill guide containing a drill guide hole, wherein when the outer hole drill guide is seated to the proximal femur, the outer hole drill guide is configured to properly position the guide pin and to properly position subsequent drilling of at least one outer hole.

22. The system according to claim 1, wherein the outer holes are each aligned parallel to the central bone channel.

23. The system according to claim 1, wherein the cap portion further includes an inner rim, wherein both the central rim and the inner rim are parallel with the central stem from a proximal edge to a distal edge of the central rim and the inner rim.

24. The system according to claim 1, wherein the at least one implant threaded hole is configured for engagement with an outer screw, an independent outer screw, or an outer peg.

25. The system according to claim 1, wherein the underside of the cap portion includes an inner surface and an outer surface, wherein the inner surface and the outer surface are parallel to each other and are disposed perpendicular to an axis of the central stem.

* * * * *